US011007271B2

(12) United States Patent
Gellerman et al.

(10) Patent No.: US 11,007,271 B2
(45) Date of Patent: May 18, 2021

(54) ANTICANCER DRUG CONJUGATES

(71) Applicant: Ariel Scientific Innovations Ltd., Ariel, IL (US)

(72) Inventors: Gary Gellerman, Rishon-LeZion (IL); Yosi Gilad, Ariel (IL); Helena Tuchinsky, Ariel (IL)

(73) Assignee: Ariel Scientific Innovations Ltd., Ariel (IL)

( * ) Notice: Subject to any disclaimer, the term of this patent is extended or adjusted under 35 U.S.C. 154(b) by 0 days.

(21) Appl. No.: 16/082,942

(22) PCT Filed: Jun. 13, 2017

(86) PCT No.: PCT/IL2017/050654
§ 371 (c)(1),
(2) Date: Sep. 7, 2018

(87) PCT Pub. No.: WO2017/216791
PCT Pub. Date: Dec. 21, 2017

(65) Prior Publication Data
US 2019/0224328 A1    Jul. 25, 2019

Related U.S. Application Data

(60) Provisional application No. 62/349,133, filed on Jun. 13, 2016.

(51) Int. Cl.
| | | |
|---|---|---|
| *A61K 31/00* | (2006.01) | |
| *A61K 47/55* | (2017.01) | |
| *A61P 35/00* | (2006.01) | |
| *C07D 491/052* | (2006.01) | |
| *A61K 45/06* | (2006.01) | |
| *C07D 405/04* | (2006.01) | |
| *C07D 519/00* | (2006.01) | |
| *C07D 309/14* | (2006.01) | |
| *C07D 221/14* | (2006.01) | |
| *A61K 31/165* | (2006.01) | |
| *A61K 31/196* | (2006.01) | |
| *A61K 31/4745* | (2006.01) | |
| *A61K 31/704* | (2006.01) | |
| *A61K 31/7068* | (2006.01) | |

(52) U.S. Cl.
CPC ............ *A61K 47/55* (2017.08); *A61K 31/165* (2013.01); *A61K 31/196* (2013.01); *A61K 31/4745* (2013.01); *A61K 31/704* (2013.01); *A61K 31/7068* (2013.01); *A61K 45/06* (2013.01); *A61P 35/00* (2018.01); *C07D 221/14* (2013.01); *C07D 309/14* (2013.01); *C07D 405/04* (2013.01); *C07D 491/052* (2013.01); *C07D 519/00* (2013.01)

(58) Field of Classification Search
CPC .... A61K 47/55; A61K 31/704; A61K 31/165; A61K 31/4745; A61K 31/196; A61K 31/7068; A61P 35/00

USPC ............................................................ 514/34
See application file for complete search history.

(56) References Cited

U.S. PATENT DOCUMENTS

| | | | | |
|---|---|---|---|---|
| 2008/0118518 | A1* | 5/2008 | Cirrito ................... | A61K 31/00 424/155.1 |
| 2008/0176885 | A1* | 7/2008 | Holtman .............. | A61K 47/481 514/282 |
| 2013/0122056 | A1* | 5/2013 | Zhang ................... | A61K 31/337 424/400 |

FOREIGN PATENT DOCUMENTS

| | | |
|---|---|---|
| WO | WQ-2008086008 A1 * | 7/2008 |
| WO | WO 2012/083145 | 6/2012 |
| WO | WO 2012/123774 | 9/2012 |
| WO | WO 2016/196890 | 12/2016 |
| WO | WO 2017/216791 | 12/2017 |

OTHER PUBLICATIONS

Gheeya et al. (Cancer Letters 293 (2010) 124-131).*
International Search Report and the Written Opinion dated Aug. 2, 2017 From the International Searching Authority Re. Application No. PCT/IL2017/050654. (21 Pages).
Aryal et al. "Combinatorial Drug Conjugation Enables Nanoparticle Dual-Drug Delivery", Small, 6(13): 1442-1448, Jul. 5, 2010.
Bombuwala et al. "Colchitaxel, A Coupled Compound Made From Microtubule Inhibitors Colchicine and Paclitaxel", Beilstein Journal of Organic Chemistry, 2(13): 1-9, Jun. 30, 2006.
Bremner et al. "Dual Action-Based Approaches to Antibacterial Agents", Current Medicinal Chemistry, 14(13): 1459-1477, Jun. 1, 2007.
Chirapu et al. "Undesired Vs. Designed Enzymatic Cleavage of Linkers for Liver Targeting", Bioorganic & Medicinal Chemistry Letters, 24(4): 1144-1147, Feb. 15, 2014.
Harrap et al. "Studies on the Toxicity and Antitumour Activity of Prednimustine, A Prednisolone Ester of Chlorambucil", European Journal of Cancer, 13(8): 873-881, Aug. 31, 1977.
Hou et al. "Gemcitabine—Camptothecin Conjugates: A Hybrid Prodrug for Controlled Drug Release and Synergistic Therapeutics", Biomaterials Science Abstract & Electronic Supplementary Material (ESI), Supplementary Information, 12 P., Jun. 23, 2017. Abstract and Supprting Information.

(Continued)

*Primary Examiner* — Shaojia A Jiang
*Assistant Examiner* — Michael C Henry

(57) ABSTRACT

Provided herein is a conjugate comprising two residues of structurally and/or mechanistically different anticancer bioactive agents, coupled to one another by a biocleavable linking moiety, as well as methods of treating cancer using the same and pharmaceutical compositions comprising the same.

19 Claims, 6 Drawing Sheets

(56) References Cited

OTHER PUBLICATIONS

Hu et al. "Synergistic Combination Chemotherapy of Camptothecin and Floxuridine Through Self-Assembly of Amphiphilic Drug-Drug Conjugate", Bioconjugate Chemistry, 260 (12): 2497-2506, Published Online Nov. 5, 2015.

Hubschwerlen et al. "Designs, Synthesis and biological Evaluation of Oxazolidine-Quinolone Hybrids", Bioorganic & Medicinal Chemistry, 11(10): 2313-2319, May 15, 2003.

Kryczka et al. "Two Novel Nucleoside Ester Derivatives of Chlorambucil as Potential Antileukemic Prodrugs: A Preliminary Study", Anti-Cancer Drugs, 18(3): 301-310, Mar. 1, 2007.

Leese et al. "Chimeric Microtubule Disruptors", Chemical Communications, ChemComm, 46(17): 2907-2909, May 7, 2010.

Leese et al. "Tetrahydroisoquinolinone-Based Steroidomimetic and Chimeric Microtubule Disruptors", ChemMedChem, 9(1): 85-108, Jan. 1, 2014.

Lewke et al. "Enzymatic Cleavage of Amino Acid Carbamates", Annals of the New York Academy of Sciences, 542(1): 343-345, Dec. 1, 1988.

Ma et al. "Synergistic Antitumor Activity of a Self-Assembling Camptothecin and Capecitabine Hybrid Prodrug for Improved Efficacy", Journal of Controlled Release, 10 P., Available Online Jan. 10, 2017. Abstract.

Menger et al. "Synthesis and Reactivity of 5-Gluorouracil/Cytarabine Mutual Prodrugs", Journal of Organic Chemistry, 62(26): 9083-9088, Dec. 26, 1997.

Monnerat et al. "A Rare Case of Prednimustine-Induced Myoclonus", Journal of the National Cancer Institute, JNCI, 89(2): 173-174, Jan. 15, 1997.

Passarella et al. "Inhibitors of Tubulin Polymerization: Synthesis and Biological Evaluation of Hybrids of Vindoline, Anhydrovinblastine and Vinorelbine With Thiocolchicine, Podophyllotoxin and Baccatin III", Bioorganic & Medicinal Chemistry, 16(11): 6269-6285, Published Online May 28, 2008.

Punganuru et al. "Colchicine-Based Hybrid Anticancer Dnigs to Combat Tumor Heterogeneity", Medicinal Chemistry, 6(3): 165-173, Mar. 29, 2016.

Stengel et al. "In Vivo and In Vitro Properties of STX2484: A Novel Non-Steroidal Anti-Cancer Compound Active in Taxane-Resistant Breast Cancer", British Journal of Cancer, BJC, 111(2): 300-308, Published Online Jun. 24, 2014.

Uecker et al. "Chimeric Tyrosine Kinase-HDAC Inhibitors as Antiproliferative Agents", Anti-Cancer Drugs, 21(8): 759-765, Sep. 1, 2010.

Vilanova et al. "Design and Synthesis of Pironetin Analogue/Colchicine Hybrids and Study of Their Cytotoxic Activity and Mechanisms of Interaction With Tubulin", The Journal of Medicinal Chemistry, 57(24): 10391-10403, Nov. 26, 2014.

Yang et al. "Synthesis and Biological Evaluation of Novel Conjugates of Camptothecin and 5-Flurouracil as Cytotoxic Agents", Journal of the Brazilian Chemical Society, 22(2): 308-312, Feb. 2011.

Zefirova et al. "Synthesis and SAR Requirements of Adamantane-Colchicine Conjugates With Both Microtubule Depolymerizing and Tubulin Clustering Activities", Bioorganic & Medicinal Chemistry, 19(18): 5529-5538, Available Online Jul. 28, 2011.

International Preliminary Report on Patentability dated Dec. 27, 2018 From the International Bureau of WIPO Re. Application No. PCT/IL2017/050654. (15 Pages).

\* cited by examiner

358, PC-3, 24hr

358, PC-3, 48hr

358, HM, 24hr

358, HM, 48hr

358MDAMB231-48hr

358-A172-48hr

ANTICANCER DRUG CONJUGATES

RELATED APPLICATIONS

This application is a National Phase of PCT Patent Application No. PCT/IL2017/050654 having International Filing Date of Jun. 13, 2017, which claims the benefit of priority under 35 USC § 119(e) of U.S. Provisional Patent Application No. 62/349,133 filed on Jun. 13, 2016. The contents of the above applications are all incorporated by reference as if fully set forth herein in their entirety.

FIELD AND BACKGROUND OF THE INVENTION

The present invention, in some embodiments thereof, relates to pharmaceuticals and, more particularly, but not exclusively, to a class of active agent conjugates that exhibit synergistic anticancer activity.

Administration of drug combinations is a promising therapeutic strategy to enhance the effectiveness of the treatment and overcome the limitation of the utility of many potential drugs. Combined drug treatment is mostly used in cancer therapy and antimicrobial treatment with expectation to afford therapeutic effect at lower doses to lessen side-effects and toxicity, and in addition to overcome development of drug resistance and improve specificity of synergistic combinations towards specific biological systems.

In addition to drug combinations as mixtures, researchers also utilize chemical conjugation to gain drug synergism, wherein drugs or molecular pharmacophores were linked covalently to form molecular conjugates with optimized potency.

This strategy has been pursued in recent years to overcome bacterial resistance to antibiotic drugs, by employing a combination of two different antibiotic drugs in one molecule, wherein each drug moiety is designed to bind independently to different biological targets and synchronously accumulate at both target sites. Such dual action drugs, also referred to as hybrid drugs or conjugate drugs, offer the possibility to overcome current resistance. In addition, these conjugate drugs may reduce the appearance of new resistant strains [Bremner, J B. et al., *Curr Med Chem*, 2007, 14(13), 1459-77; and Hubschwerlen, C., et al., *Bioorg Med Chem*, 2003. 11(10), p. 2313-9].

A similar approach was implemented in anticancer drugs in an attempt to increase efficacy while reducing non-specific toxicity and combat multiple drug resistance [Leese M P. et al., *Chem. Commun.*, 2010, 46, 2907-2909; Leese M. P. et al., *Chem Med Chem.*, 2014 9(1), 85-108; Stengel, C. et al., *British Journal of Cancer*, 2014, 111, 300-308; Uecker, A. et al., *Anticancer Drugs*, 2010, 21(8), 759-65; Harrap, K R. et al., *European Journal of Cancer*, 1977, 13(8), 873-881; Monnerat, C., et al., *J. National Cancer Institute*, 1997, 89(2), 173-174; and Kryczka, T. et al., *Anti-Cancer Drugs*, 2007, 18(3), 301-310].

Additional background art includes WO 2003/040104, WO 2009/037592, WO 2003/044034, U.S. Patent Application Publication No. 2008300199, U.S. Pat. No. 7,973,022, Pokrovskaya, V. et al., *J. Med. Chem.*, 2009, 52, 2243-2254.

SUMMARY OF THE INVENTION

The conjugate provided herein includes the residues of two different anticancer drugs covalently joint by a biocleavable linking moiety, which confers, upon administration and cleavage of the linking moiety, a synergistic and/or cumulative effect that assists in overcome drug resistance in the target cells. The conjugate is designed such that the molecular remnants of biocleaving the linking moiety on the drugs is null and adds or subtracts a benign naturally occurring molecule to the medium. The two drugs are preferably selected from known anticancer drugs than have been approved for use form safety considerations, but are currently considered less effective due to low or moderate therapeutic efficacy.

According to an aspect of some embodiments of the present invention there is provided a conjugate that includes:
(a) a residue of a first anticancer bioactive agent having a first chemical structure;
(b) a residue of a second anticancer bioactive agent having a second chemical structure; and
(c) a linking moiety covalently bonding the first residue and the second residue to form the conjugate, wherein:
the first bioactive agent is different than the second bioactive agent;
the first bioactive agent and the second bioactive agent have a first functional group and a second functional group, respectively;
the linking moiety is a biocleavable moiety being formed by coupling the first functional group and the second functional group, such that biocleaving the linking moiety releases both the first anticancer bioactive agent characterized by the first chemical structure and the second anticancer bioactive agent characterized by the second chemical structure; and
biocleaving the linking moiety consumes or releases a molecule that is naturally present in mammalian cells.

According to some embodiments of the invention, the molecule that is naturally present in mammalian cells is selected from the group consisting of $H_2O$, $CO_2$ and $H_2CO$.

According to some embodiments of the invention, each of the first functional group and the second functional group is selected from the group consisting of amine, hydroxyl, carboxyl and ester.

According to some embodiments of the invention, the linking moiety is selected from the group consisting of ester, amide, carbamate, oxime, imide, acetal/ketal, carbonate and phosphate ester.

According to some embodiments of the invention, each of the first bioactive agent and the second bioactive agent is independently characterized by a first therapeutic activity and a second therapeutic activity, respectively, and at least one of the first therapeutic activity and the second therapeutic activity is a low or moderate therapeutic activity.

According to some embodiments of the invention, each of the first therapeutic activity and the second therapeutic activity is a low or moderate therapeutic activity.

According to some embodiments of the invention, the conjugate is characterized by exerting a therapeutic activity greater than each of the first therapeutic activity and the second therapeutic activity alone or in combination.

According to some embodiments of the invention, the anticancer bioactive agent is selected from the group consisting of amonafide, camptothecin, chlorambucil, colchicine, cytarabine, cytarabine and doxorubicin.

According to some embodiments of the invention, the first bioactive agent is camptothecin, the second bioactive agent is chlorambucil and the linking moiety is ester.

According to some embodiments of the invention, the first bioactive agent is camptothecin, the second bioactive agent is colchicine and the linking moiety is carbamate.

According to some embodiments of the invention, the first bioactive agent is amonafide, the second bioactive agent is chlorambucil and the linking moiety is amide.

According to some embodiments of the invention, the first bioactive agent is amonafide, the second bioactive agent is camptothecin and the linking moiety is carbamate.

According to some embodiments of the invention, the first bioactive agent is cytarabine, the second bioactive agent is chlorambucil and the linking moiety is amide.

According to some embodiments of the invention, the first bioactive agent is doxorubicin, the second bioactive agent is chlorambucil and the linking moiety is amide.

According to some embodiments of the invention, the first bioactive agent is doxorubicin, the second bioactive agent is camptothecin and the linking moiety is carbamate.

According to some embodiments of the invention, the first bioactive agent is cytarabine, the second bioactive agent is camptothecin and the linking moiety is carbamate.

According to some embodiments of the invention, examples of the conjugate presented herein include, without limitation, Chimera 356, Chimera 357, Chimera 358, Chimera 359, Chimera 360, Chimera 361, Chimera 362 and Chimera 363.

According to an aspect of some embodiments of the present invention there is provided a pharmaceutical composition that includes the conjugate presented herein, as an active ingredient, and a pharmaceutically acceptable carrier.

According to some embodiments of the invention, the pharmaceutical composition is packaged in a packaging material and identified in print, in or on the packaging material, for use in the treatment of cancer.

According to an aspect of some embodiments of the present invention there is provided a use of the conjugate presented herein, in the preparation of a medicament.

According to some embodiments of the invention, the medicament is for treating cancer.

According to an aspect of some embodiments of the present invention there is provided a method of treating cancer in a subject, the method that includes, administering to the subject a therapeutically effective amount of the conjugate presented herein or the pharmaceutical composition presented herein.

According to an aspect of some embodiments of the present invention there is provided a process of preparing the conjugate presented herein, the process that includes coupling the first bioactive agent to the second bioactive agent via the first functional group and the second functional group, to thereby form the linking moiety.

According to some embodiments of the invention, the process further includes, prior to the coupling step, modifying at least one of the first bioactive agent or the second bioactive agent so as to exhibit the first functional group or the second functional group, respectively.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-1F present comparative plots of the results of the cytotoxicity studies of Chimera 358, an exemplary conjugate according to embodiments of the present invention, consisting of a residue of Amonafide (AM) and a residue of Chlorambucil (CLB), as obtained from exposure of three types of human cell lines to 5-25 μM of Chimera 358, wherein FIG. 1A shows the dose response on PC-3 cells viability during a 24 hours incubation period, FIG. 1B shows the dose response on PC-3 cells viability during a 48 hours incubation period, FIG. 1C shows the dose response on WM-266-4 cell cells viability during a 24 hours incubation period, FIG. 1D shows the dose response on WM-266-4 cell cells viability during a 48 hours incubation period, FIG. 1E shows the dose response on MDA-MB 231 cells viability during a 24 hours incubation period, and FIG. 1F shows the dose response on MDA-MB 231 cells viability during a 24 hours incubation period (response to AM alone marked by diamonds, to CLB by squares, the mixture of AM and CLB by triangles and Chimera 358 marked by circles);

DESCRIPTION OF SPECIFIC EMBODIMENTS OF THE INVENTION

Figure 1A:
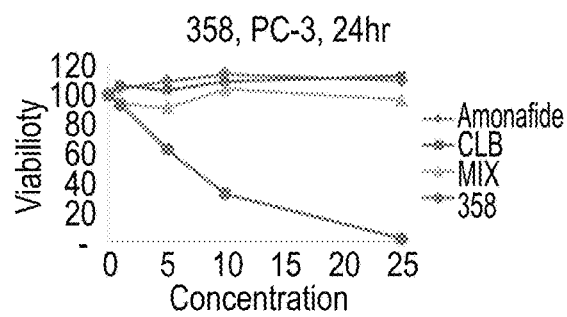

The present invention, in some embodiments thereof, relates to pharmaceuticals and, more particularly, but not exclusively, to a class of active agent conjugates that exhibit synergistic anticancer activity.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

As discussed hereinabove, the chemistry of mutually acting (synergistic) drugs has received much attention. While conceiving the present invention, it was envisioned by the present inventors that harnessing the therapeutic potential of two moderate or low efficacy drugs conjugated into one chimeric entity, or conjugate, may afford a single active agent that would exhibit activity not seen in any of its parts when used alone. Using less effective drugs, which have been previously approved for use, is advantageous also in terms of regulatory aspects.

The present invention provides the advantage of using drugs that have already been approved for clinical use but have lost their utility for various reasons, or drug candidates that have passed some clinical trials but were found inferior for one or more pharmacological aspects (e.g., efficacy, toxicity etc.). Such moderately active agents that are not sufficiently active on cancerous cells when used apart, may be found remarkably active when merged into one conjugated active agent.

Albeit conjugating two molecular entities may seem to be straight forward, conjugation of two active entities into one more active entity is not trivial. Conjugation parameters include selection of a linker attachment site, linker liability, linker length and type, and the design of drug analogs for, or the identification of attachment points suitable for linking without abolishing activity. While reducing the present invention to practice, a covalent and biodegradable linkage was used to conjugate two anticancer drugs to form a highly potent anticancer chimeric agent with distinguished spectral properties for imaging. The presently provided conjugates were shown to be inactive on benign fibroblast, strengthening its utilization as selective and efficient anticancer drug entities.

Conjugate:

Thus, according to an aspect of embodiments of the present invention, there is provided a conjugate that includes a residue of a first anticancer bioactive agent, a residue of a second anticancer bioactive agent and a linking moiety covalently bonding the residues to one another. In order to benefit from a synergistic or cumulative effect and overcome problems associated with resistant target cells, the first and second anticancer bioactive agents are selected different in structure and therefore in function. In some embodiments, the first and second anticancer bioactive agents differ from one another by their mechanism of conferring a therapeutic activity, as discussed hereinbelow.

According to this aspect of the present invention, the conjugate is constructed by forming a biocleavable linking moiety from a first functional group inherently present on the first anticancer bioactive agent, and a second functional group inherently present on the second anticancer bioactive agent, by a coupling reaction that forms the biocleavable linking moiety. Further according to this aspect of the present invention, biocleaving the linking moiety regenerates the original first anticancer bioactive agent and the second anticancer bioactive agent in terms of their chemical structure. In other words, the conjugate is an adduct of two residues of anticancer bioactive agents, the first anticancer bioactive agent is having a first chemical structure and the second anticancer bioactive agent a second chemical structure, the two residues are bonded together via a biocleavable linking moiety, and the conjugate is designed such that upon cleaving the linking moiety, the first anticancer bioactive agent is released in its "original" first chemical structure and the second anticancer bioactive agent is released in its "original" second chemical structure, without any deficit or surplus of atoms, electrons or bonds. Further according to this aspect of the present invention, the conjugate is designed to cleave under biological/physiological conditions such that the two anticancer agents are released from the conjugated form and become available and bioactive essentially at the site where the conjugate is cleaved.

According to some embodiments, the molecular remnants of biocleaving the linking moiety in the conjugates presented herein are null in the context of the first and second bioactive agents (no atoms, bonds of electrons are subtracted or added thereto), and are null or in the form of benign small solvent or gas molecules in terms of the total net impact to the surrounding medium, namely an addition (release of a byproduct) or subtraction (consumption of solvent) of a water molecule or a carbon dioxide molecule in the medium. In some embodiments of the present invention, the biocleavage of the linking moiety is a hydrolysis process in which a water molecule is hydrolyzed, and in some embodiments a carbon dioxide molecule is generated. In is noted that a consumption of $H_2O$ (water) and a release of $CO_2$ (carbon dioxide) can be seen as a net total impact of releasing a $H_2CO$ (formaldehyde) molecule.

Bioactive Agent:

As discussed hereinabove, the conjugate presented herein is designed to carry a dual-drug payload, which comprise two different drugs, referred to herein as the first and the second bioactive agent, linked by a labile linking moiety. The advantages of the conjugates of the present invention stems from the simultaneous (concerted) release of the drugs, and can therefore be specifically advantageous in cases where the different drugs confer a cumulative and/or a synergistic effect. Use of the conjugate presented herein offers an additional advantage when at least one of the conjugated active agents is characterized by a low or moderate beneficial activity when used alone or even when administered as a mixture with the other bioactive agent. The dual-drug payload strategy, afforded by the presently provided conjugates, forms the conditions for a synergistic effect between the two drugs such that would not be conferred or conferred to a lesser extent when each is administered alone or as a mixture.

According to some embodiments, at least one of the first and second bioactive agent is characterized by a low or moderate therapeutic activity. According to some embodiments, both the first and second bioactive agents are characterized by a low or moderate therapeutic activity. According to some embodiments, each of the first therapeutic activity and the second therapeutic activity is a low or moderate therapeutic activity.

According to some embodiments, the conjugate is characterized by a therapeutic activity which is greater than each of the first therapeutic activity and the second therapeutic activity, as expressed by using the first and the second bioactive agents alone, or in combination as a mixture of two bioactive agents. This greater therapeutic activity exerted by the conjugate, with respect to the therapeutic activities of its members, is referred to herein as a synergistic therapeutic activity.

In the context of the present embodiments, the terms "bioactive agent", "pharmaceutically active agent" and "drug" are used interchangeably.

As used herein, the terms "bioactive agent" and "drug" refer to small molecules or biomolecules that alter, inhibit, activate, or otherwise affect a biological mechanism or event. Bioactive agent that can be conjugated, according to embodiments of the present invention, are anticancer bioactive agents, which include, but are not limited to, anticancer substances for all types and stages of cancer and cancer treatments (chemotherapeutic, proliferative, acute, genetic, spontaneous etc.), anti-proliferative agents, chemosensitizing agents, anti-inflammatory agents (including steroidal and non-steroidal anti-inflammatory agents and anti-pyretic agents), anti-oxidants, hormones, immunosuppressants, enzyme inhibitors, cell growth inhibitors and anti-adhesion molecules, inhibitors of DNA, RNA or protein synthesis, anti-angiogenic factors, anti-secretory factors, radioactive agents and imaging agents. A more comprehensive listing of exemplary drugs suitable for use in the present invention may be found in "Pharmaceutical Substances: Syntheses, Patents, Applications" by Axel Kleemann and Jurgen Engel, Thieme Medical Publishing, 1999; the "Merck Index: An Encyclopedia of Chemicals, Drugs, and Biologicals", edited by Susan Budavari et al., CRC Press, 1996, and the United States Pharmacopeia-25/National Formulary-20, published by the United States Pharmcopeial Convention, Inc., Rockville Md., 2001.

As used herein, the term "small molecule" refers to molecules, whether naturally-occurring or artificially created (e.g., via chemical synthesis), that have a relatively low molecular weight. Typically, small molecules are monomeric and have a molecular weight of less than about 1500 Da. Preferred small molecules are biologically active in that they produce a local or systemic effect in animals, preferably mammals, more preferably humans. In certain preferred embodiments, the small molecule is a drug. Preferably, though not necessarily, the drug is one that has already been deemed safe and effective for use by the appropriate governmental agency or body. For example, drugs for human use listed by the FDA under 21 C.F.R. §§ 330.5, 331 through 361, and 440 through 460; drugs for veterinary use listed by the FDA under 21 C.F.R. §§ 500 through 589, are all considered acceptable for use in accordance with the present invention.

Anticancer drugs that can form the conjugate, according to some embodiments of the invention include, but are not limited to Amonafide; Camptothecin; Colchicine; Chlorambucil; Cytarabine; Doxorubicin; 3-(9-Acridinylamino)-5-(hydroxymethyl)aniline; Azatoxin; Acivicin; Aclarubicin; Acodazole Hydrochloride; Acronine; Adriamycin; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Cirolemycin; Cisplatin; Cladribine; Crisnatol Mesylate; Cyclophosphamide; Dacarbazine; Dactinomycin; Daunorubicin Hydrochloride; Decitabine; Dexormaplatin; Dezaguanine; Dezaguanine Mesylate; Diaziquone; Docetaxel; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Etoposide; Etoposide Phosphate; Etoprine; Fadrozole Hydrochloride; Fazarabine; Fenretinide; Floxuridine; Fludarabine Phosphate; Fluorouracil; Flurocitabine; Fosquidone; Fostriecin Sodium; Gemcitabine; Gemcitabine Hydrochloride; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-I a; Interferon Gamma-I b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Sulofenur; Talisomycin; Taxol; Tecogalan Sodium; Tegafur; Teloxantrone Hydrochloride; Temoporfin; Teniposide; Teroxirone; Testolactone; Thiamiprine; Thioguanine; Thiotepa; Tiazofuirin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride.

Additional antineoplastic and anticancer agents include those disclosed in Chapter 52, Antineoplastic Agents (Paul Calabresi and Bruce A. Chabner), and the introduction thereto, 1202-1263, of Goodman and Gilman's "The Pharmacological Basis of Therapeutics", Eighth Edition, 1990, McGraw-Hill, Inc. (Health Professions Division).

Non-limiting examples of anticancer chemotherapeutic agents that can form the conjugate, according to some embodiments of the invention, include amino containing chemotherapeutic agents such as daunorubicin, doxorubicin, N-(5,5-diacetoxypentyl)doxorubicin, anthracycline, mitomycin C, mitomycin A, 9-amino aminopertin, antinomycin, $N^8$-acetyl spermidine, 1-(2-chloroethyl)-1,2-dimethanesulfonyl hydrazine, bleomycin, tallysomucin, and derivatives thereof; hydroxy containing chemotherapeutic agents such as etoposide, irinotecaan, topotecan, 9-amino camptothecin, paclitaxel, docetaxel, esperamycin, 1,8-dihydroxy-bicyclo [7.3.1]trideca-4-ene-2,6-diyne-13-one, anguidine, morpholino-doxorubicin, vincristine and vinblastine, and derivatives thereof, sulfhydril containing chemotherapeutic agents and carboxyl containing chemotherapeutic agents. Additional chemotherapeutic agents include, without limitation, an alkylating agent such as a nitrogen mustard, an ethylenimine and a methylmelamine, an alkyl sulfonate, a nitrosourea, and a triazene; an antimetabolite such as a folic acid analog, a pyrimidine analog, and a purine analog; a natural product such as a vinca alkaloid, an epipodophyllotoxin, an antibiotic, an enzyme, a taxane, and a biological response modifier; miscellaneous agents such as a platinum coordination complex, an anthracenedione, an anthracycline, a substituted urea, a methyl hydrazine derivative, or an adrenocortical suppressant; or a hormone or an antagonist such as an adrenocorticosteroid, a progestin, an estrogen, an antiestrogen, an androgen, an antiandrogen, a gonadotropin-releasing hormone analog, bleomycin, doxorubicin, paclitaxel, 4-OH cyclophosphamide and cisplatinum.

According to some embodiments, the first bioactive agent and the second bioactive agent that are conjugated to form the presently provided conjugates are different, namely the two bioactive agents are not the same in structure, and/or in structure and mechanism of action. Without being bound by any particular theory, it is assumed that conjugated drugs exhibiting a different mechanism of action would exhibit a more notable synergistic effect on each other in terms of their therapeutic activity.

According to some embodiments, at least one of the first and second anticancer bioactive agent forming the conjugate presented herein is an approved for use by one or more drug approval authority (e.g., FDA) yet characterized by a low or moderate anticancer activity. According to some embodiments, both the first and second anticancer bioactive agents are characterized by a low or moderate anticancer therapeutic activity.

By "low or moderate anticancer therapeutic activity" it is meant that use of such a drug is regarded as not sufficient to relieve to some extent one or more of the symptoms of the condition being treated by being at a level that is harmful to the target cells, and cause a disruption to the life-cycle of the target cells. Alternatively or in addition, a drug is regarded as having a low or moderate anticancer therapeutic activity when it is cytotoxic to the target cells but not sufficiently specific to the target cells, and/or toxic to non-targeted cells. Although such drugs are effective in killing target cells, they may not be useful at their therapeutically effective amount due to adverse and toxic effects.

As used herein, the phrase "therapeutically effective amount" describes an amount of an active agent or a conjugate being administered, which will relieve to some extent one or more of the symptoms of the medical condition being treated. In the context of the present embodiments, the phrase "therapeutically effective amount" describes an amount of a conjugate being administered, which will be cytotoxic to targeted cells, and/or relieve to some extent one or more of the symptoms of the condition being treated by being at a level that is harmful to the target cell(s), and cause a disruption to the life-cycle of the target cell(s). In some embodiments, the target cells are cancer cells.

Linking Moiety:

As used herein, the term "moiety" describes a group of covalently bonded atoms that form a part of a chemical compound, which typically has certain functionality. As is well accepted in the art in the molecular context, the term "residue", as used herein, refers to a portion, and typically a major portion of a molecular entity, such as molecule or a part of a molecule such as a group, which has underwent a chemical reaction and is now covalently linked to another molecular entity.

As used herein, the words "link,", "linked", "linkage," "linker", "bound" or "attached", are used interchangeably herein and refer to the presence of at least one covalent bond between species or residues, unless specifically noted otherwise.

As used herein, the term "linking moiety" describes a chemical moiety (a group of atoms or a covalent bond) that links two chemical moieties or residues via one or more covalent bonds. A linking moiety may include atoms that form a part of one or both of the chemical moieties it links, and/or include atoms that do not form a part of one or both of the chemical moieties it links. For example, a peptide bond (amide) linking moiety that links two amino acid residues includes at least a nitrogen atom and a hydrogen atom from one amino acid and at least a carboxyl of the other amino acid. In general, the linking moiety can be formed during a chemical reaction, such that by reacting two or more reactive functional groups, the linking moiety is formed as a new chemical entity which can comprise a bond (between two atoms), or one or more bonded atoms. Alternatively, the linking moiety can be an independent chemical moiety comprising two or more reactive functional groups to which the reactive functional groups of other compounds can be attached, either directly or indirectly, as is detailed hereinunder.

The positions by which the bioactive agents are linked together to form the conjugates presented herein, are generally selected such that once cleaved off, any remaining moiety stemming from the linking moiety (or a spacer moiety) on the bioactive agent, if at all, does not substantially preclude its biological activity (mechanism of biological activity). Suitable positions depend on the type of bioactive agent. According to some embodiments of the present invention, the linking moieties are form such that the biological activity of the bioactive agents, once separated, is not abolished and remains substantially the same as the biological activity of a similar pristine bioactive agent. In some embodiments, cleavage of the linking moiety restores the original structure of one or each of the first and second bioactive agents which formed the conjugate.

The terms "functional group", "reactive group" or "reactive functional group" are used herein interchangeably to describe a chemical group that is capable of undergoing a chemical reaction that typically leads to a bond formation. The bond, according to some embodiments of the present invention, is preferably a covalent bond.

Chemical reactions that lead to a bond formation include, without limitation, cycloaddition reactions (such as the Diels-Alder's reaction, the 1,3-dipolar cycloaddition Huisgen reaction, and the similar "click reaction"), condensations, nucleophilic and electrophilic addition reactions, nucleophilic and electrophilic substitutions, addition and elimination reactions, alkylation reactions, rearrangement reactions and any other known organic reactions that involve a reactive group.

Representative examples of reactive groups include, without limitation, acyl halide, aldehyde, alkoxy, alkyne, amide, amine, aryloxy, azide, aziridine, azo, carbamate, carbonyl, carboxyl, carboxylate, cyano, diene, dienophile, epoxy, guanidine, guanyl, halide, hydrazide, hydrazine, hydroxyl, hydroxylamine, imino, isocyanate, nitro, phosphate, phosphonate, sulfinyl, sulfonamide, sulfonate, thioalkoxy, thioaryloxy, thiocarbamate, thiocarbonyl, thiohydroxy, thiourea and urea, as these terms are defined hereinafter.

Non-limiting examples of linking moieties, according to some embodiments of the present invention, include without limitation, amide, carbamate, carbonate, lactone, lactam, carboxylate, ester, cycloalkene, cyclohexene, heteroalicyclic, heteroaryl, triazine, triazole, disulfide, imide, imine, oxime, aldimine, ketimine, hydrazone, semicarbazone, acetal, ketal, aminal, aminoacetal, thioacetal, thioketal, phosphate ester, and the like. Other linking moieties are defined hereinbelow, and further other linking moieties are contemplated within the scope of the term as used herein.

According to some embodiments, the linking moiety is selected from the group consisting of:

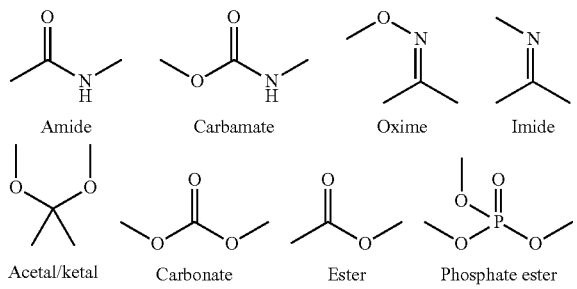

Amide    Carbamate    Oxime    Imide

Acetal/ketal    Carbonate    Ester    Phosphate ester

Definitions of specific functional groups, chemical terms, and general terms used throughout the specification are described in more detail below. For purposes of this invention, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito, 1999; Smith and March March's Advanced Organic Chemistry, 5$^{th}$ Edition, John Wiley & Sons, Inc., New York, 2001; Larock, Comprehensive Organic Transformations, VCH Publishers, Inc., New York, 1989; Carruthers, Some Modern Methods of Organic Synthesis, 3$^{rd}$ Edition, Cambridge University Press, Cambridge, 1987.

As used herein, the terms "amine" or "amino", describe both a —NR'R" end group and a —NR'— linking moiety, wherein R' and R" are each independently hydrogen, alkyl, cycloalkyl, aryl, as these terms are defined hereinbelow.

Herein throughout, the phrase "end group" describes a chemical group that is attached to one compound (a substituent; a reactive group; a functional group etc.), while the term "linking moiety" describes a group that is attached to two compounds and links therebetween.

The amine group can therefore be a primary amine, where both R' and R" are hydrogen, a secondary amine, where R' is hydrogen and R" is alkyl, cycloalkyl or aryl, or a tertiary amine, where each of R' and R" is independently alkyl, cycloalkyl or aryl.

Alternatively, R' and R" can each independently be hydrogen, hydroxyalkyl, trihaloalkyl, cycloalkyl, alkenyl, alkynyl, aryl, heteroaryl, heteroalicyclic, amine, halo, sulfonate, sulfoxide, phosphonate, hydroxy, alkoxy, aryloxy, thiohydroxy, thioalkoxy, thioaryloxy, cyano, nitro, azo, azido, sulfonamide, carbonyl, C-carboxylate, O-carboxylate, N-thiocarbamate, O-thiocarbamate, urea, thiourea, N-carbamate, O-carbamate, C-amide, N-amide, guanyl, guanidine and hydrazine, as these terms are defined herein.

The term "alkyl" describes a saturated aliphatic hydrocarbon including straight chain (unbranched) and branched chain groups. Preferably, the alkyl group has 1 to 20 carbon atoms. Whenever a numerical range; e.g., "1-20", is stated herein, it implies that the group, in this case the alkyl group, may contain 1 carbon atom, 2 carbon atoms, 3 carbon atoms, etc., up to and including 20 carbon atoms. More preferably, the alkyl is a medium size alkyl having 1 to 10 carbon atoms. Most preferably, unless otherwise indicated, the alkyl is a lower alkyl having 1 to 4 carbon atoms. The alkyl group may be substituted or unsubstituted. Substituted alkyl may have one or more substituents, whereby each substituent group can independently be, for example, hydroxyalkyl, trihaloalkyl, cycloalkyl, alkenyl, alkynyl, aryl, heteroaryl, heteroalicyclic, amine, halo, sulfonate, sulfoxide, phosphonate, hydroxy, alkoxy, aryloxy, thiohydroxy, thioalkoxy, thioaryloxy, cyano, nitro, azo, azido, sulfonamide, C-carboxylate, O-carboxylate, N-thiocarbamate, O-thiocarbamate, urea, thiourea, N-carbamate, O-carbamate, C-amide, N-amide, guanyl, guanidine and hydrazine.

The alkyl group can be an end group, as this phrase is defined hereinabove, wherein it is attached to a single adjacent atom, or a linking moiety, as this phrase is defined hereinabove, which connects two or more moieties via at least two carbons in its chain. When an alkyl is a linking moiety, it is also referred to herein as "alkylene", e.g., methylene, ethylene, propylene, etc.

The term "alkenyl" describes an unsaturated alkyl, as defined herein, having at least two carbon atoms and at least one carbon-carbon double bond. The alkenyl may be substituted or unsubstituted by one or more substituents, as described for alkyl hereinabove.

The terms "alkynyl" or "alkyne", as defined herein, is an unsaturated alkyl having at least two carbon atoms and at least one carbon-carbon triple bond. The alkynyl may be substituted or unsubstituted by one or more substituents, as described hereinabove.

The term "cycloalkyl" describes an all-carbon monocyclic or fused ring (i.e., rings that share an adjacent pair of carbon atoms) group where one or more of the rings does not have a completely conjugated pi-electron system. The cycloalkyl group may be substituted or unsubstituted. Substituted cycloalkyl may have one or more substituents, whereby each substituent group can independently be, for example, hydroxyalkyl, trihaloalkyl, cycloalkyl, alkenyl, alkynyl, aryl, heteroaryl, heteroalicyclic, amine, halo, sulfonate, sulfoxide, phosphonate, hydroxy, alkoxy, aryloxy, thiohydroxy, thioalkoxy, thioaryloxy, cyano, nitro, azo, azido, sulfonamide, C-carboxylate, O-carboxylate, N-thiocarbamate, O-thiocarbamate, urea, thiourea, N-carbamate, O-carbamate, C-amide, N-amide, guanyl, guanidine and hydrazine. The cycloalkyl group can be an end group, as this phrase is defined hereinabove, wherein it is attached to a single adjacent atom, or a linking moiety, as this phrase is defined hereinabove, connecting two or more moieties at two or more positions thereof.

The term "heteroalicyclic" describes a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or unsubstituted. Substituted heteroalicyclic may have one or more substituents, whereby each substituent group can independently be, for example, hydroxyalkyl, trihaloalkyl, cycloalkyl, alkenyl, alkynyl, aryl, heteroaryl, heteroalicyclic, amine, halo, sulfonate, sulfoxide, phosphonate, hydroxy, alkoxy, aryloxy, thiohydroxy, thioalkoxy, thioaryloxy, cyano, nitro, azo, azido, sulfonamide, C-carboxylate, O-carboxylate, N-thiocarbamate, O-thiocarbamate, urea, thiourea, O-carbamate, N-carbamate, C-amide, N-amide, guanyl, guanidine and hydrazine. The heteroalicyclic group can be an end group, as this phrase is defined hereinabove, where it is attached to a single adjacent atom, or a linking moiety, as this phrase is defined hereinabove, connecting two or more moieties at two or more positions thereof. Representative examples are piperidine, piperazine, tetrahydrofurane, tetrahydropyrane, morpholino and the like.

The term "aryl" describes an all-carbon monocyclic or fused-ring polycyclic (i.e., rings which share adjacent pairs of carbon atoms) groups having a completely conjugated pi-electron system. The aryl group may be substituted or unsubstituted. Substituted aryl may have one or more substituents, whereby each substituent group can independently be, for example, hydroxyalkyl, trihaloalkyl, cycloalkyl, alkenyl, alkynyl, aryl, heteroaryl, heteroalicyclic, amine, halo, sulfonate, sulfoxide, phosphonate, hydroxy, alkoxy, aryloxy, thiohydroxy, thioalkoxy, thioaryloxy, cyano, nitro, azo, azido, sulfonamide, C-carboxylate, O-carboxylate, N-thiocarbamate, O-thiocarbamate, urea, thiourea, N-carbamate, O-carbamate, C-amide, N-amide, guanyl, guanidine and hydrazine. The aryl group can be an end group, as this term is defined hereinabove, wherein it is attached to a single adjacent atom, or a linking moiety, as this term is defined hereinabove, connecting two or more moieties at two or more positions thereof. Preferably, the aryl is phenyl.

The term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine. The heteroaryl group may be substituted or unsubstituted. Substituted heteroaryl may have one or more substituents, whereby each substituent group can independently be, for example, hydroxyalkyl, trihaloalkyl, cycloalkyl, alkenyl, alkynyl, aryl, heteroaryl, heteroalicyclic, amine, halo, sulfonate, sulfoxide, phosphonate, hydroxy, alkoxy, aryloxy, thiohydroxy, thioalkoxy, thioaryloxy, cyano, nitro, azo, azido, sulfonamide, C-carboxylate, O-carboxylate, N-thiocarbamate, O-thiocarbamate, urea, thiourea, O-carbamate, N-carbamate, C-amide, N-amide, guanyl, guanidine and hydrazine. The heteroaryl group can be an end group, as this phrase is defined hereinabove, where it is attached to a single adjacent atom, or a linking moiety, as this phrase is defined hereinabove, connecting two or more moieties at two or more positions thereof. Representative examples are pyridine, pyrrole, oxazole, indole, purine and the like.

The term "alkaryl" describes an alkyl, as defined herein, which is substituted by one or more aryl or heteroaryl groups. An example of alkaryl is benzyl.

The term "amine-oxide" describes a —N(OR')(R") or a —N(OR')— group, where R' and R" are as defined herein. This term refers to a —N(OR')(R") group in cases where the amine-oxide is an end group, as this phrase is defined hereinabove, and to a —N(OR')— group in cases where the amine-oxime is an end group, as this phrase is defined hereinabove.

As used herein, the term "acyl" refers to a group having the general formula —C(=O)R', —C(=O)OR', —C(=O)—O—C(=O)R', —C(=O)SR', —C(=O)N(R')$_2$, —C(=S)R', —C(=S)N(R')$_2$, and —C(=S)S(R'), —C(=NR')R", —C(=NR')OR", —C(=NR')SR", and —C(=NR')N(R")$_2$, wherein R' and R" are each independently hydrogen, halo, substituted or unsubstituted hydroxyl, substituted or unsubstituted thiol, substituted or unsubstituted amine, substituted or unsubstituted acyl, cyclic or acyclic, substituted or unsubstituted, branched or unbranched aliphatic, cyclic or acyclic, substituted or unsubstituted, branched or unbranched heteroaliphatic, cyclic or acyclic, substituted or unsubstituted, branched or unbranched alkyl, cyclic or acyclic, substituted or unsubstituted, branched or unbranched alkenyl, substituted or unsubstituted alkynyl, substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two $R^{X1}$ groups taken together form a 5- to 6-membered heterocyclic ring. Exemplary acyl groups include aldehydes (—CHO), carboxylic acids (—CO$_2$H), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

As used herein, the term "aliphatic" or "aliphatic group" denotes an optionally substituted hydrocarbon moiety that may be straight-chain (i.e., unbranched), branched, or cyclic ("carbocyclic") and may be completely saturated or may contain one or more units of unsaturation, but which is not aromatic. Unless otherwise specified, aliphatic groups contain 1-12 carbon atoms. In some embodiments, aliphatic groups contain 1-6 carbon atoms. In some embodiments, aliphatic groups contain 1-4 carbon atoms, and in yet other embodiments, aliphatic groups contain 1-3 carbon atoms. Suitable aliphatic groups include, but are not limited to, linear or branched, alkyl, alkenyl, and alkynyl groups, and hybrids thereof such as (cycloalkyl)alkyl, (cycloalkenyl) alkyl or (cycloalkyl)alkenyl.

As used herein, the terms "heteroaliphatic" or "heteroaliphatic group", denote an optionally substituted hydrocarbon moiety having, in addition to carbon atoms, from one to five heteroatoms, that may be straight-chain (i.e., unbranched), branched, or cyclic ("heterocyclic") and may be completely saturated or may contain one or more units of unsaturation, but which is not aromatic. Unless otherwise specified, heteroaliphatic groups contain 1-6 carbon atoms wherein 1-3 carbon atoms are optionally and independently replaced with heteroatoms selected from oxygen, nitrogen and sulfur. In some embodiments, heteroaliphatic groups contain 1-4 carbon atoms, wherein 1-2 carbon atoms are optionally and independently replaced with heteroatoms selected from oxygen, nitrogen and sulfur. In yet other embodiments, heteroaliphatic groups contain 1-3 carbon atoms, wherein 1 carbon atom is optionally and independently replaced with a heteroatom selected from oxygen, nitrogen and sulfur.

Suitable heteroaliphatic groups include, but are not limited to, linear or branched, heteroalkyl, heteroalkenyl, and heteroalkynyl groups.

The term "halo" describes fluorine, chlorine, bromine or iodine substituent.

The term "halide" describes an anion of a halogen atom, namely F$^-$, Cl$^-$ Br$^-$ and I$^-$.

The term "haloalkyl" describes an alkyl group as defined above, further substituted by one or more halide.

The term "sulfate" describes a —O—S(=O)$_2$—OR' end group, as this term is defined hereinabove, or an —O—S(=O)$_2$—O— linking moiety, as these phrases are defined hereinabove, where R' is as defined hereinabove.

The term "thiosulfate" describes a —O—S(=S)(=O)—OR' end group or a —O—S(=S)(=O)—O— linking moiety, as these phrases are defined hereinabove, where R' is as defined hereinabove.

The term "sulfite" describes an —O—S(=O)—O—R' end group or a —O—S(=O)—O— group linking moiety, as these phrases are defined hereinabove, where R' is as defined hereinabove.

The term "thiosulfite" describes a —O—S(=S)—O—R' end group or an —O—S(=S)—O— group linking moiety, as these phrases are defined hereinabove, where R' is as defined hereinabove.

The term "sulfinate" or "sulfinyl" describes a —S(=O)—OR' end group or an —S(=O)—O— group linking moiety, as these phrases are defined hereinabove, where R' is as defined hereinabove.

The terms "solfoxide" or "sulfinyl" describe a —S(=O)R' end group or an —S(=O)— linking moiety, as these phrases are defined hereinabove, where R' is as defined hereinabove.

The term "sulfonate" or "sulfonyl" describes a —S(=O)$_2$—R' end group or an —S(=O)$_2$— linking moiety, as these phrases are defined hereinabove, where R' is as defined herein.

The term "S-sulfonamide" describes a —S(=O)$_2$—NR'R" end group or a —S(=O)$_2$—NR'— linking moiety, as these phrases are defined hereinabove, with R' and R" as defined herein.

The term "N-sulfonamide" describes an R'S(=O)$_2$—NR"— end group or a —S(=O)$_2$—NR'— linking moiety, as these phrases are defined hereinabove, where R' and R" are as defined herein.

The term "disulfide" refers to a —S—SR' end group or a —S—S— linking moiety, as these phrases are defined hereinabove, where R' is as defined herein.

The term "phosphate" describes an —O—P(=O)$_2$(OR') end or reactive group or a —O—P(=O)$_2$(O)— linking moiety, as these phrases are defined hereinabove, with R' as defined herein.

The term "phosphonate" describes a —P(=O)(OR')(OR") end or reactive group or a —P(=O)(OR')(O)— linking moiety, as these phrases are defined hereinabove, with R' and R" as defined herein.

The term "thiophosphonate" describes a —P(=S)(OR')(OR") end group or a —P(=S)(OR')(O)— linking moiety, as these phrases are defined hereinabove, with R' and R" as defined herein.

The term "carbonyl" or "carbonate" as used herein, describes a —C(=O)—R' end group or a —C(=O)— linking moiety, as these phrases are defined hereinabove, with R' as defined herein.

The term "thiocarbonyl" as used herein, describes a —C(=S)—R' end group or a —C(=S)— linking moiety, as these phrases are defined hereinabove, with R' as defined herein.

The term "oxo" as used herein, described a =O end group.

The term "thiooxo" as used herein, described a =S end group.

The term "oxime" describes a =N—OH end group or a =N—O— linking moiety, as these phrases are defined hereinabove.

The term "hydroxyl" describes a —OH group.

As used herein, the term "aldehyde" refers to an —C(=O)—H group.

The term "acyl halide" describes a —(C=O)R'" group wherein R'" is halo, as defined hereinabove.

The term "alkoxy" as used herein describes an —O-alkyl, an —O-cycloalkyl, as defined hereinabove. The ether group —O— is also a possible linking moiety.

The term "aryloxy" describes both an —O-aryl and an —O-heteroaryl group, as defined herein.

The term "disulfide" as used herein describes an —S—S— linking moiety, which in some cases forms between two thiohydroxyl groups.

The terms "thio", "sulfhydryl" or "thiohydroxyl" as used herein describe an —SH group.

The term "thioalkoxy" or "thioether" describes both a —S-alkyl group, and a —S-cycloalkyl group, as defined herein. The thioether group —S— is also a possible linking moiety.

The term "thioaryloxy" describes both a —S-aryl and a —S-heteroaryl group, as defined herein. The thioarylether group —S-aryl- is also a possible linking moiety.

The term "cyano" or "nitrile" describes a —C≡N group.

The term "isocyanate" describes an —N=C=O group.

The term "nitro" describes an —NO$_2$ group.

The term "carboxylate" or "ester", as used herein encompasses C-carboxylate and O-carboxylate.

The term "C-carboxylate" describes a —C(=O)—OR' end group or a —C(=O)—O— linking moiety, as these phrases are defined hereinabove, where R' is as defined herein.

The term "O-carboxylate" describes a —OC(=O)R' end group or a —OC(=O)— linking moiety, as these phrases are defined hereinabove, where R' is as defined herein. The term "thiocarboxylate" as used herein encompasses "C-thiocarboxylate and O-thiocarboxylate.

The term "C-thiocarboxylate" describes a —C(=S)—OR' end group or a —C(=S)—O— linking moiety, as these phrases are defined hereinabove, where R' is as defined herein.

The term "O-thiocarboxylate" describes a —OC(=S)R' end group or a —OC(=S)— linking moiety, as these phrases are defined hereinabove, where R' is as defined herein.

The term "carbamate" as used herein encompasses N-carbamate and O-carbamate.

The term "N-carbamate" describes an R"OC(=O)—NR'— end group or a —OC(=O)—NR'— linking moiety, as these phrases are defined hereinabove, with R' and R" as defined herein.

The term "O-carbamate" describes an —OC(=O)—NR'R" end group or an —OC(=O)—NR'— linking moiety, as these phrases are defined hereinabove, with R' and R" as defined herein.

The term "thiocarbamate" as used herein encompasses N-thiocarbamate and O-thiocarbamate.

The term "O-thiocarbamate" describes a —OC(=S)—NR'R" end group or a —OC(=S)—NR'— linking moiety, as these phrases are defined hereinabove, with R' and R" as defined herein.

The term "N-thiocarbamate" describes an R"OC(=S)NR'— end group or a —OC(=S)NR'— linking moiety, as these phrases are defined hereinabove, with R' and R" as defined herein.

The term "dithiocarbamate" as used herein encompasses N-dithiocarbamate and S-dithiocarbamate.

The term "S-dithiocarbamate" describes a —SC(=S)—NR'R" end group or a —SC(=S)NR'— linking moiety, as these phrases are defined hereinabove, with R' and R" as defined herein.

The term "N-dithiocarbamate" describes an R"SC(=S)NR'— end group or a —SC(=S)NR'— linking moiety, as these phrases are defined hereinabove, with R' and R" as defined herein.

The term "urea", which is also referred to herein as "ureido", describes a —NR'C(=O)—NR"R'" end group or a —NR'C(=O)—NR"— linking moiety, as these phrases are defined hereinabove, where R' and R" are as defined herein and R'" is as defined herein for R' and R".

The term "thiourea", which is also referred to herein as "thioureido", describes a —NR'—C(=S)—NR"R'" end group or a —NR'—C(=S)—NR"— linking moiety, with R', R" and R'" as defined herein.

The term "amide" as used herein encompasses C-amide and N-amide.

The term "C-amide" describes a —C(=O)—NR'R" end group or a —C(=O)—NR'— linking moiety, as these phrases are defined hereinabove, where R' and R" are as defined herein.

The term "N-amide" describes a R'C(=O)—NR"— end group or a R'C(=O)—N— linking moiety, as these phrases are defined hereinabove, where R' and R" are as defined herein.

The term "imine", which is also referred to in the art interchangeably as "Schiff-base", describes a —N=CR'— linking moiety, with R' as defined herein or hydrogen. As is well known in the art, Schiff bases are typically formed by reacting an aldehyde or a ketone and an amine-containing moiety such as amine, hydrazine, hydrazide and the like, as these terms are defined herein. The term "aldimine" refers to a —CH=N— imine which is derived from an aldehyde. The term "ketimine" refers to a —CR'=N— imine which is derived from a ketone.

The term "hydrazone" refers to a —R'C=N—NR"— linking moiety, wherein R' and R" are as defined herein.

The term "semicarbazone" refers to a linking moiety which forms in a condensation reaction between an aldehyde or ketone and semicarbazide. A semicarbazone linking moiety stemming from a ketone is a —R'C=NNR"C(=O)NR'"—, and a linking moiety stemming from an aldehyde is a —CR'=NNR"C(=O)NR'"—, wherein R' and R" are as defined herein and R'" or as defined for R'.

As used herein, the term "lactone" refers to a cyclic ester, namely the intra-condensation product of an alcohol group —OH and a carboxylic acid group —COOH in the same molecule.

As used herein, the term "lactam" refers to a cyclic amide, as this term is defined herein. A lactam with two carbon atoms beside the carbonyl and four ring atoms in total is referred to as a β-lactam, a lactam with three carbon atoms beside the carbonyl and five ring atoms in total is referred to as a γ-lactam, a lactam with four carbon atoms beside the carbonyl and six ring atoms in total is referred to as a δ-lactam, and so on.

The term "guanyl" describes a R'R"NC(=N)— end group or a —R'NC(=N)— linking moiety, as these phrases are defined hereinabove, where R' and R" are as defined herein.

The term "guanidine" describes a —R'NC(=N)—NR"R'" end group or a —R'NC(=N)—NR"— linking moiety, as these phrases are defined hereinabove, where R', R" and R'" are as defined herein.

The term "hydrazine" describes a —NR'—NR"R'" end group or a —NR'—NR"— linking moiety, as these phrases are defined hereinabove, with R', R", and R'" as defined herein.

As used herein, the term "hydrazide" describes a —C(=O)—NR'—NR"R'" end group or a —C(=O)—NR'—NR"— linking moiety, as these phrases are defined hereinabove, where R', R" and R'" are as defined herein.

The term "hydroxylamine", as used herein, refers to either a —NHOH group or a —ONH$_2$.

As used herein, the terms "azo" or "diazo" describe a —N=N—R' end group or a —N=N— linking moiety, as these phrases are defined hereinabove, where R' is as defined herein.

As used herein, the term "azido" described a —N=N$^+$=N$^-$ (—N$_3$) end group.

The term "triazine" refers to a heterocyclic ring, analogous to the six-membered benzene ring but with three carbons replaced by nitrogen atoms. The three isomers of triazine are distinguished from each other by the positions of their nitrogen atoms, and are referred to as 1,2,3-triazine, 1,2,4-triazine, and 1,3,5-triazine. Other aromatic nitrogen heterocycles include pyridines with 1 ring nitrogen atom, diazines with 2 nitrogen atoms in the ring and tetrazines with 4 ring nitrogen atoms.

The term "triazole" refers to either one of a pair of isomeric chemical compounds with molecular formula $C_2H_3N_3$, having a five-membered ring of two carbon atoms and three nitrogen atoms, namely 1,2,3-triazoles and 1,2,4-triazoles.

The term "aziridine", as used herein, refers to a reactive group which is a three membered heterocycle with one amine group and two methylene groups, having a molecular formula of —$C_2H_3NH$.

As used herein, the term "thiohydrazide" describes a —C(=S)—NR'—NR"R'" end group or a —C(=S)—NR'—NR"— linking moiety, as these phrases are defined hereinabove, where R', R" and R'" are as defined herein.

As used herein, the term "methyleneamine" describes an —NR'—CH$_2$—CH=CR"R'" end group or a —NR'—CH$_2$—CH=CR"— linking moiety, as these phrases are defined hereinabove, where R', R" and R'" are as defined herein.

The term "diene", as used herein, refers to a —CR'=CR"—CR'"=CR""— group, wherein R' as defined hereinabove, and R", R'" and R"" are as defined for R'.

The term "dienophile", as used herein, refers to a reactive group that reacts with a diene, typically in a Diels-Alder reaction mechanism, hence a dienophile is typically a double bond or an alkenyl.

The term "epoxy", as used herein, refers to a reactive group which is a three membered heterocycle with one oxygen and two methylene groups, having a molecular formula of —$C_2H_3O$.

The phrase "covalent bond", as used herein, refers to one or more pairs of electrons that are shared between atoms in a form of chemical bonding.

According to some embodiments of the present invention, some linking moieties result from a reaction between two reactive groups. Alternatively, a desired linking moiety is first generated and a bioactive agent and/or a spacer moiety are attached thereto.

Linking Moiety Lability:

According to some embodiments of the present invention, the linking moiety is cleavable at physiological conditions, namely the linking moiety disintegrates during of exposure to the physiological environment in the bodily site. Such linking moiety is referred to herein a "biodegradable" or "biocleavable". Biocleavable linking moieties offer the advantage of the conjugate being cleaved into two bioactive agents at the targeted bodily site. In the context of some embodiments of the present invention, biocleavable linking moieties are selected so as to break and release the conjugated bioactive agents at certain conditions, referred to herein as "drug-releasing conditions" or "cleavage conditions".

Thus, according to some embodiments of the present invention, the linking moiety that link between the residues of the first and second bioactive agents is a biodegradable or biocleavable linking moiety. According to some embodiments of the present invention, some of the linking moieties are biocleavable-linking moieties. As used herein, the terms "biocleavable" and "biodegradable" are used interchangeably to refer to moieties that degrade (i.e., break and/or lose at least some of their covalent structure) under physiological or endosomal conditions. Biodegradable moieties are not necessarily spontaneously, thermally or hydrolytically degradable and may require enzymatic activity to break.

As used herein, the terms "biocleavable moiety" or "biodegradable moiety" describe a chemical moiety, which undergoes cleavage in a biological system such as, for example, the digestive system of an organism or a metabolic system in a living cell.

In some embodiments, biocleavable linking moieties are selected according to their susceptibility to certain enzymes that are likely to be present at the targeted bodily site or at any other bodily site where cleavage is intended, thereby defining the cleavage conditions.

Representative examples of biocleavable moieties include, without limitation, amides, carboxylates (esters), carbamates, phosphates, hydrazides, thiohydrazides, disulfides, epoxides, peroxo and methyleneamines. Such moieties are typically subjected to enzymatic cleavages in a biological system, by enzymes such as, for example, hydrolases, amidases, kinases, peptidases, phospholipases, lipases, proteases, esterases, epoxide hydrolases, nitrilases, glycosidases and the like.

For example, hydrolases (EC number beginning with 3) catalyze hydrolysis of a chemical bond according to the general reaction scheme A-B+$H_2O$→A-OH+B—H. Ester bonds are cleaved by sub-group of hydrolases known as esterases (EC number beginning with 3.1), which include nucleases, phosphodiesterases, lipases and phosphatases. Hydrolases having an EC number beginning with 3.4 are peptidases, which act on peptide bonds.

Additional information pertaining to enzymes, enzymatic reactions, and enzyme-linking moiety correlations can be found in various publically accessible sources, such as Bairoch A., "The ENZYME database in 2000", Nucleic Acids Res, 2000, 28, pp. 304-305, and "Drug Delivery in Oncology: From Basic Research to Cancer Therapy", Kratz, F., Senter, P. and Steinhagen, H. Editors, 2011, Volume 1, Section 5.4.2: "Enzymatic Cleavage", pages 143-145.

According to some embodiments of the present invention, the conjugate is characterized by a biocleavable moiety that undergoes cleavage without leaving any molecular remnants (atoms, moieties, functional groups), namely that the re-generated bioactive agents are identical in chemical structure to the original bioactive agents.

Conjugate Preparation:

According to some embodiments, each of the first bioactive agent and the second bioactive agent that are conjugated to form the presently provided conjugates, exhibit a first functional group and a second functional group, respectively, and the linking moiety is a biodegradable moiety that is formed by coupling the first functional group and the second functional group. Non-limiting examples of anticancer bioactive agents that can form the conjugate, according to some embodiments of the invention, are presented hereinbelow according to the reactive functional group exhibited in their structure.

Amine-Containing Anticancer Drugs:

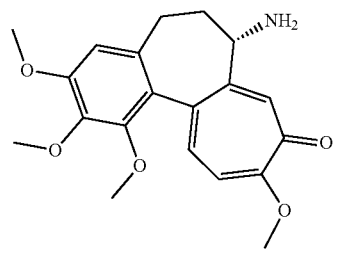

Deacetyl colchicine

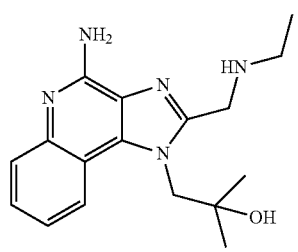

gardiquimod

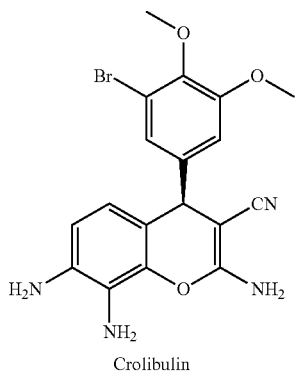

Crolibulin

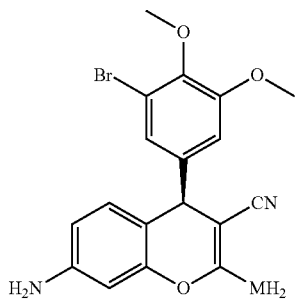

Semi crolibulin

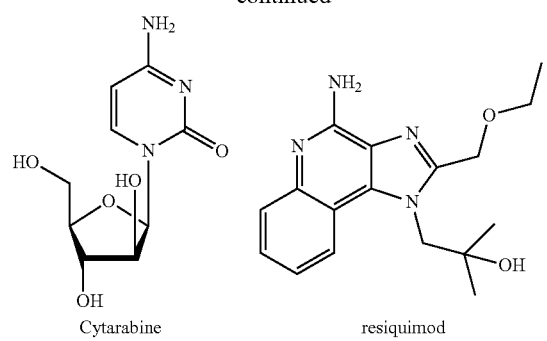
Cytarabine   resiquimod
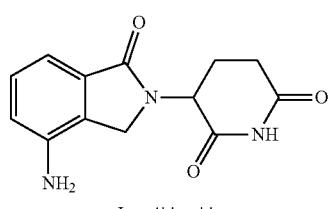
Lenalidomide
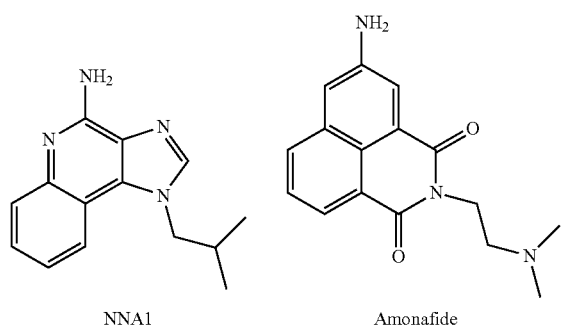
NNA1   Amonafide
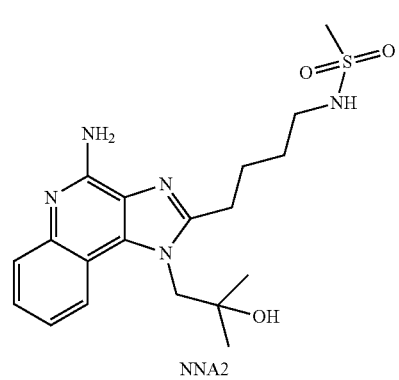
NNA2
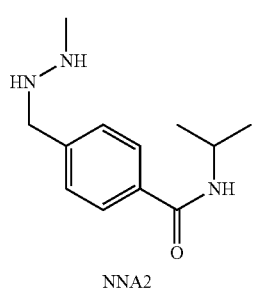
NNA2
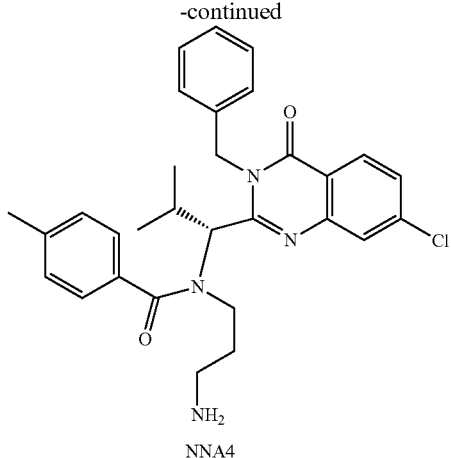
NNA4
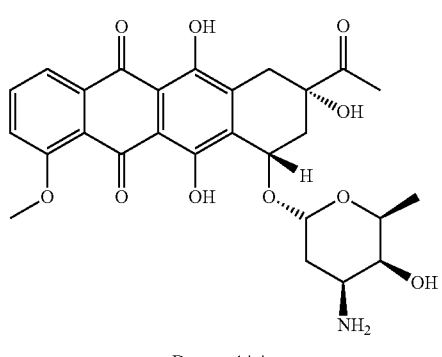
Daunorubicin
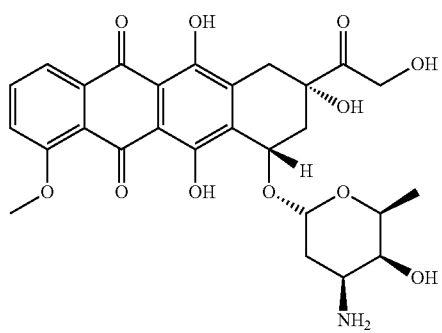
Doxorubicin
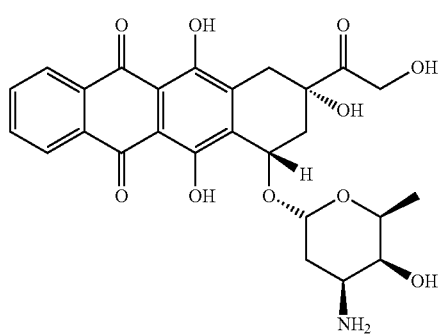
Idarubicin 23
-continued
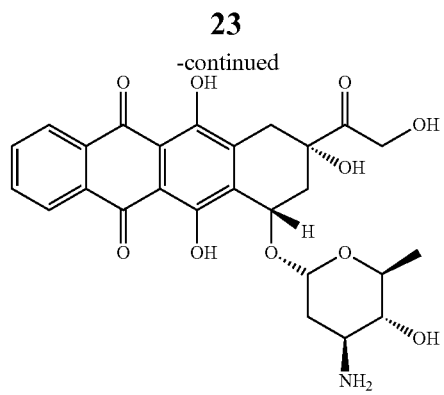
Epirubicin
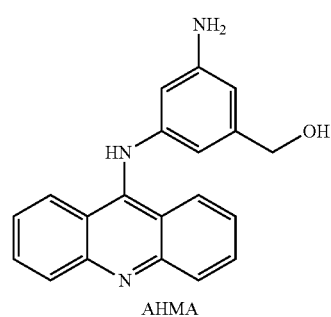
AHMA
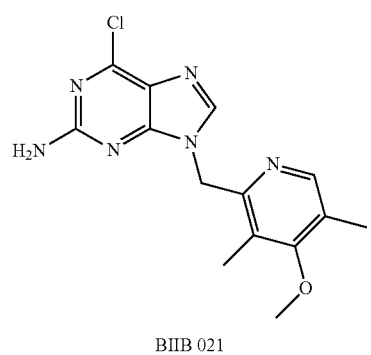
BIIB 021
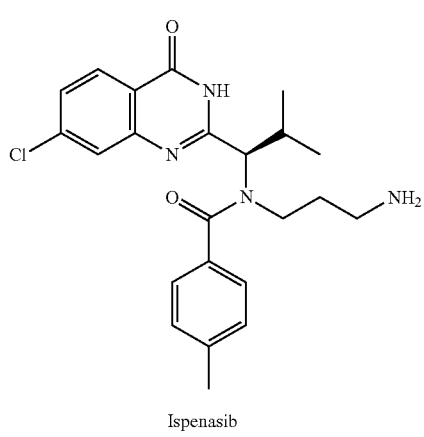
Ispenasib
24
-continued
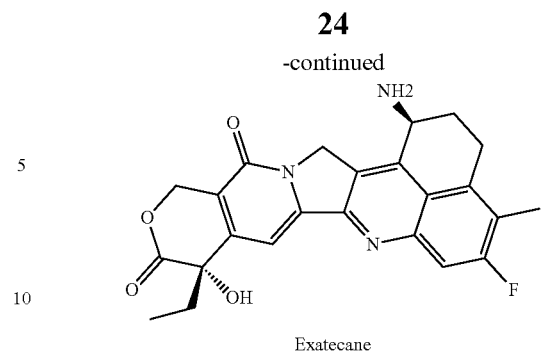
Exatecane
Carboxyl-Containing Anticancer Drugs:
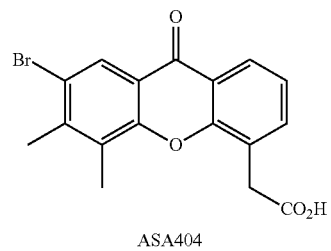
ASA404
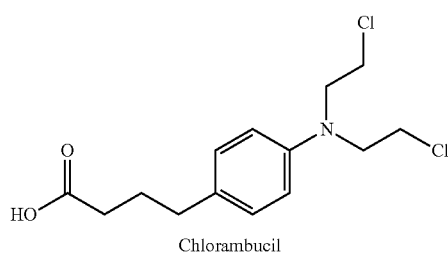
Chlorambucil
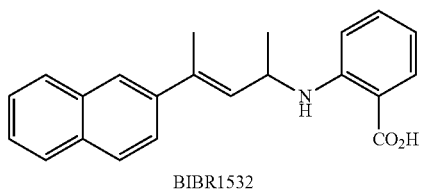
BIBR1532
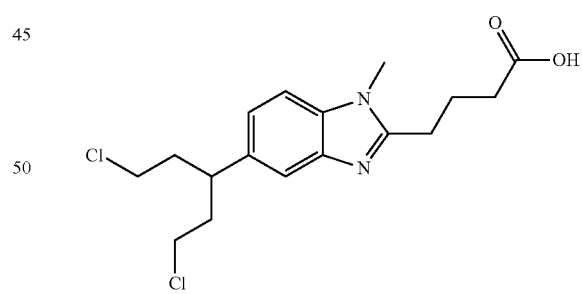
Bendamustin
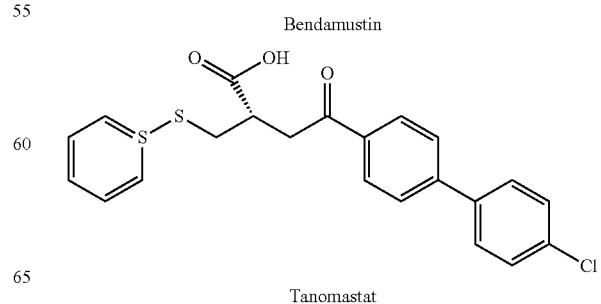
Tanomastat

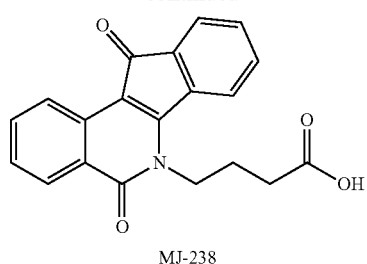
MJ-238
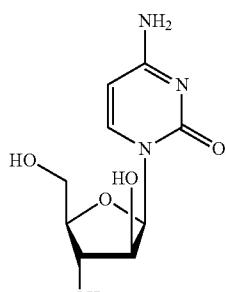
Cytarabine
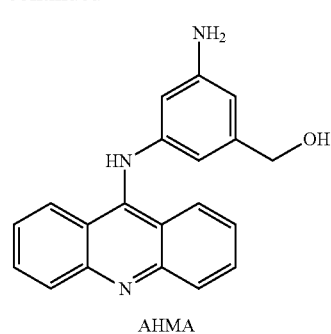
AHMA
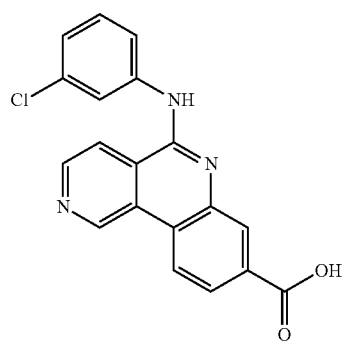
PK CK2 ATP competitiveinhibtor
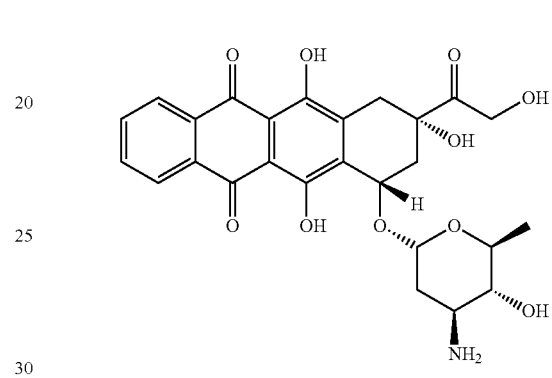
Epirubicin
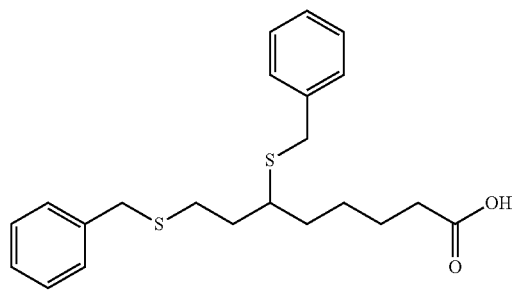
PI-603
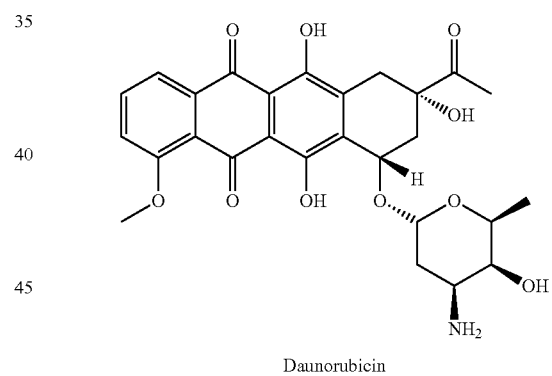
Daunorubicin
Hydroxyl-Containing Anticancer Drugs:
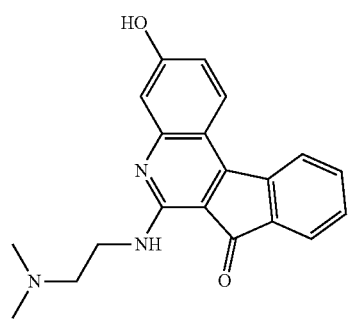
TAS 103
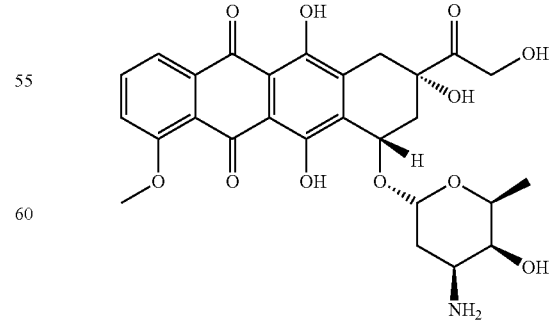
Doxorubicin 27
-continued
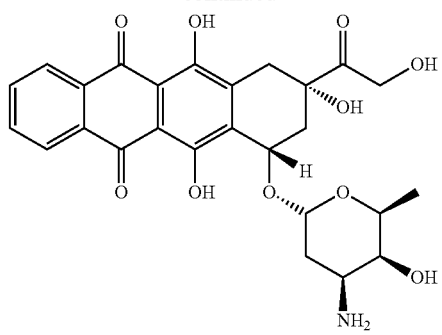
Idarubicin
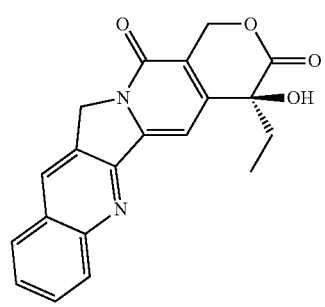
Camptothecin (CPT)
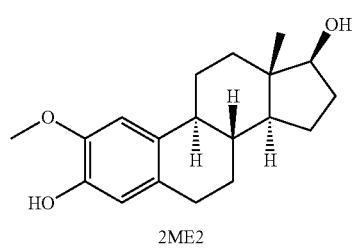
2ME2
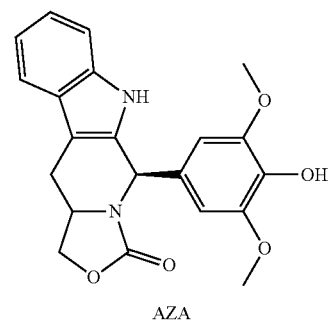
AZA
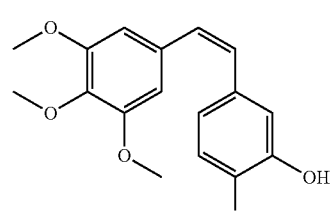
Combretastatin
28
-continued
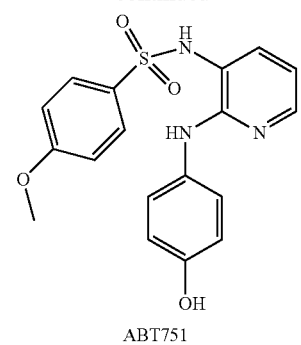
ABT751
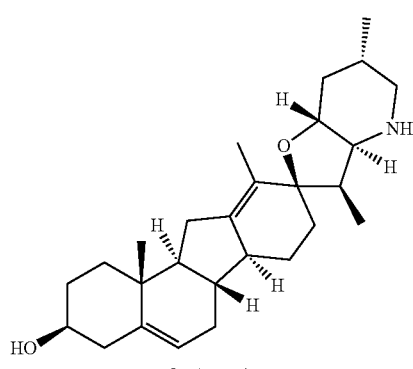
Cyclopamine
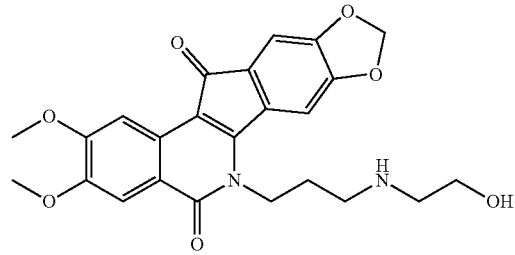
MJ-III-65
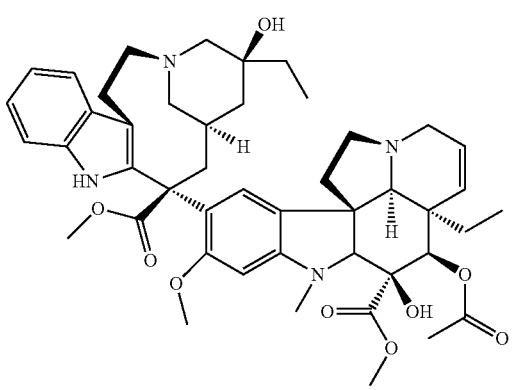
Vinblastine
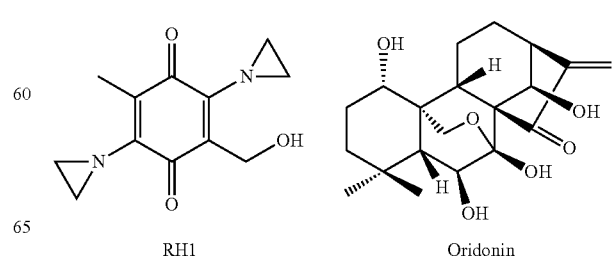
RH1              Oridonin

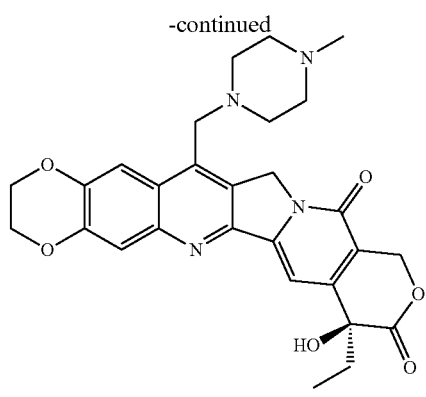

Lurtotecane

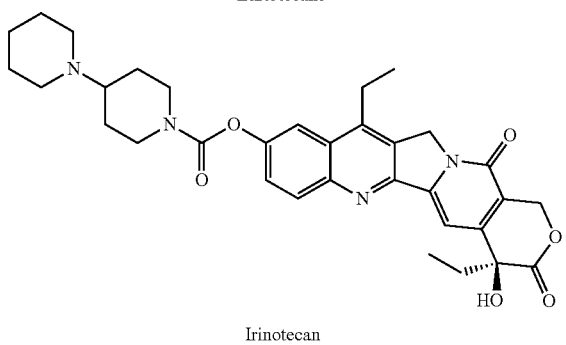

Irinotecan

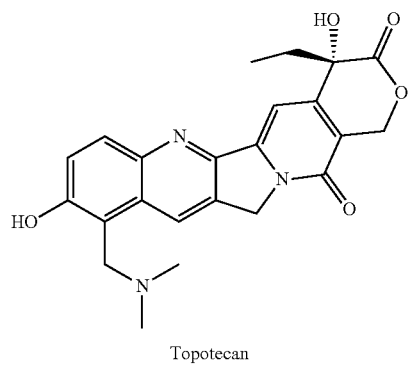

Topotecan

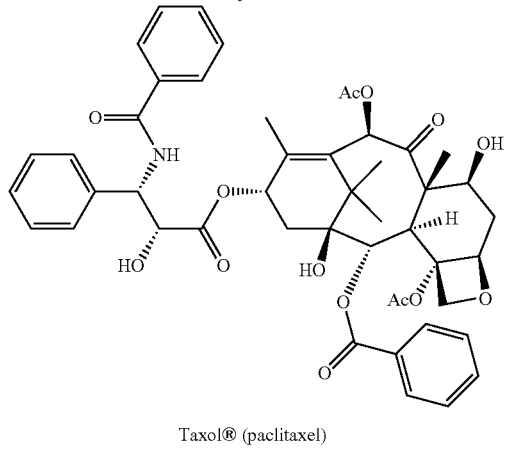

Taxol® (paclitaxel)

The preparation of the conjugates presented herein is based on coupling reactions that forms a biocleavable linking moiety from reactive functional groups present in each of the first and second drugs. Exemplary coupling reactions include, but are not limited to coupling amine and carboxyl to form amide, coupling hydroxyl and carboxyl to form ester, and coupling ester and amine to form carbamate, as illustrated in Scheme 1 below.

Scheme 1

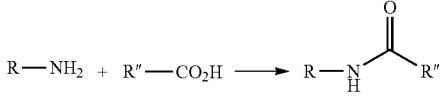

Amide-forming coupling reaction

Ester-forming coupling reaction

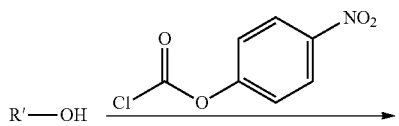

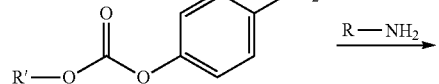

Carbamate-forming coupling reaction

As can be seen in Scheme 1, the functional groups that are coupled together to form the linking moiety can form a part of the bioactive agent, or another functional group on the bioactive agent can be modified to become one of the functional groups that are coupled together to form the linking moiety (see, for example, the formation of a carbamate linking moiety in Scheme 1).

Examples of Conjugates

Table 1 present a list of exemplary conjugates, according to some embodiments of the present invention, listed by their corresponding first and second anticancer bioactive agents and the type of the biocleavable linking moiety bonding therebetween. The conjugates, referred to herein as Chimera (exemplary Chimera 356-363) are constructed from residues of the first anticancer bioactive agent and the second anticancer bioactive agent, linked together by the biocleavable linking moiety which is formed by coupling two functional groups, each forming a part of each of the drugs.

TABLE 1

| 1st bioactive agent | 2nd bioactive agent | Biocleavable linking moiety | Scheme of formation and biodegradation |
| --- | --- | --- | --- |
| Camptothecin | Chlorambucil | ester | Scheme 2 |
| (S)-4-ethyl-3,14-dioxo-3,4,12,14-tetrahydro-1H-pyrano[3',4':6,7]indolizino[1,2-b]quinolin-4-yl 4-(4-(bis(2-chloroethyl)amino)phenyl)butanoate (Chimera 356) | | | |
| Camptothecin | Colchicine | carbamate | Scheme 3 |
| (S)-4-ethyl-3,14-dioxo-3,4,12,14-tetrahydro-1H-pyrano[3',4':6,7]indolizino[1,2-b]quinolin-4-yl ((S)-1,2,3,10-tetramethoxy-9-oxo-5,6,7,9-tetrahydrobenzo[a]heptalen-7-yl)carbamate (Chimera 357) | | | |
| Amonafide | Chlorambucil | amide | Scheme 4 |
| 4-(4-(bis(2-chloroethyl)amino)phenyl)-N-(2-(2-(dimethylamino)ethyl)-1,3-dioxo-2,3-dihydro-1H-benzo[de]isoquinolin-5-yl)butanamide (Chimera 358) | | | |
| Amonafide | Camptothecin | carbamate | Scheme 5 |
| (S)-4-ethyl-3,14-dioxo-3,4,12,14-tetrahydro-1H-pyrano[3',4':6,7]indolizino[1,2-b]quinolin-4-yl (2-(2-(dimethylamino)ethyl)-1,3-dioxo-2,3-dihydro-1H-benzo[de]isoquinolin-5-yl)carbamate (Chimera 359) | | | |
| Cytarabine | Chlorambucil | amide | Scheme 6 |
| 4-(4-(bis(2-chloroethyl)amino)phenyl)-N-(1-(3,4-dihydroxy-5-(hydroxymethyl)tetrahydrofuran-2-yl)-2-oxo-1,2-dihydropyrimidin-4-yl)butanamide (Chimera 360) | | | |
| Doxorubicin | Chlorambucil | amide | Scheme 7 |
| 4-(4-(bis(2-chloroethyl)amino)phenyl)-N-((2S,3S,4S,6R)-3-hydroxy-2-methyl-6-(((1S,3S)-3,5,12-trihydroxy-3-(2-hydroxyacetyl)-10-methoxy-6,11-dioxo-1,2,3,4,6,11-hexahydrotetracen-1-yl)oxy)tetrahydro-2H-pyran-4-yl)butanamide (Chimera 361) | | | |
| Doxorubicin | Camptothecin | carbamate | Scheme 8 |
| (S)-4-ethyl-3,14-dioxo-3,4,12,14-tetrahydro-1H-pyrano[3',4':6,7]indolizino[1,2-b]quinolin-4-yl ((2S,3S,4S,6R)-3-hydroxy-2-methyl-6-(((1S,3S)-3,5,12-trihydroxy-3-(2-hydroxyacetyl)-10-methoxy-6,11-dioxo-1,2,3,4,6,11-hexahydrotetracen-1-yl)oxy)tetrahydro-2H-pyran-4-yl)carbamate (Chimera 362) | | | |
| Cytarabine | Camptothecin | carbamate | Scheme 9 |
| (S)-4-ethyl-3,14-dioxo-3,4,12,14-tetrahydro-1H-pyrano[3',4':6,7]indolizino[1,2-b]quinolin-4-yl (1-(3,4-dihydroxy-5-(hydroxymethyl)tetrahydrofuran-2-yl)-2-oxo-1,2-dihydropyrimidin-4-yl)carbamate (Chimera 363) | | | |

The schemes below present the same non-limiting examples of conjugates as presented in Table 1 hereinabove, while illustrating the coupling reactions that afford the conjugates. The schemes further present the result of the biocleavage of the liming moiety including by products.

Scheme 2

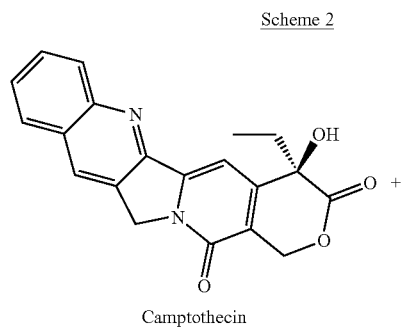

Camptothecin

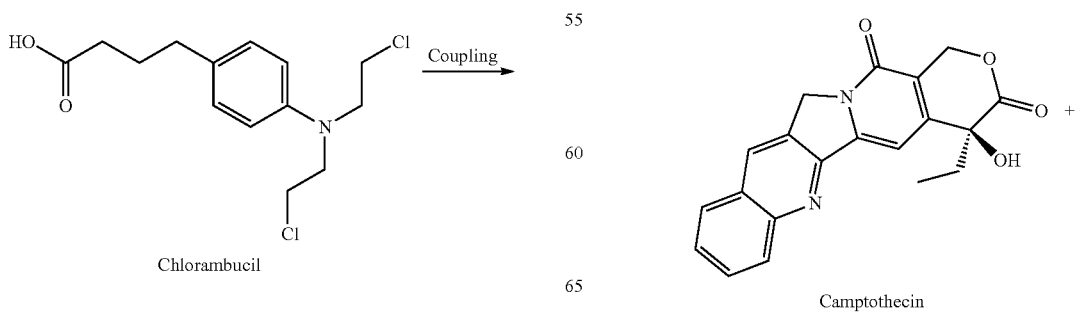

Chlorambucil

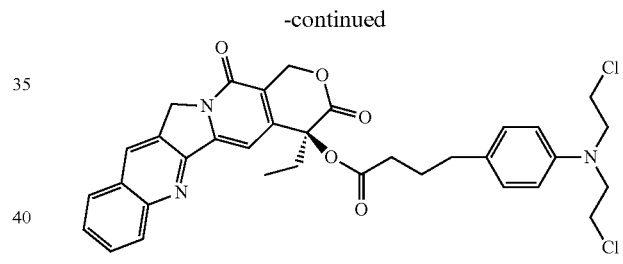

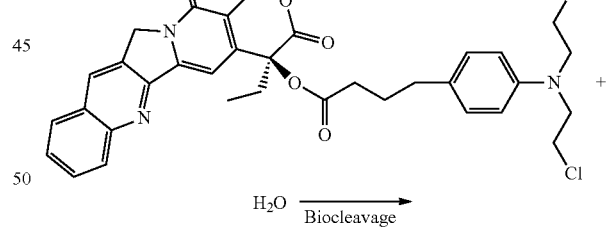

Camptothecin

33
-continued
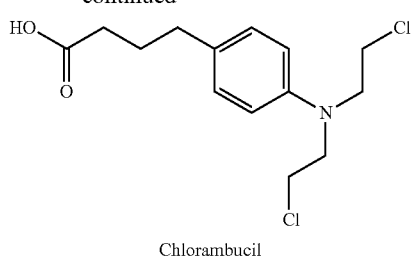
Chlorambucil
Scheme 3
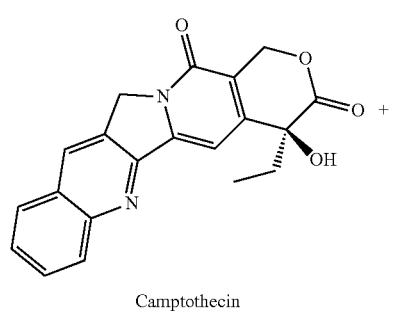
Camptothecin
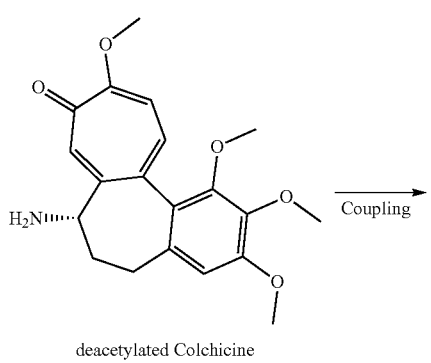
deacetylated Colchicine
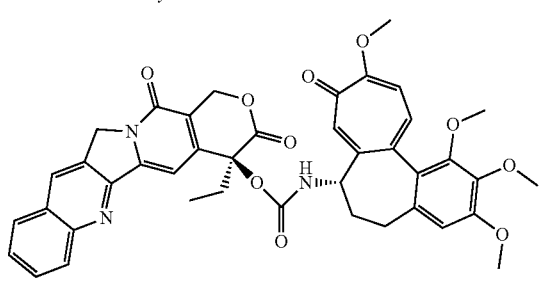
$\xrightarrow{\text{H}_2\text{O}}{\text{Biocleavage}}$
34
-continued
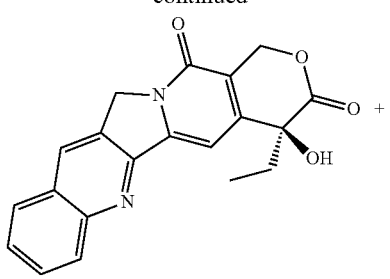
Camptothecin
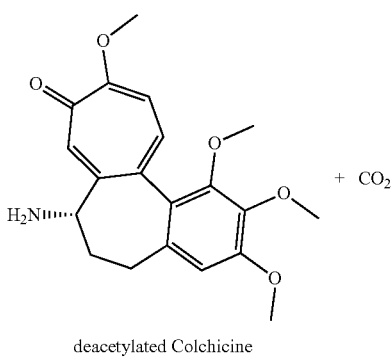
deacetylated Colchicine   $+ \text{CO}_2$
Scheme 4
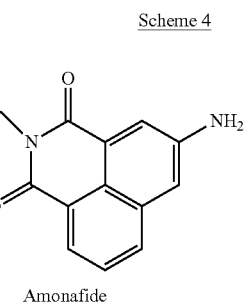
Amonafide
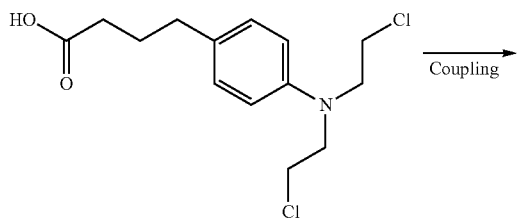
Chlorambucil $\xrightarrow{\text{Coupling}}$
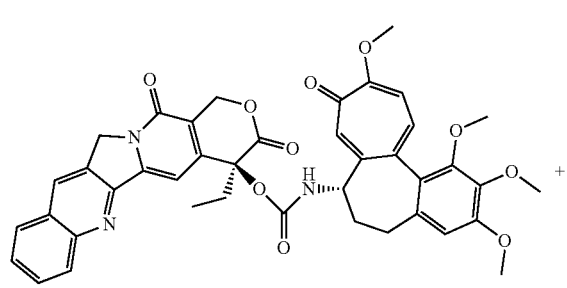
Chimera 358

35
-continued
36
-continued
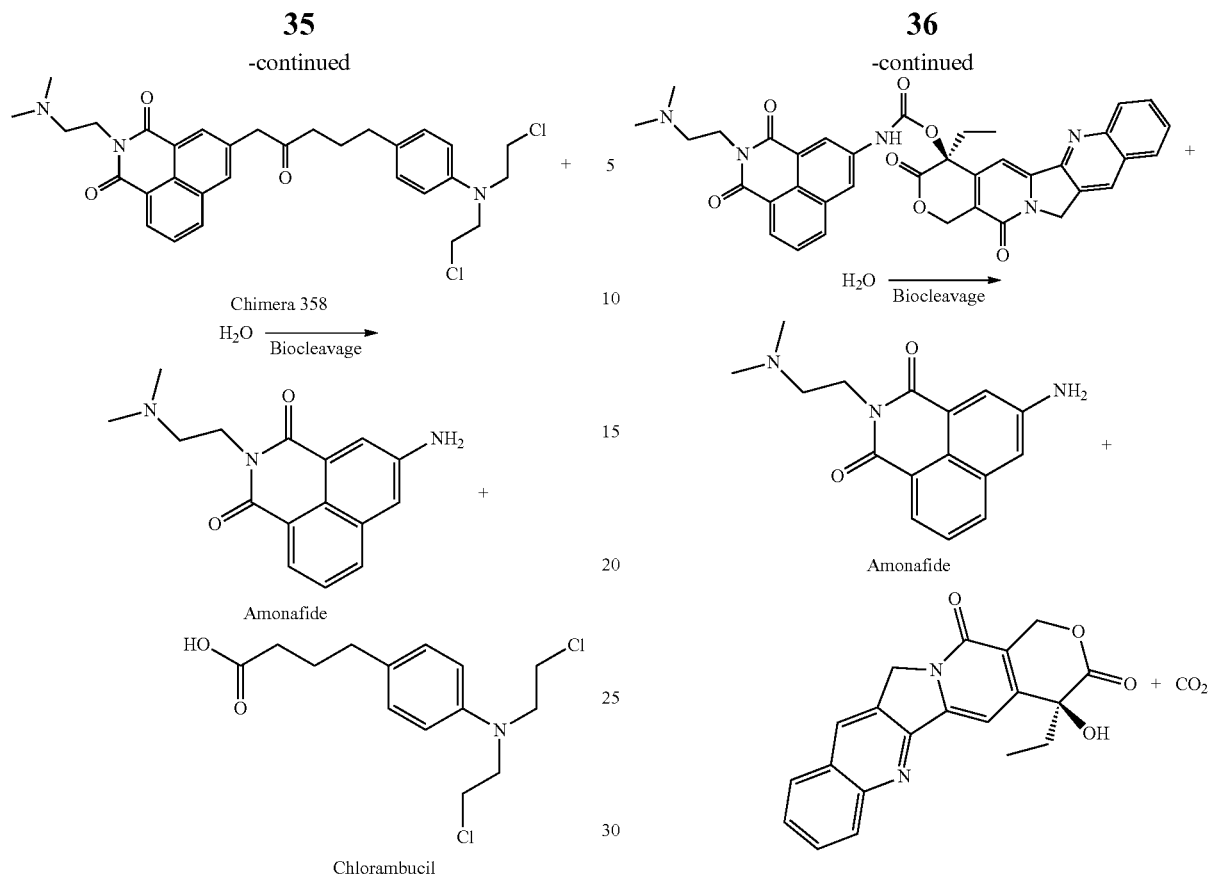
Scheme 5
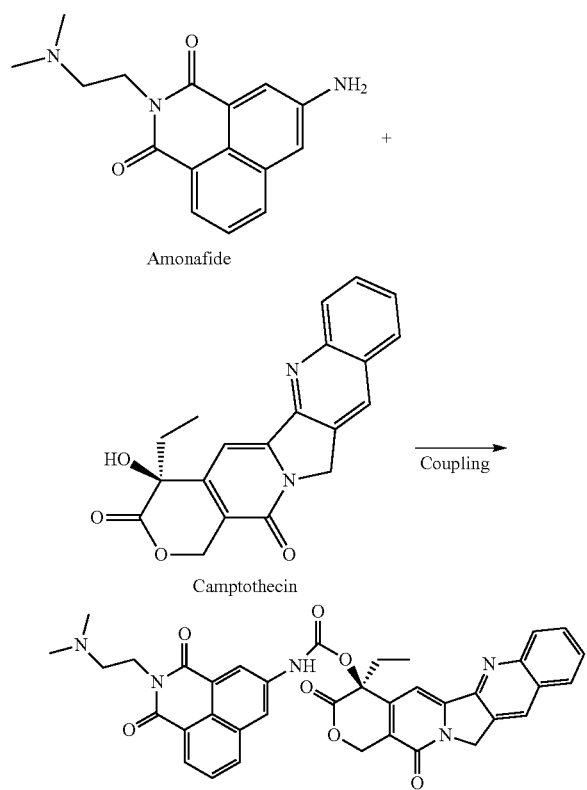
Scheme 6

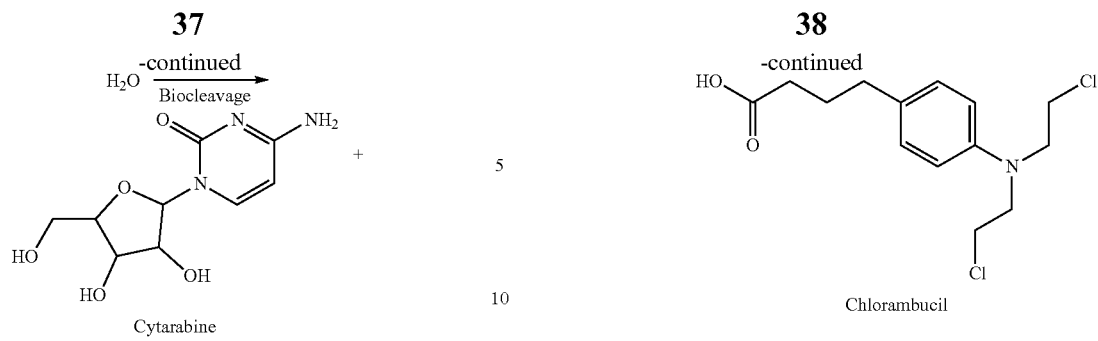
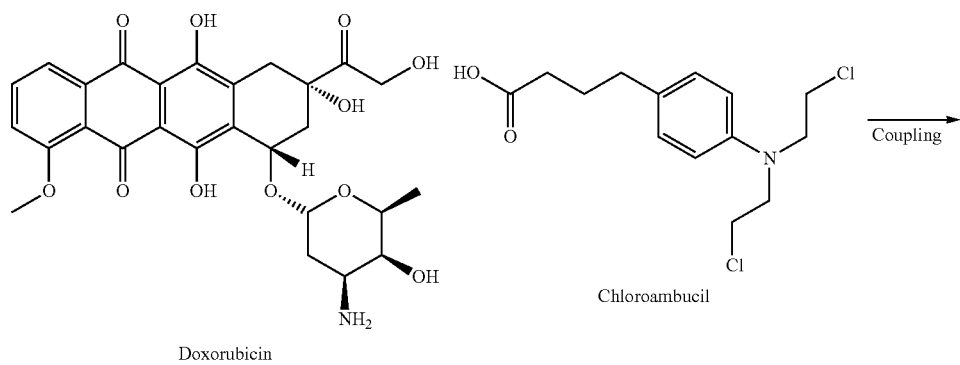
Scheme 7
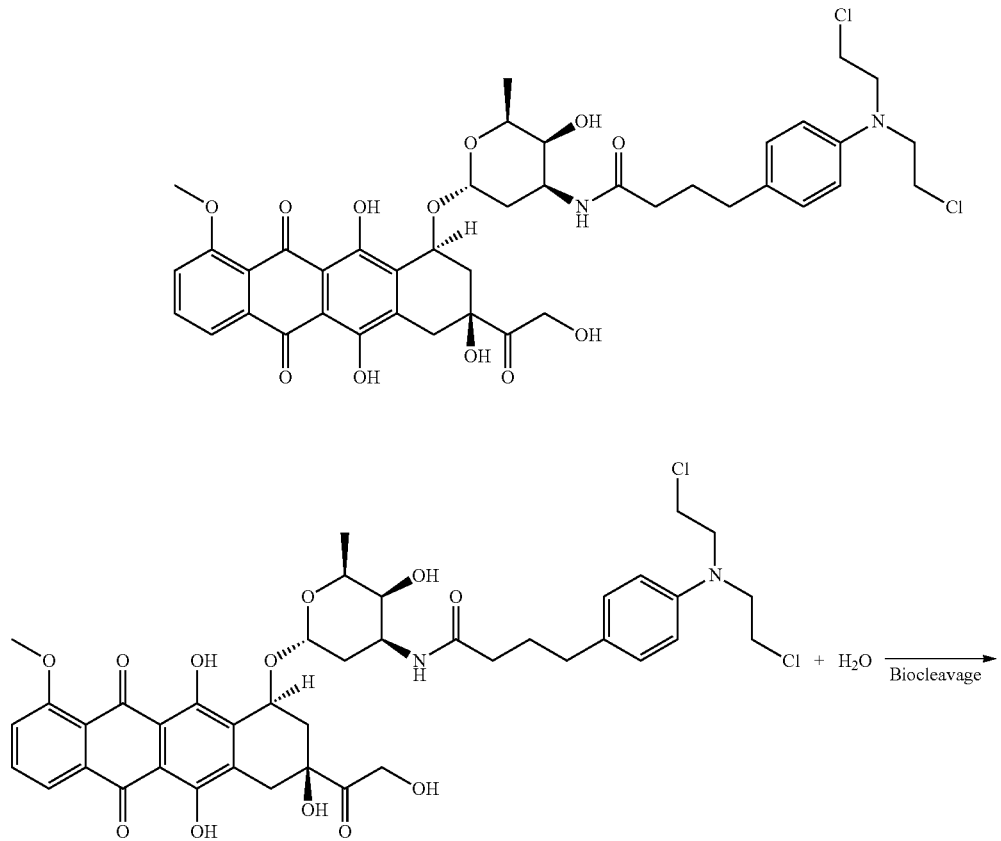

39
-continued
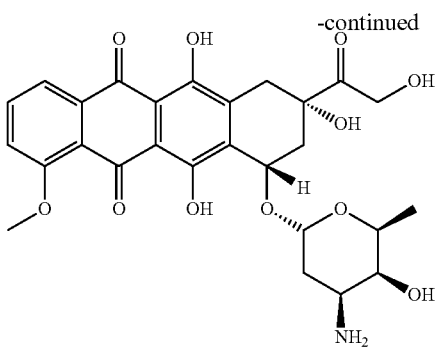
Doxorubicin
40
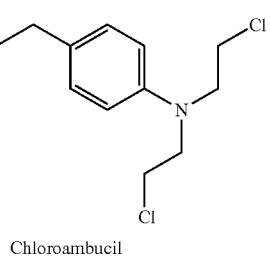
Chloroambucil
Scheme 8
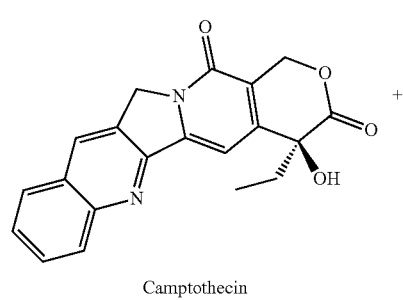
Camptothecin
+
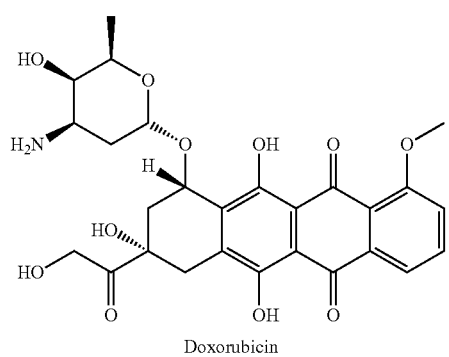
Doxorubicin
Coupling →
-continued
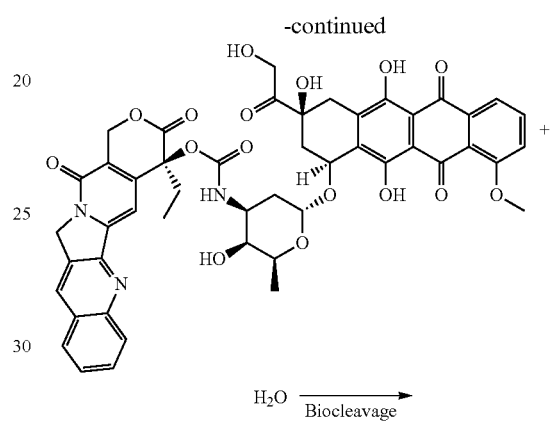
$H_2O$ $\xrightarrow{\text{Biocleavage}}$
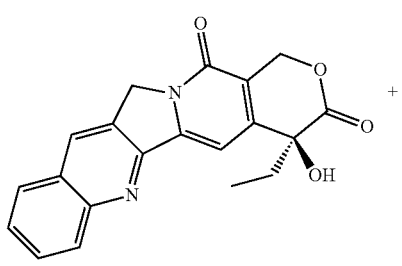
Camptothecin
+
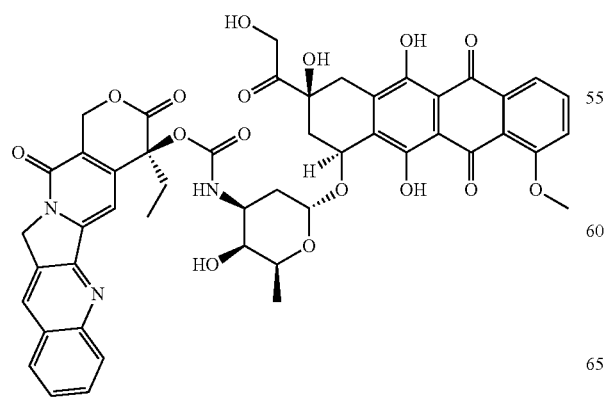
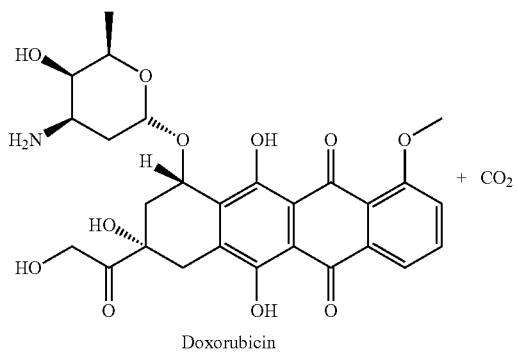 + $CO_2$
Doxorubicin Scheme 9

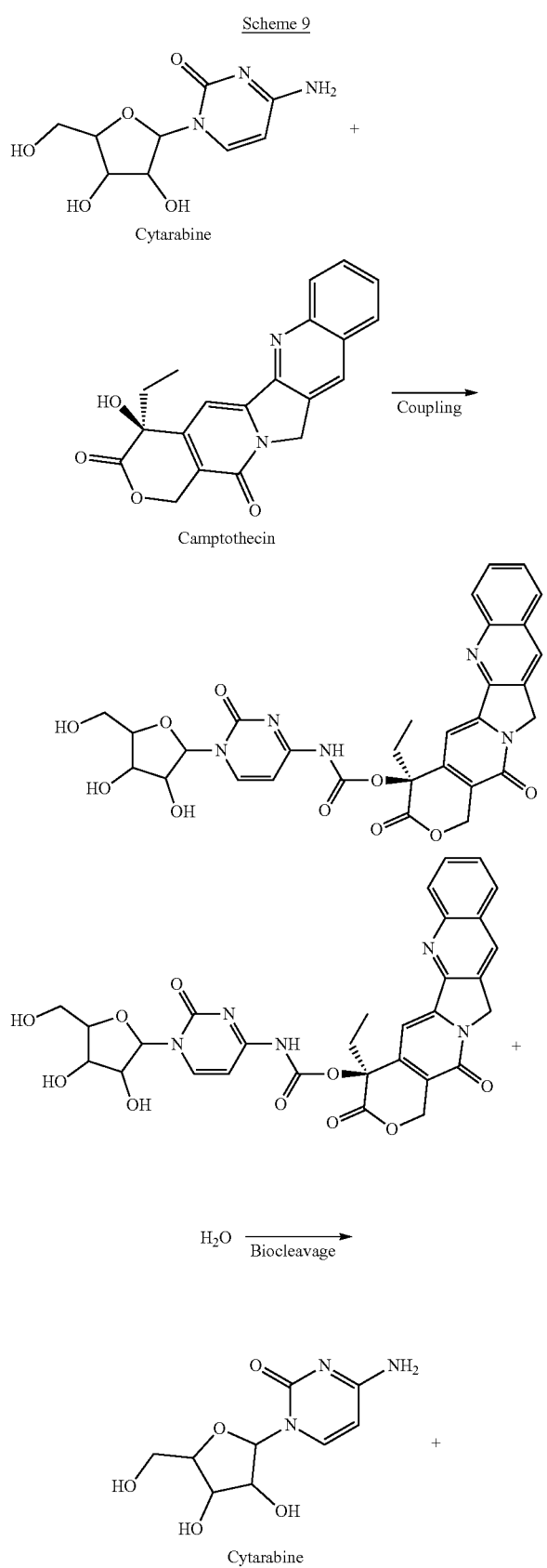

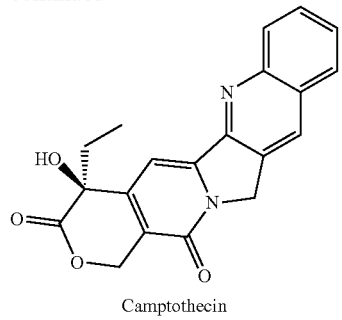
Camptothecin

Mechanism of Therapeutic Activity:

According to some embodiments, the conjugate carries two types of drugs which differ than one another at least by their structure, and more preferably by their mechanism of biological activity. Without being bound by any particular theory, it is assumed that a conjugate that can deliver two bioactive agents (a first anticancer bioactive agent and a second anticancer bioactive agent) that act by two different mechanism of biological activity (a first therapeutic activity and a second therapeutic activity, respectively), would provide superior therapeutic effects, particularly when attempting to affect a resistant cellular system, such as multi-drug resistant cancerous cells.

In the context of embodiments of the present invention, the phrase "mechanism of biological activity" refers to the biochemical mechanism by which a drug exerts its beneficial therapeutic effect. Example of mechanisms of biological activity include cell membrane disruption, destabilization and permeabilization, disruption of cell metabolism, protein synthesis disruption, disruption of DNA/RNA transcription, translation and replication, disruption of cell division, and the like.

A representative example of a treatment of a medical condition that can benefit from using a combination of drugs having a different mechanism of biological activity is cancer. In the broad sense, most anticancer drugs work by impairing mitosis (cell division), effectively targeting fast-dividing cells. As these drugs cause damage to cells, they are termed cytotoxic. They prevent mitosis by various mechanisms including damaging DNA and inhibition of the cellular machinery involved in cell division. Without being bound by any particular theory, it is assumed that these drugs kill cancer cells by inducing a programmed form of cell death known as apoptosis. As anticancer chemotherapy affects cell division, tumors with high growth rates (such as acute myelogenous leukemia and the aggressive lymphomas, including Hodgkin's disease) are more sensitive to chemotherapy, as a larger proportion of the targeted cells are undergoing cell division at any time. Since malignancies with slower growth rates, such as indolent lymphomas, and heterogeneic tumors, tend to respond to chemotherapy more modestly, a combination of drugs that exert cell division inhibition with drugs that exert other mechanism of biological activity, such as anti-protein-biosynthesis activity, metabolism and cell membrane disruption is advantageous.

In some embodiments, the anticancer drug is an alkylating agent, or alkylating antineoplastic agent. Alkylating agents constitute a class of chemotherapeutics that exhibit the capacity to alkylate a wide range of molecules, including proteins, RNA and DNA, and this capacity to bind covalently to DNA via their alkyl group is the primary cause for their anti-cancer effects. DNA is made of two strands and the molecules may either bind twice to one strand of DNA (intrastrand crosslink) or may bind once to both strands (interstrand crosslink). If the cell tries to replicate cross-linked DNA during cell division, or tries to repair it, the DNA strands can break, and this leads to a form of programmed cell death called apoptosis. Alkylating agents will work at any point in the cell cycle and thus are known as cell cycle-independent drugs. For this reason the effect on the cell is dose dependent; the fraction of cells that die is directly proportional to the dose of drug. Subtypes of alkylating agents include nitrogen mustards, nitrosoureas, tetrazines, aziridines, cisplatins and derivatives, and non-classical alkylating agents. Nitrogen mustards include mechlorethamine, cyclophosphamide, melphalan, chlorambucil, ifosfamide and busulfan. Nitrosoureas include N-nitroso-N-methylurea (MNU), carmustine (BCNU), lomustine (CCNU) and semustine (MeCCNU), fotemustine and streptozotocin. Tetrazines include dacarbazine, mitozolomide and temozolomide. Aziridines include thiotepa, mytomycin and diaziquone (AZQ). Cisplatin and derivatives include cisplatin, carboplatin and oxaliplatin, which impair cell function by forming covalent bonds with the amino, carboxyl, sulfhydryl, and phosphate groups in biologically important molecules. Non-classical alkylating agents include procarbazine and hexamethylmelamine.

In some embodiments, the anticancer drug is an anti-metabolism agent, or an anti-metabolite. Anti-metabolites are a group of molecules that impede DNA and RNA synthesis; many of which have a similar structure to the building blocks of DNA and RNA. The building blocks are nucleotides; a molecule comprising a nucleobase, a sugar and a phosphate group. The nucleobases are divided into purines (guanine and adenine) and pyrimidines (cytosine, thymine and uracil). Anti-metabolites resemble either nucleobases or nucleosides (a nucleotide without the phosphate group), but have altered chemical groups. These drugs exert their effect by either blocking the enzymes required for DNA synthesis or becoming incorporated into DNA or RNA. By inhibiting the enzymes involved in DNA synthesis, anti-metabolites prevent mitosis because the DNA cannot duplicate itself. Also, after misincorporation of the molecules into DNA, DNA damage can occur and programmed cell death (apoptosis) is induced. Unlike alkylating agents, anti-metabolites are cell cycle dependent, which means that they exert therapeutic biological activity only during a specific part of the cell cycle, in this case S-phase (the DNA synthesis phase). For this reason, at a certain dose, the effect plateaus and proportionally no more cell death occurs with increased doses. Subtypes of the anti-metabolites are the anti-folates, fluoropyrimidines, deoxynucleoside analogues and thiopurines. Examples of anti-folates include methotrexate and pemetrexed. Methotrexate inhibits dihydrofolate reductase (DHFR), an enzyme that regenerates tetrahydrofolate from dihydrofolate. When the enzyme is inhibited by methotrexate, the cellular levels of folate coenzymes diminish. These are required for thymidylate and purine production, which are both essential for DNA synthesis and cell division. Pemetrexed is another anti-metabolite that affects purine and pyrimidine production, and therefore also inhibits DNA synthesis. It primarily inhibits the enzyme thymidylate synthase, but also has effects on DHFR, aminoimidazole carboxamide ribonucleotide formyltransferase and glycinamide ribonucleotide formyltransferase. The fluoropyrimidine family of anti-metabolites includes fluorouracil and capecitabine, whereas fluorouracil is a nucleobase analogue that is metabolised in cells to form at least two active products; 5-fluourouridine monophosphate (FUMP) and 5-fluoro-2'-deoxyuridine 5'-phosphate (fdUMP). FUMP becomes incorporated into RNA and fdUMP inhibits the enzyme thymidylate synthase; both of which lead to cell death. Capecitabine can be used in the context of some embodiments of the present invention as a prodrug of 5-fluorouracil, whereas once released off the conjugate, capecitabine is broken down in cells to produce the active drug 5-fluorouracil. Deoxynucleoside analogues include cytarabine, gemcitabine, decitabine, vidaza (5-azacytidine), fludarabine, nelarabine, cladribine, clofarabine and pentostatin. Thiopurines include thioguanine and mercaptopurine.

In some embodiments, the anticancer drug is an anti-microtubular agent, or an anti-microtubule. Anti-microtubule agents are plant-derived chemicals that block cell division by preventing microtubule function. Microtubules are an important cellular structure composed of two proteins; α-tubulin and β-tubulin, which are hollow rod shaped structures that are required for cell division, among other cellular functions. Microtubules are dynamic structures, which means that they are permanently in a state of assembly and disassembly. Vinca alkaloids and taxanes are the two main groups of anti-microtubule agents, and although both of these groups of drugs cause microtubule dysfunction, their mechanisms of action are completely opposite. The vinca alkaloids prevent the formation of the microtubules, whereas the taxanes prevent the microtubule disassembly; by doing so, they prevent the cancer cells from completing mitosis. Following this, cell cycle arrest occurs, which induces programmed cell death (apoptosis). In addition, these drugs can affect blood vessel growth; an essential process that tumors utilize in order to grow and metastasize. Vinca alkaloids are derived from the Madagascar periwinkle, *Catharanthus roseus* (formerly known as *Vinca rosea*). They bind to specific sites on tubulin, inhibiting the assembly of tubulin into microtubules. The original vinca alkaloids are completely natural chemicals that include vincristine and vinblastine. Following the success of these drugs, semi-synthetic vinca alkaloids were produced: vinorelbine, vindesine, and vinflunine. These drugs are cell cycle-specific. They bind to the tubulin molecules in S-phase and prevent proper microtubule formation required for M-phase.

Taxanes are natural and semi-synthetic anticancer drugs. The first drug of their class, paclitaxel, was originally extracted from the Pacific Yew tree, *Taxus brevifolia*. Some of these drugs, such as docetaxel, are produced semi-synthetically from a chemical found in the bark of another Yew tree; *Taxus baccata*. These drugs promote microtubule stability, preventing their disassembly. Paclitaxel prevents the cell cycle at the boundary of G2-M, whereas docetaxel exerts its effect during S-phase. Taxanes present difficulties in formulation as medicines because they are poorly soluble in water, and the tethering thereof to a conjugate, according to some embodiments of the present invention, may improve the usefulness of this drug.

The anti-microtubule podophyllotoxin is an antineoplastic lignan (anticancer drug) obtained primarily from the American Mayapple (*Podophyllum peltatum*) and Himalayan Mayapple (*Podophyllum hexandrum* or *Podophyllum emodi*). It has anti-microtubule activity, and its mechanism is similar to that of vinca alkaloids in that they bind to tubulin, inhibiting microtubule formation. Podophyllotoxin is used to produce two other drugs with different mechanisms of action: etoposide and teniposide.

In some embodiments, the anticancer drug is a topoisomerase inhibitor. Topoisomerase inhibitors are drugs that affect the activity of two enzymes: topoisomerase I and topoisomerase II. When the DNA double-strand helix is unwound, during DNA replication or transcription, for example, the adjacent unopened DNA winds tighter (supercoils), like opening the middle of a twisted rope. The stress caused by this effect is in part aided by the topoisomerase enzymes. They produce single- or double-strand breaks into DNA, reducing the tension in the DNA strand. This allows the normal unwinding of DNA to occur during replication or transcription, and inhibition of topoisomerase I or II interferes with both of these processes.

Two topoisomerase I inhibitors, irinotecan and topotecan, are semi-synthetically derived from camptothecin, which is obtained from the Chinese ornamental tree *Camptotheca acuminata*. Drugs that target topoisomerase II can be divided into two groups. The topoisomerase II poisons cause increased levels enzymes bound to DNA. This prevents DNA replication and transcription, causes DNA strand breaks, and leads to programmed cell death (apoptosis). These agents include etoposide, doxorubicin, mitoxantrone and teniposide. The second group, catalytic inhibitors, are drugs that block the activity of topoisomerase II, and therefore prevent DNA synthesis and translation because the DNA cannot unwind properly. This group includes novobiocin, merbarone, and aclarubicin, which also have other significant mechanisms of biological activity.

In some embodiments, the anticancer drug is a cytotoxic antibiotic agent or cytotoxic antibiotics. Cytotoxic antibiotics are a varied group of drugs that have various mechanisms of biological activity (therapeutic action). The group includes anthracyclines and other drugs such as actinomycin, bleomycin, plicamycin and mitomycin. Doxorubicin and daunorubicin were the first two anthracyclines, and were obtained from the bacterium *Streptomyces peucetius*. Derivatives of these compounds include epirubicin and idarubicin. Other clinically used drugs in the anthracyline group are pirarubicin, aclarubicin, and mitoxantrone. The mechanisms of biological activity of anthracyclines include DNA intercalation (molecules insert between the two strands of DNA), generation of highly reactive free radicals that damage intercellular molecules and topoisomerase inhibition. Actinomycin is a complex molecule that intercalates DNA and prevents RNA synthesis. Bleomycin, a glycopeptide isolated from *Streptomyces verticillus*, also intercalates DNA, but produces free radicals that damage DNA. This occurs when bleomycin binds to a metal ion, becomes chemically reduced and reacts with oxygen. Mitomycin is a cytotoxic antibiotic with the ability to alkylate DNA.

According to some embodiments of the present invention, the drugs that are linked in the conjugate presented herein are selected according to their individual pharmacokinetics and pharmacology parameters for absorption, distribution, metabolism, excretion and toxicity (ADME-Tox), collectively referred to herein as ADME-Tox parameters. These ADME-Tox parameters govern some of the therapeutic efficacy of the drugs, hence while some drugs may be highly potent in vitro, their ADME-Tox parameters may render them less effective due to slow absorption and/or distribution, and/or rapid metabolism and/or excretion.

According to some embodiments of the present invention, at least one of the drugs that are linked in the conjugate presented herein, is selected to exhibit at least one ADME-Tox parameter that is different than the ADME-Tox parameter of the other drug in the same conjugate.

Methods of Usage:

Since the conjugates presented herein can carry, deliver and controllably release a wide variety of drugs, the conjugates can be used to treat various medical conditions. The conjugates presented herein can therefore be used as an active ingredient in a variety of pharmaceutical compositions, and in the preparation of a variety of medicaments.

Accordingly there is provided a pharmaceutical composition that includes, as an active ingredient, the conjugate, according to embodiments of the present invention, and a pharmaceutically acceptable carrier.

Similarly, there is provided a use of the conjugate, according to embodiments of the present invention, in the preparation of a medicament.

According to some embodiments of the present invention, the pharmaceutical composition or medicament, are used to treat a medical condition.

Also provided herein is a method of treating a medical condition in a subject in need thereof, which includes administering to the subject a therapeutically effective amount of the conjugate, according to embodiments of the present invention, as presented herein.

In the context of embodiments of the present invention, the therapeutically effective amount may refer to the conjugate as a whole or to the amount of one or more bioactive agents forming the same. The efficacy of any bioactive agent, including the conjugates presented herein, can be determined by several methodologies known in the art.

According to another aspect of embodiments of the present invention, any one of the conjugates described herein is identified for use in treating a subject diagnosed with a medical condition treatable by at least one of the drugs linked to form the conjugate.

According to another aspect of embodiments of the present invention, there is provided a use of any of the conjugates described herein as a medicament. In some embodiments, the medicament is for treating a subject diagnosed with a medical condition treatable by at least one of the drugs linked to form the conjugate.

In any of the methods and uses described herein, the conjugate can be administered as a part of a pharmaceutical composition, which further comprises a pharmaceutical acceptable carrier, as detailed hereinbelow. The carrier is selected suitable to the selected route of administration.

The conjugates presented herein can be administered via any administration route, including, but not limited to, orally, by inhalation, or parenterally, for example, by intravenous drip or intraperitoneal, subcutaneous, intramuscular or intravenous injection, or topically (including ophthalmically, vaginally, rectally, intranasally).

According to some embodiments, the composition is packaged in a packaging material and identified in print, in or on the packaging material, for use in the treatment of a medical condition treatable by at least one of the drugs linked to form the conjugate.

As used herein the phrase "pharmaceutical composition" or the term "medicament" refer to a preparation of the conjugates presented herein, with other chemical components such as pharmaceutically acceptable and suitable carriers and excipients, and optionally with additional active agents. The purpose of a pharmaceutical composition is to facilitate administration of the conjugate to a subject.

Hereinafter, the term "pharmaceutically acceptable carrier" refers to a carrier or a diluent that does not cause significant irritation to an organism and does not abrogate the biological activity and properties of the administered conjugate. Examples, without limitations, of pharmaceutically acceptable carriers are: propylene glycol, saline, emulsions and mixtures of organic solvents with water, as well as solid (e.g., powdered) and gaseous carriers.

Herein the term "excipient" refers to an inert substance added to a pharmaceutical composition to further facilitate administration of a conjugate. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences" Mack Publishing Co., Easton, Pa., latest edition, which is incorporated herein by reference.

The pharmaceutical composition may be formulated for administration in either one or more of routes depending on whether local or systemic treatment or administration is of choice, and on the area to be treated. Administration may be done orally, by inhalation, or parenterally, for example by intravenous drip or intraperitoneal, subcutaneous, intramuscular or intravenous injection, or topically (including ophthalmically, vaginally, rectally, intranasally).

Formulations for topical administration may include but are not limited to lotions, ointments, gels, creams, suppositories, drops, liquids, sprays and powders. Conventional pharmaceutical carriers, aqueous, powder or oily bases, thickeners and the like may be necessary or desirable.

Compositions for oral administration include powders or granules, suspensions or solutions in water or non-aqueous media, sachets, pills, caplets, capsules or tablets. Thickeners, diluents, flavorings, dispersing aids, emulsifiers or binders may be desirable.

Formulations for parenteral administration may include, but are not limited to, sterile solutions which may also contain buffers, diluents and other suitable additives. Slow release compositions are envisaged for treatment.

The amount of a composition to be administered will, of course, be dependent on the subject being treated, the severity of the affliction, the manner of administration, the judgment of the prescribing physician, etc.

Pharmaceutical compositions for use in accordance with embodiments of the invention thus may be formulated in conventional manner using one or more pharmaceutically acceptable carriers comprising excipients and auxiliaries, which facilitate processing of the conjugates presented herein into preparations which can be used pharmaceutically. Proper formulation is dependent upon the route of administration chosen. Toxicity and therapeutic efficacy of the conjugate presented herein can be determined by standard pharmaceutical procedures in experimental animals, e.g., by determining the $EC_{50}$, the $IC_{50}$ and the $LD_{50}$ (lethal dose causing death in 50% of the tested animals) for a subject combination of antimicrobial agent(s) and polymer (s). The data obtained from these activity assays and animal studies can be used in formulating a range of dosage for use in human.

The dosage may vary depending upon the dosage form employed and the route of administration utilized. The exact formulation, route of administration and dosage can be chosen by the individual physician in view of the patient's condition. (See e.g., Fingl et al., 1975, in "*The Pharmacological Basis of Therapeutics*", Ch. 1 p. 1). In general, the dosage is related to the efficacy of the active ingredient which, in the context of embodiments of the invention, is related to its minimal inhibitory concentration (MIC) and the particular pharmacokinetics and pharmacology thereof for absorption, distribution, metabolism, excretion and toxicity (ADME-Tox) parameters. The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA (the U.S. Food and Drug Administration) approved kit, which may contain one or more unit dosage forms containing the active ingredient. The pack may, for example, comprise metal or plastic foil, such as, but not limited to a blister pack or a pressurized container (for inhalation). The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions for human or veterinary administration. Such notice, for example, may be of labeling approved by the U.S. Food and Drug Administration for prescription drugs or of an approved product insert. Compositions comprising the conjugates presented herein formulated in a compatible pharmaceutical carrier may also be prepared, placed in an appropriate container, and labeled for treatment of an indicated condition, as is detailed herein.

The present embodiments further encompass any enantiomers, prodrugs, solvates, hydrates and/or pharmaceutically acceptable salts of the conjugates described herein and methods, compositions and uses utilizing enantiomers, prodrugs, solvates, hydrates and/or pharmaceutically acceptable salts of the conjugates described herein.

The term "prodrug" refers to an agent, which is converted into a bioactive agent (the active parent drug) in vivo. In essence, the conjugates presented herein constitute a form of a prodrug, as drug moieties, which are designed for release as bioactive agents in a controllable manner, are linked thereto. Prodrugs are typically useful for facilitating and/or targeting the administration of the parent drug. They may, for instance, be bioavailable by oral administration whereas the parent drug is not. A prodrug may also have improved solubility as compared with the parent drug in pharmaceutical compositions. Prodrugs are also often used to achieve a sustained release of a bioactive agent in vivo. An example, without limitation, of a prodrug would be a bioactive agent, according to some embodiments of the present invention, having one or more carboxylic acid moieties, which is administered as an ester (the "prodrug"). Such a prodrug is hydrolyzed in vivo, to thereby provide the free bioactive agent (the parent drug). The selected ester may affect both the solubility characteristics and the hydrolysis rate of the prodrug. A prodrug is typically designed to facilitate administration, e.g., by enhancing absorption. A prodrug may comprise, for example, the active compound modified with ester groups, for example, wherein any one or more of the hydroxyl groups of a compound is modified by an acyl group, optionally $(C_{1-4})$acyl (e.g., acetyl) group to form an ester group, and/or any one or more of the carboxylic acid groups of the compound is modified by an alkoxy or aryloxy group, optionally $(C_{1-4})$alkoxy (e.g., methyl, ethyl) group to form an ester group.

The term "solvate" refers to a complex of variable stoichiometric (e.g., di-, tri-, tetra-, penta-, hexa-, and so on), which is formed by a solute (the conjugates described herein) and a solvent, whereby the solvent does not interfere with the biological activity of the solute. Suitable solvents include, for example, ethanol, acetic acid and the like.

The term "hydrate" refers to a solvate, as defined hereinabove, where the solvent is water.

The phrase "pharmaceutically acceptable salt" refers to a charged species of the parent conjugate and its counter ion(s), which is typically used to modify the solubility characteristics of the parent conjugate and/or to reduce any significant irritation to an organism by the parent conjugate, while not abrogating the biological activity and properties of the administered conjugate.

Examples of pharmaceutically acceptable salts include, but are not limited to, mineral or organic acid salts of basic residues such as amines, and alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. Conventional nontoxic salts include those derived from inorganic acids such as hydrochloric, hydrobromic, sulfuric, sulfamic, phosphoric and nitric acid; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic and isethionic acids. The pharmaceutically acceptable salts can be synthesized from the parent compound, which contains a basic or acidic moiety, by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed. (Mack Publishing Company, Easton, Pa., 19143, p. 1418).

Representative examples of pharmaceutically acceptable salts that can be efficiently used in the context of the present invention include, without limitation, conjugate hydrochloride and conjugate mesylate.

According to some embodiments of the present invention, the compositions, uses and method of treatment, according to some embodiment of the present invention, may include the co-administration of at least one additional therapeutically active agent, as this is defined and discussed herein.

Cancer Treatment and Chemotherapy:

The conjugate presented herein can be used to treat any medical condition that is treatable by administration of a bioactive agent (drug). According to some embodiments of the present invention, it is advantageous to use the conjugate to treat medical conditions which are treatable by administration of a combination of drugs. In some embodiments, the medical condition includes cancer. In some embodiments of the present invention, the medical condition is associated with malignant cells and tumors, collectively referred to herein as cancer.

Cancer is a spontaneous, acquired or genetic disease in which mutations violate cell growth and survival pathways. Essentially abnormal tissue growth (neoplasm) develops through a process whereby cancer begins in a single cell and passes its malignant potential to subsequent generations of cells. A carcinogenic event is usually operated by some external disruptive factors, such as viruses, radiation (such as sunlight, x-rays and radioactive sources which emit energy and subatomic particles) and chemical carcinogens, mutagens or teratogens. Mammalian cells have multiple safeguards to protect them against the potentially lethal effects of cancer gene mutations, but when several genes are defective, an invasive cancer develops. Human cancers originate from mutations that usually occur in somatic tissues; however, hereditary forms of cancer exist in which individuals are heterozygous for a germline mutation.

The mutations target three types of genes (cancer genes), namely tumor suppressor genes, oncogenes, and stability genes. Loss-of-function mutations in tumor suppressors and gain-of-function mutations in oncogenes lead to cancer, while loss-of-function mutations in stability genes increase the rates of mutation of tumor suppressors and oncogenes. All cancer mutations operate similarly at the physiologic level: they drive the carcinogenic process by increasing tumor cell number through the stimulation of cell birth or the inhibition of cell-cycle arrest or cell death. The increase is usually caused by facilitating the provision of nutrients through enhanced angiogenesis, by activating genes that drive the cell cycle or by inhibiting normal apoptotic processes.

The most common types of cancer treatment are surgery, radiotherapy and chemotherapy. Radiotherapy is usually used alone or in combination with surgery and/or chemotherapy. Other types of treatments include hormone therapy that is used in combination with surgery and/or chemotherapy for treatment of, for example, androgen-dependent prostate cancer or estrogen-dependent breast cancer.

Cryosurgery uses cold liquid nitrogen or gas argon to destroy abnormal tissue. Relatively new additions to the family of cancer treatments include biological therapy and angiogenesis inhibitors. Biological therapy is based on the stimulation of the body's own immune system, either directly or indirectly, to fight off cancer or to diminish side effects caused by other treatments.

To date, chemotherapy remains the most common and most frequently used in cancer treatment, alone or in combination with other therapies. Currently available anticancer chemotherapies act by affecting specific molecular targets in proliferating cancer cells, leading to inhibition of essential intracellular processes such as DNA transcription, synthesis and replication.

Unfortunately anticancerous drugs are highly toxic, as they are designed to kill mammalian cells, and are therefore harmful also to normal proliferating cells resulting in debilitating and even lethal side effects. Some of these adverse effects are gastrointestinal toxicity, nausea, vomiting, and diarrhea when the epithelial lining of the intestine is affected. Other side effects include alopecia, when the hair follicles are attacked, bone marrow suppression and neutropenia due to toxicity of hematopoietic precursors. Therefore the effectiveness of currently used anticancerous drugs is dose-limited due to their toxicity to normal rapidly growing cells.

One of the contemporary approaches in the fight against cancer is engineering of molecular targeted drugs that permeate cancer cells and specifically modulate activity of molecules that belong to signal-transduction pathways. These targets include products of frequently mutated oncogenes, such as k-Ras and other proteins that belong to tyrosine kinase signal transduction pathways. For example, Imatinib (Gleevec®), is the first such drug, approved for treatment of chronic myelogenous leukemia (CML). Imatinib blocks the activity of non-receptor tyrosine kinase BCR-Abl oncogene, present in 95% of patients with CML. Imatinib was found to be effective in the treatment of CML and certain tumors of the digestive tract. Nevertheless, as others, this new compound is not completely specific to its target; therefore side effects emerge, including severe congestive cardiac failure, pulmonary tuberculosis, liver toxicity, sweet syndrome (acute febrile neutrophilic dermatosis), leukocytosis, dermal edemas, nausea, rash and musculoskeletal pain.

Angiogenesis inhibitors are currently investigated for their use in cancer treatment and to date, one anti-angiogenetic drug, Bevacizumab (Avastin®), was approved for the treatment of solid tumors in combination with standard chemotherapy. However, as in all chemotherapeutic drugs, Bevacizumab causes a number of adverse side effects such as hypertension, blood clots, neutropenia, neuropathy, proteinuria and bowel perforation.

In some embodiments, the targeting moiety of the conjugates presented herein, is responsible for the higher concentration of the conjugate at the targeted bodily site compared to non-targeted bodily sites, thereby reducing the adverse side effects associated with the toxicity of the anti-cancer drugs attached thereto. In addition, the linking moieties attached the anti-cancer drugs to the conjugate are selected such that they cleave in conditions that are present at the targeted site more so than in non-targeted sites, thereby releasing the payload of drugs at the targeted site at a higher rate compared to non-targeted sites.

Treatment of cancer is becoming even more complicated, since on top of the many factors that cause tumor formation and the multiple adverse side effects associated with currently available anticancerous agents, there are a myriad of mechanisms by which cells become resistant to unspecific drugs.

Mechanisms of drug resistance include prevention from entering the cells, pumping the drug out of the cells, enzymatic inactivation, prevention of drug activity by mutation or altered expression of the target, and inhibition of biochemical pathways by mutations in oncogenes, tumor-suppressor genes or stability genes.

Many of the most prevalent forms of human cancer resist effective chemotherapeutic intervention. Some tumor populations, especially adrenal, colon, jejunal, kidney and liver carcinomas, appear to have drug-resistant cells at the outset of treatment [Barrows, L. R., "Antineoplastic and Immunoactive Drugs", Chapter 75, pp 1236-1262, in: Remington: The Science and Practice of Pharmacy, Mack Publishing Co. Easton, Pa., 1995]. In other cases, a resistance-conferring genetic change occurs during treatment; the resistant daughter cells then proliferate in the environment of the drug. Whatever the cause, resistance often terminates the usefulness of an anticancerous drug, and the emergence of multidrug resistance (MDR) sadly lead to therapeutic failure in many cancer patients [Liscovitch, M. and Lavie, Y., IDrugs, 2002, 5(4), 349-55].

Many studies have been conducted in order to elucidate the mechanism behind the development of MDR cancer cells. One of the most recognized mechanisms involves the ABC (ATP Binding Cassette) transporter proteins. These proteins are capable of coupling the energy of ATP binding and hydrolysis, so as to transport substrates across a cell membrane. The normal physiological role of these proteins is detoxification and clearance by active secretion of intracellular xenobiotic and other undesired substances out of the cell. Thus, in order to ultimately perform their normal physiological role, nature has designed these proteins capable of extruding a wide scope of molecules.

Due to their recognized activity in multidrug resistance (MDR) in tumor chemotherapy these transporter proteins are widely termed in the art as "MDR extrusion pumps".

The lowered efficacy of chemotherapy is linked to the fact that MDR extrusion pumps are over-expressed in cancer cells, as compared to their expression level in normal cells, and are responsible for pumping chemotherapeutic drugs out of the cell, which reduces the levels of intracellular drug below lethal thresholds regardless of the of nature of the cancer cell and/or the drug.

This mechanism of resistance may account for de novo resistance in common tumors, such as colon cancer and renal cancer, and for acquired resistance, as observed in common hematologic tumors such as acute nonlymphocytic leukemia and malignant lymphomas.

Both the resistance to conventional drugs monotherapy and the toxicity of currently use chemotherapeutic agents, support the rationale for combination drug therapy and the use of agents that can fight MDR. Compounds capable of inhibiting MDR extrusion pumps are known in the art as chemosensitizers or chemosensitizing agents. Combination of drugs with different modes of action may protect normal cells against chemotoxicity [Carvajal, D. et al., Cancer Res., 2005, 65, 1918-1924] or facilitate chemotherapy action on resistant tumors [Molnar, J. et al., Curr. Pharm. Des, 2006, 12, 287-311].

In some embodiments, the conjugates presented herein is designed to carry a variety of anti-cancer drugs that differ from one another in their mechanism of action. This differential mechanism of action can overcome MDR by simultaneously attacking more than one biological system of the malignant cell, causing death before the cell can respond to the attack by the MDR mechanisms.

In the context of some embodiments of the present invention, the term "cancer" refers, but not limited to acute lymphoblastic, acute lymphoblastic leukemia, acute lymphocytic leukemia, acute myelogenous leukemia, acute myeloid leukemia, adrenocortical carcinoma, AIDS-related lymphoma, anal cancer, appendix cancer, basal-cell carcinoma, bladder cancer, brain cancer, brainstem glioma, breast cancer, bronchial adenomas/carcinoids, Burkitt's lymphoma, carcinoid tumor, cerebellar or cerebral astrocytoma, cervical cancer, cholangiocarcinoma, chondrosarcoma, chronic lymphocytic or chronic lymphocytic leukemia, chronic myelogenous or chronic myeloid leukemia, chronic myeloproliferative disorders, colon cancer, cutaneous T-cell lymphoma, desmoplastic small round cell tumor, endometrial uterine cancer, ependymoma, esophageal cancer, Ewing's sarcoma, extracranial germ cell tumor, extragonadal germ cell tumor, extrahepatic bile duct cancer, gallbladder cancer, gastric (stomach) cancer, gastrointestinal carcinoid tumor, gastrointestinal stromal tumor (GIST), gestational trophoblastic tumor, glioma of the brain stem, hairy cell leukemia, head and neck cancer, heart cancer, hepatocellular (liver) cancer, Hodgkin lymphoma, hypopharyngeal cancer, hypothalamic and visual pathway glioma, intraocular melanoma, Islet cell carcinoma, Kaposi sarcoma, laryngeal cancer, leukaemia, lip and oral cavity cancer, liposarcoma, lymphoma, male breast cancer, malignant mesothelioma, medulloblastoma, melanoma, Merkel cell skin carcinoma, mesothelioma, metastatic squamous neck cancer, mouth cancer, multiple endocrine neoplasia syndrome, multiple myeloma, multiple myeloma/plasma cell neoplasm, mycosis fungoides, myelodysplastic/myeloproliferative diseases, nasal cavity and paranasal sinus cancer, nasopharyngeal carcinoma, neuroblastoma, non-Hodgkin lymphoma, non-melanoma skin cancer, non-small cell lung cancer, oligodendroglioma, oral cancer, oropharyngeal cancer, osteosarcoma and malignant fibrous histiocytoma, ovarian cancer, ovarian germ cell tumor, ovarian epithelial cancer (surface epithelial-stromal tumor), ovarian low malignant potential tumor, pancreatic cancer, paranasal sinus and nasal cavity cancer, parathyroid cancer, penile cancer, pharyngeal cancer, pheochromocytoma, pineal astrocytoma, pineal germinoma, pineoblastoma and supratentorial primitive neuroectodermal tumors, pituitary adenoma, plasma cell neoplasia, pleuropulmonary blastoma, primary carcinoma, primary central nervous system lymphoma, primary liver cancer, prostate cancer, rectal cancer, renal cell carcinoma, renal pelvis and ureter carcinoma, retinoblastoma, rhabdomyosarcoma, salivary gland cancer, Sezary syndrome, small cell lung cancer, small intestine cancer, soft tissue sarcoma, squamous cell carcinoma, stomach cancer, supratentorial primitive neuroectodermal tumor, testicular cancer, throat cancer, thymoma and thymic carcinoma, thyroid cancer, transitional cell cancer of the renal pelvis and ureter, urethral cancer, uterine sarcoma, vaginal cancer, visual pathway and hypothalamic glioma, vulvar cancer, Waldenström macroglobulinemia and Wilms tumor.

It is expected that during the life of a patent maturing from this application many relevant anti-cancerous drug conjugates will be developed and the scope of the phrase "anti-cancerous drug conjugates" is intended to include all such new technologies a priori.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the phrase "substantially devoid of" or "essentially devoid of" a certain substance refers to a composition that is totally devoid of this substance or includes no more than 0.1 percent of the substance by weight or volume.

The term "exemplary" is used herein to mean "serving as an example, instance or illustration". Any embodiment described as "exemplary" is not necessarily to be construed as preferred or advantageous over other embodiments and/or to exclude the incorporation of features from other embodiments.

The words "optionally" or "alternatively" are used herein to mean "is provided in some embodiments and not provided in other embodiments". Any particular embodiment of the invention may include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non-limiting fashion.

Example 1

General Synthetic Approach

The general synthetic approach of forming the presently provided conjugates is based on the provision of mutually acting (synergistic, cooperative or additive) drugs and a selection of a linker moiety attachment site in each drug, selection linker moiety length and composition, and the design of drug analogs for attachment to the linker. In general, forming the conjugates can be based on a coupling reactions that form a biocleavable moiety or bond, such as, e.g., coupling an amino group to a carboxylic group to form an amide.

Scheme 10 below illustrates the general synthetic approach of forming the presently provided conjugates, where each individual drug molecules, "Drug 1" and "Drug 2" is represented by a circle of a rectangle, and the biodegradable linking moiety that forms as a result of the coupling reaction is denoted by a solid line and "LM".

Scheme 10

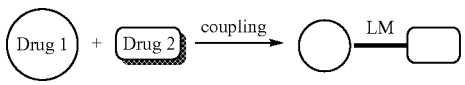

The general synthetic approach has been used to form a number of exemplary conjugates according to embodiments of the present invention, as listed in Table 1 above. The coupling reaction conditions were used according to the desired linking moiety, wherein an ester was afforded by using DCC, HOBt, DMAP in DMF at room temperature; an amide was afforded by using DCC, HOBt, DIEA in DMF at room temperature, and a carbamate was afforded by using p-$NO_2PhO_2CCl$ and DIEA in DCM/DMF.

Scheme 11 below illustrates the synthesis of an exemplary conjugate, according to some embodiments of the present invention, referred to herein as Chimera 358, consisting of a residue of a topo II inhibitor Amonafide (AM) and a residue of a mustard DNA alkylating drug Chlorambucil (CLB), linked by a biocleavable amide linking moiety. It is noted that Chimera 358 contains aromatic core structure and two tertiary amine moieties what may assist, upon converting into HCl salt, to penetrate the blood-brain barrier.

Scheme 11

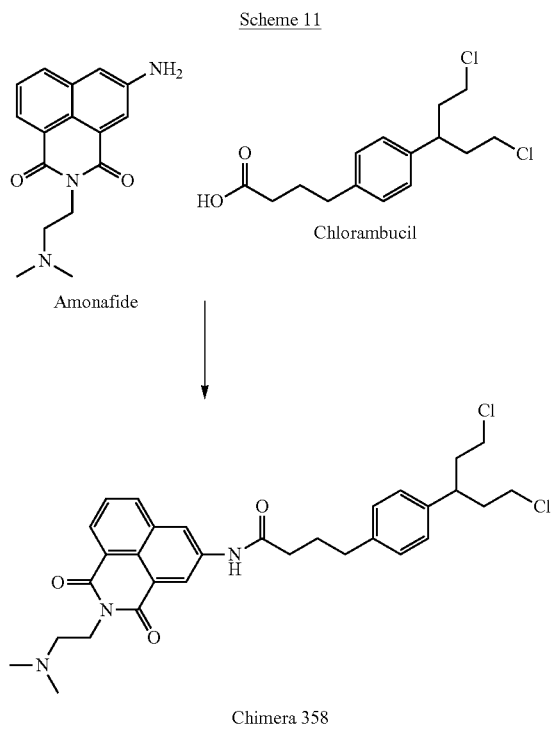

All resulting conjugates were obtained in good yields, purified by HPLC and identified by NMR and MS spectroscopy.

Preparation of Chimera 358: Chlorambucil (0.5 mmole) was dissolved in 5 ml of acetonitrile containing 2 equivalents of triethylamine. The carboxylate solution was cooled to −15--20° C. following isobutyl chloroformate addition (2 equivalents), resulting white suspended solution. Addition 10 ml portion of acetonitrile resulted in clear solution. After 15 minutes of stirring, acetonitrile/dimethylformamide solution (5/2) of amonafide was added and the mixture stirred for additional 30 minutes in a cool bath, following 12 hours of stirring at room temperature. Portion of 5-10 ml of DMSO were added during the period of the reaction, in order to keep the solution clear. By the completion of the reaction (monitoring by LC-MS), the mixture was subjected to purification by HPLC. Clean fractions were lyophilized resulting yellow powder in 75% yield. $^1$H NMR: (400 MHz, DMSO-d6): δ 1.91 (quint, J=8 Hz, 2H), 2.43 (t, J=8 Hz, 2H), 2.56 (t, J=8 Hz, 2H), 2.90 (s, 3H), 2.91 (s, 3H), 3.46 (m, 2H), 3.69 (s, 8H), 4.39 (t, J=5.5 Hz, 2H), 6.68 (d, J=8 Hz, 2H), 7.07 (d, J=8 Hz, 2H), 7.83 (dd, J=8 Hz, 1H), 8.39 (m, 2H), 8.67 (d, J=2 Hz, 1H), 8.78 (d, J=2 Hz, 1H), 10.57 (s, 1H);

$^{13}$C and DEPTQ ($^{13}$C) NMR: (101 MHz, DMSO-d6): δ 26.83 (CH2), 33.49 (CH2), 30.06 (CH2), 35.79 (CH2), 41.03 (2 CH2), 42.64 (2 CH3), 52.08 (2 CH2), 54.78 (CH2), 111.78 (2CH), 120.70 (CH), 121.75 (C), 122.60 (C), 123.88 (CH), 123.98 (C), 127.48 (CH), 128.89 (CH), 129.29 (2CH), 129.59 (C), 132.02 (C), 133.82 (CH), 138.02 (C), 144.37 (C), 163.72 (CO), 163.96 (CO), 171.88 (CO—NHR); LC-MS m/z: 570 (M+H+), RT=9.77 min.

Example 2

In Vitro Activity Experiments

An exemplary conjugate, Chimera 358, described hereinabove, is a result of linking Amonafide (AM) and Chlorambucil (CLB). AM is drug candidate that has systematically failed in advanced clinical trials, while CLB is tolerable by majority of solid tumors. The principles of the present invention are demonstrated by the in vitro activity assays using Chimera 358, compared to AM and CLB used alone, and a mixture thereof.

Tumor Cytotoxicity:

In the in vitro studies presented herein, Chimera 358 has been shown to be highly toxic to four solid tumor cell lines, and in addition exhibits notable fluorescent properties for ex vivo and in vivo imaging and diagnostics. The tumors cell lines used in this study included PC-3 (human prostate cancer), WM-266-4 cell (human metastatic melanoma), MDA-MB 231 (human breast cancer) and A172 (glioblastoma). In all in vitro assays, Chimera 358 in concentrations that range from 5 to 25 μM showed remarkable inhibition of cancer cell growth as oppose to AM and CLB as single drugs. The benign fibroblasts were tolerable to this conjugate, accentuating its potential as anticancer candidate. At the end of the culture period, cell growth was estimated by XTT assay. After 4 hours incubation of the cells with the XTT reagent, optical density (OD) of the reduced XTT product was then measured at 480 and 680 nm. Percentage of growth inhibition by a test compound was calculated by comparison of the treated culture versus a control culture (free of any compound). The result shown for each concentration point represents the mean+/−standard error calculated from 3 different experiments. In each experiment the compounds were tested in triplicates.

Figure 1B:
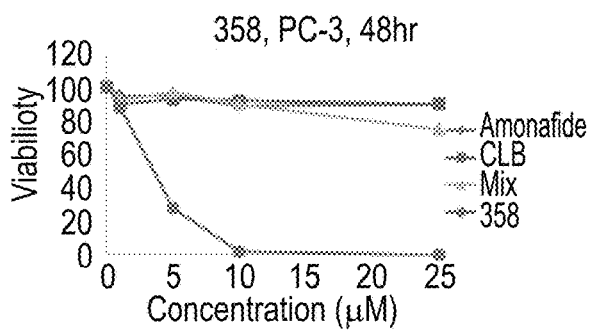
Figure 1C:
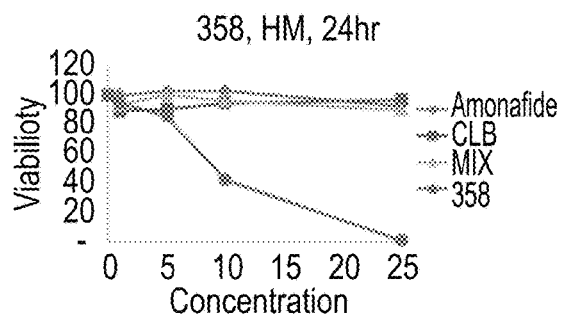
Figure 1D:
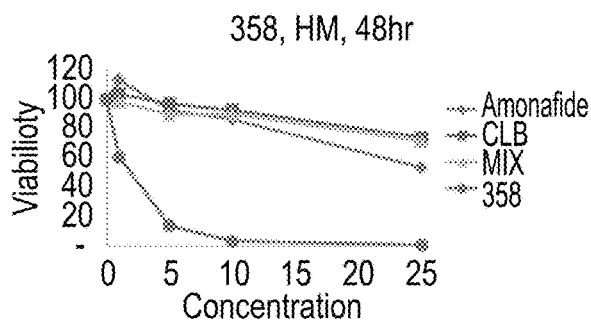
Figure 1E:
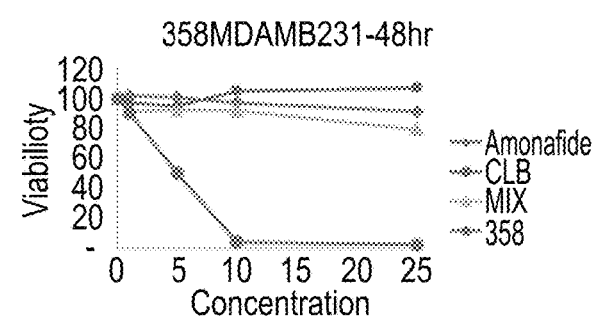
Figure 1F:
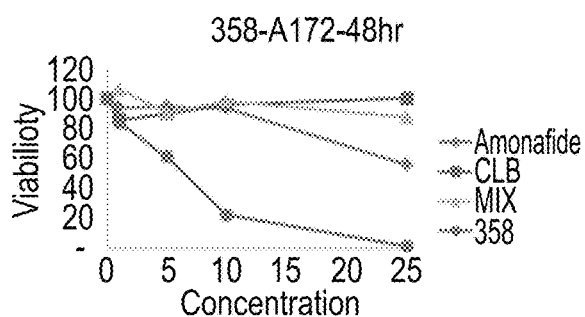

FIGS. 1A-F present comparative plots of the results of the cytotoxicity studies of Chimera 358, an exemplary conjugate according to embodiments of the present invention, consisting of a residue of Amonafide (AM) and a residue of Chlorambucil (CLB), as obtained from exposure of three types of human cell lines to 5-25 μM of Chimera 358, wherein FIG. 1A shows the dose response on PC-3 cells viability during a 24 hours incubation period, FIG. 1B shows the dose response on PC-3 cells viability during a 48 hours incubation period, FIG. 1C shows the dose response on WM-266-4 cell cells viability during a 24 hours incubation period, FIG. 1D shows the dose response on WM-266-4 cell cells viability during a 48 hours incubation period, FIG. 1E shows the dose response on MDA-MB 231 cells viability during a 24 hours incubation period, and FIG. 1F shows the dose response on MDA-MB 231 cells viability during a 24 hours incubation period (response to AM alone marked by diamonds, to CLB by squares, the mixture of AM and CLB by triangles and Chimera 358 marked by circles).

As can be seen in FIGS. 1A-F, the exemplary conjugate, according to some embodiments of the present invention, Chimera 358, has shown notable cell toxicity at all tested concentrations, while the drugs used alone or mixed together has low or no effect on tumor cell viability.

Detection of Apoptotic/Necrotic Stages:

Apoptosis is an active, programmed process of autonomous cellular dismantling that avoids eliciting inflammation. In apoptosis, phosphatidylserine (PS) is transferred to the outer leaflet of the plasma membrane. As a universal indicator of the initial/intermediate stages of cell apoptosis, the appearance of phosphatidylserine on the cell surface can be detected before morphological changes are observed.

Detection of apoptotic/necrotic stages of tumor cells was examined by Annexin V-FITC/PI apoptosis detection kit (MEBCYTO). Viable cells are negative for staining of either Annexin V or PI. Early apoptotic stage indicated with positive Annexin V and negative PI, whereas late-apoptotic and necrotic stages characterized by high PI signal.

Figure 2C:
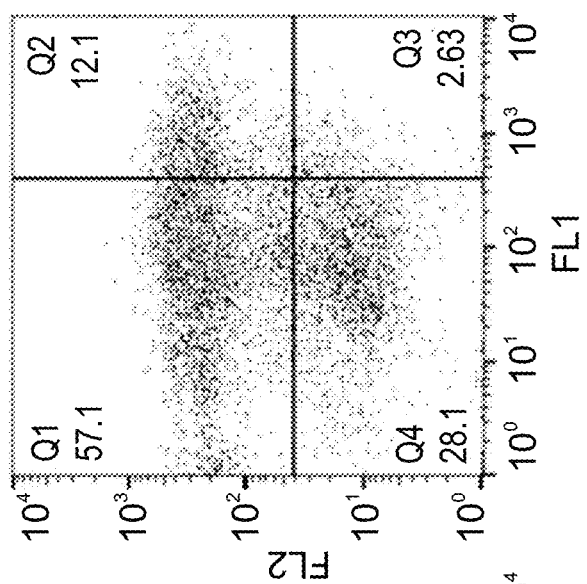
FIGS. 2A-2C present flow cytometry analysis of human metastatic melanoma cells treated with 10 μM of Chimera 358 for 2 hours (FIG. 2A), 4 hours (FIG. 2B) and 8 hours (FIG. 2C), showing detection of apoptotic/necrotic stages of the cells.
Figure 2B:
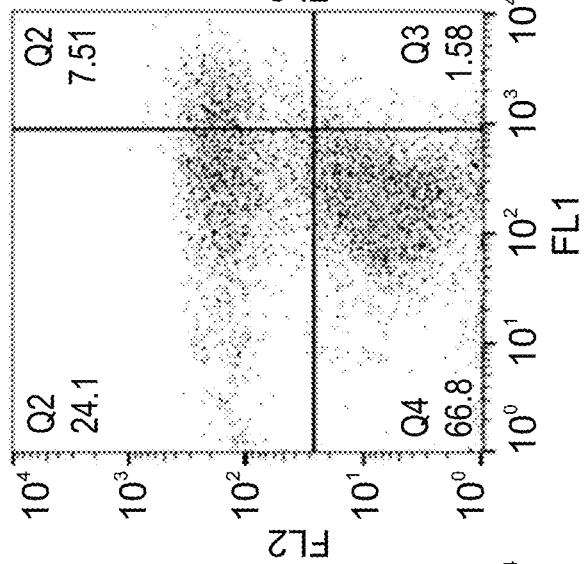
Figure 2A:
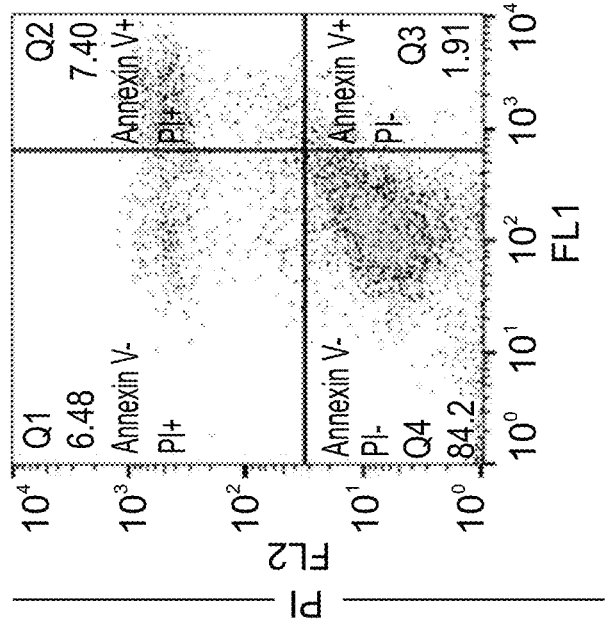

FIGS. 2A-C present flow cytometry analysis of human metastatic melanoma cells treated with 10 μM of chimera 358 for 2 hours (FIG. 2A), 4 hours (FIG. 2B) and 8 hours (FIG. 2C), showing detection of apoptotic/necrotic stages of the cells.

As can be seen in FIGS. 2A-C, the results are typical for three independent experiences.

Figure 3A:
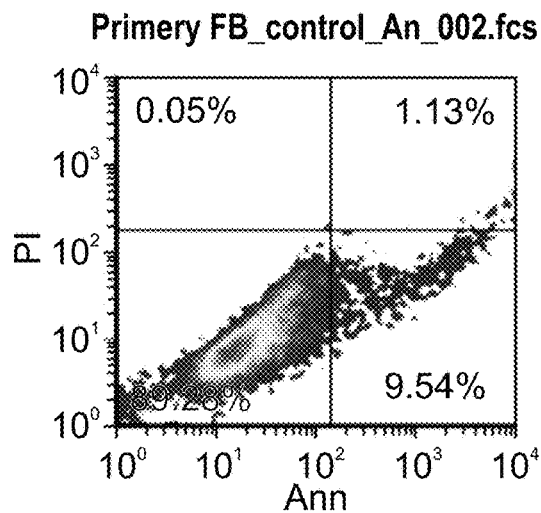
FIGS. 3A-3E present flow cytometry analysis of fibroblast cells untreated as control (FIGS. 3A-3B), treated with 10 μM of Chimera 358 for 3 hours (FIG. 3C), 6 hours (FIG. 3D), and 24 hours (FIG. 3E), showing detection of apoptotic/necrotic stages of the cells.
Figure 3B:
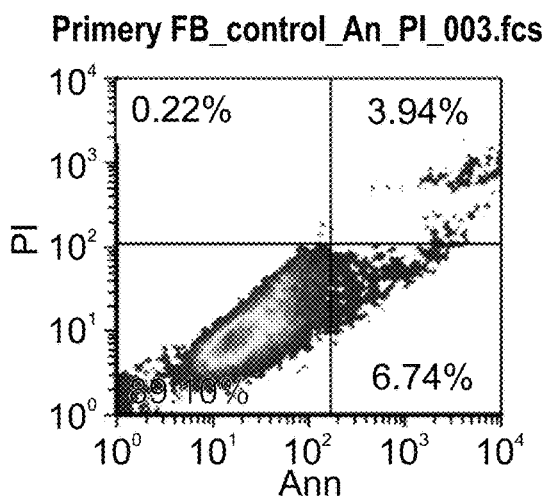
Figure 3C:
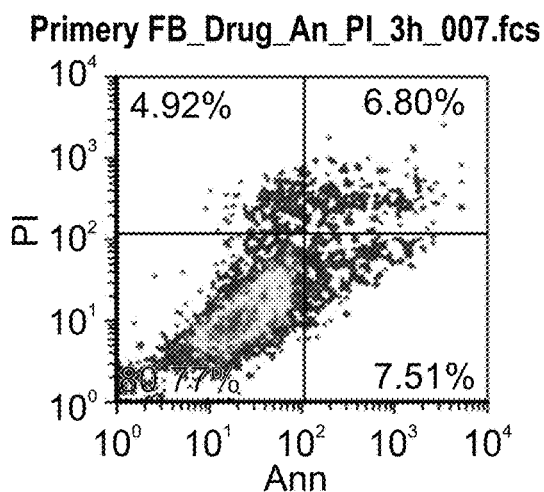
Figure 3D:
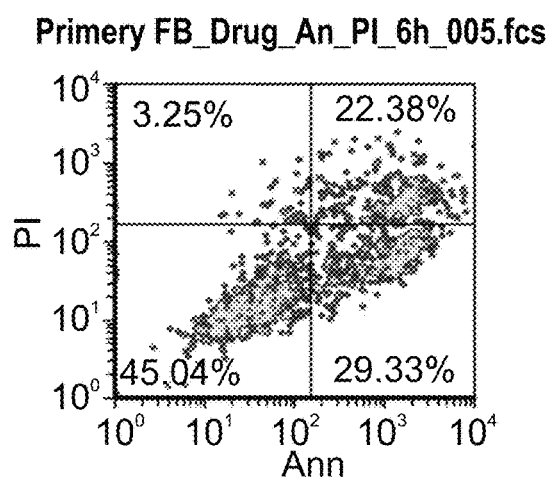
Figure 3E:
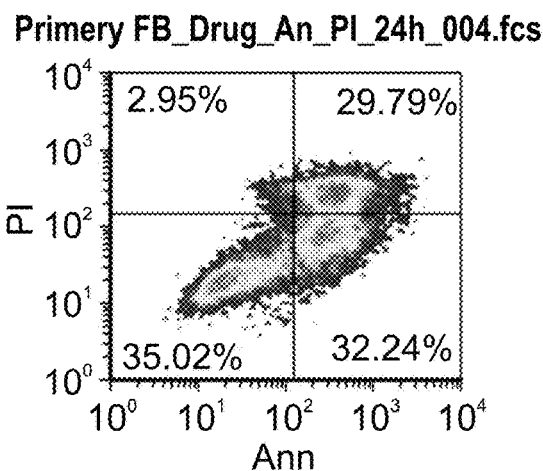

FIGS. 3A-C present flow cytometry analysis of fibroblast cells treated with 10 μM of chimera 358 for 2 hours (FIG. 3A), 4 hours (FIG. 3B) and 8 hours (FIG. 3C), showing detection of apoptotic/necrotic stages of the cells.

As can be seen in FIGS. 3A-C, the results indicate that cell death caused by Chimera 358 to primary fibroblast (FB) cells is moderate, compared to cancer cells, particularly in irreversible manner. These results serve as preliminary indication for safety and selectivity of the conjugates, according to embodiments of the present invention.

Example 3

In Vivo Activity Experiments

In one experiment (Experiment 1), 14 human melanoma model mice (immune-deficient xenograft) were treated daily for 7 days by IP injection with of Chimera 358 followed by 2 days of observation according to the following groups: 4 control mice treated with saline, 5 mice treated with 25 mg and 5 mice treated with 10 mg.

Figure 4:
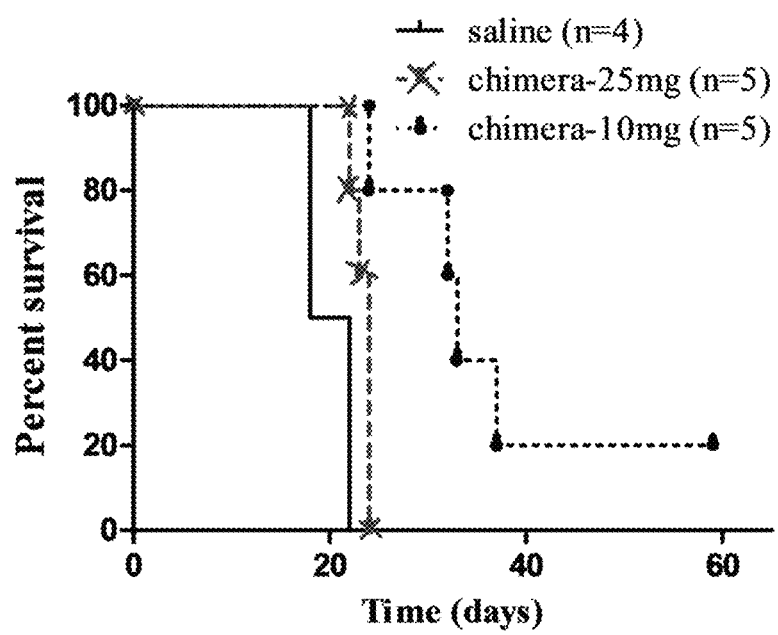
FIG. 4 presents the results of Experiment 1 that included a 7 days IP injection treatment course using an exemplary anti-cancer conjugate Chimera 358 in 4 human melanoma model control mice (solid line), 5 human melanoma model mice which received 25 mg (X-marked line) and 5 human melanoma model mice which received 10 mg (dot-marked line)

FIG. 4 presents the results of a 7 days IP injection treatment course using an exemplary anti-cancer conjugate Chimera 358 in 4 human melanoma model control mice which received saline (solid line), 5 human melanoma model mice which received 25 mg (X-marked line) and 5 human melanoma model mice which received 10 mg (dot-marked line).

As can be seen in FIG. 4, one mouse in the group receiving 10 mg of Chimera 358 for 7 days survived, indicating a survival of 10 mg/K in this protocol.

In another experiment (Experiment 2), 13 human melanoma model mice were treated 3 times a week by IP injection with of Chimera 358 followed by 2 days of observation according to the following groups: 3 control mice received saline, 5 mice with 5 mg and 5 mice with 10 mg. The treatment was started two weeks after grafting, when tumor development has started.

Figure 5:
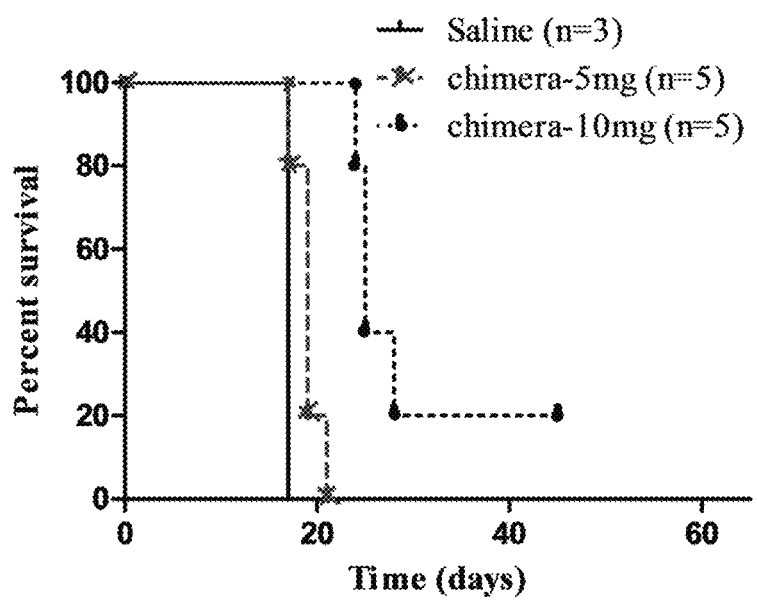
FIG. 5 presents the results of Experiment 2 that included a 3 times weekly IP injection treatment course using an exemplary anti-cancer conjugate Chimera 358 in 3 human melanoma model control mice (solid line), 5 human melanoma model mice which received 5 mg (X-marked line) and 5 mice which received 10 mg (dot-marked line)

FIG. 5 presents the results of a 3 times weekly IP injection treatment course using an exemplary anti-cancer conjugate Chimera 358 in 3 human melanoma model control mice which received saline (solid line), 5 human melanoma model mice which received 5 mg (X-marked line) and 5 mice which received 10 mg (dot-marked line). As can be seen in FIG. 5, one mouse in the group receiving 10 mg of Chimera 358 three times weekly survived, indicating a survival of 10 mg/K in this protocol.

Figure 6:
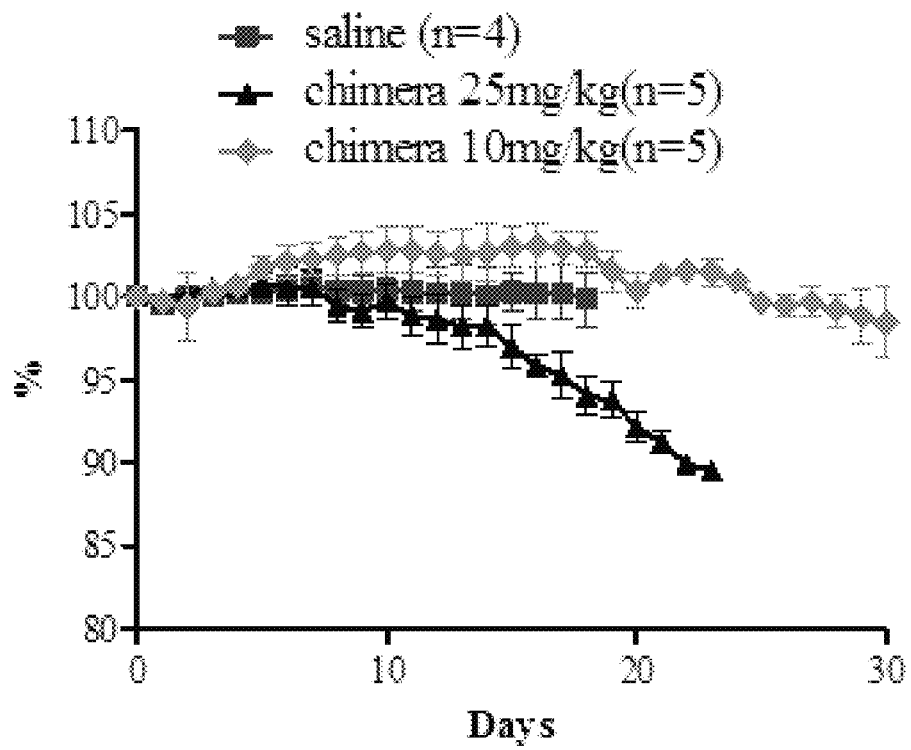
FIG. 6 presents the results of the body weight monitoring of 14 mice that undergone the treatment described in Experiment 1.

FIG. 6 presents the results of the body weight monitoring of 14 mice that undergone the treatment described in Experiment 1.

As can be seen in FIG. 6, the mice that received 25 mg of the conjugate exhibited a loss of body weight unlike the group which received 10 mg or saline.

Figure 7:
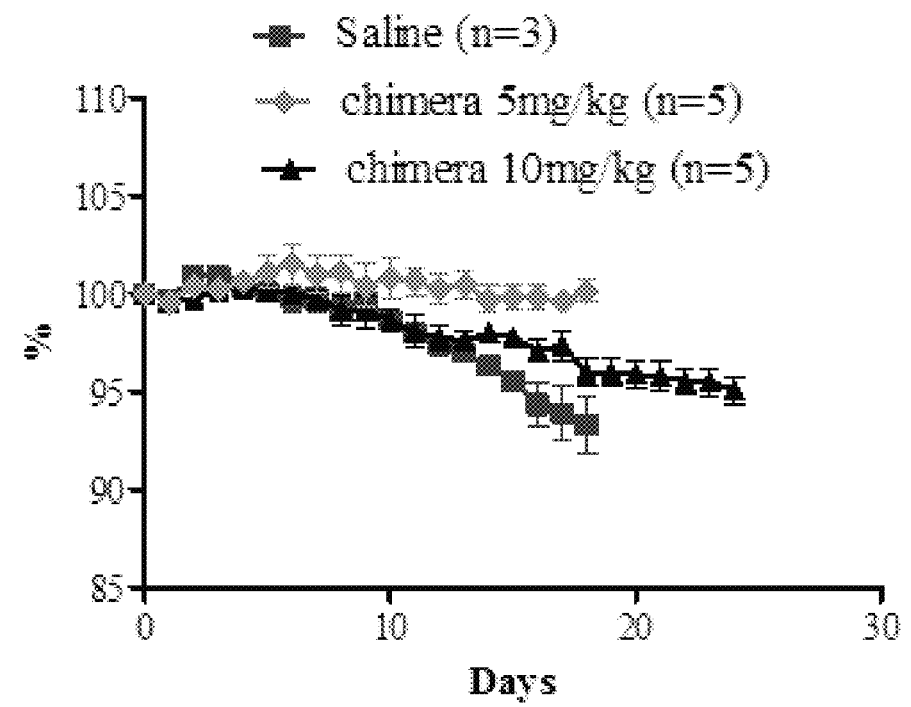
FIG. 7 presents the results of the body weight monitoring of 13 mice that undergone the treatment described in Experiment 2.

FIG. 7 presents the results of the body weight monitoring of 13 mice that undergone the treatment described in Experiment 2.

As can be seen in FIG. 7, the mice that received 5 mg of the conjugate maintained their body weight unlike the control group and the group which received 10 mg.

Figure 8:
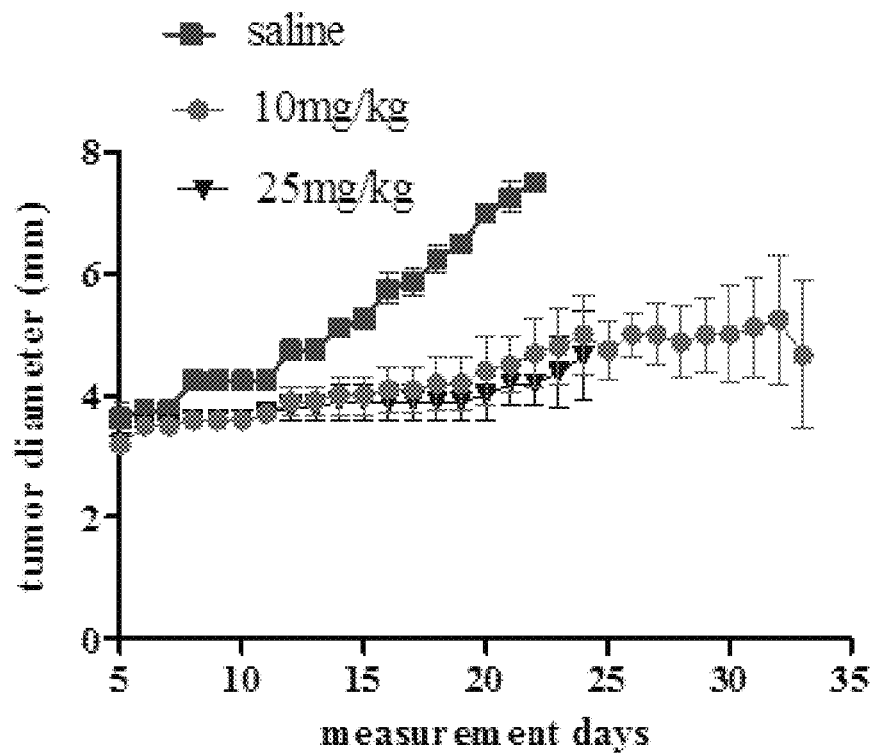
FIG. 8 presents the results of WM-266.4 cell proliferation (tumor size) in vivo after injection to the mice undergone the treatment described in Experiment 1.

FIG. 8 presents the results of WM-266.4 cell proliferation (tumor size) in vivo after injection to the mice undergone the treatment described in Experiment 1.

As can be seen in FIG. 8, the tumors of the control mice that received saline kept growing while the tumors in the mice receiving the treatment grew to a much lesser extent, whereas the group that received 10 mg exhibited a notable decrease in tumor size after four weeks of the treatment.

Figure 9:
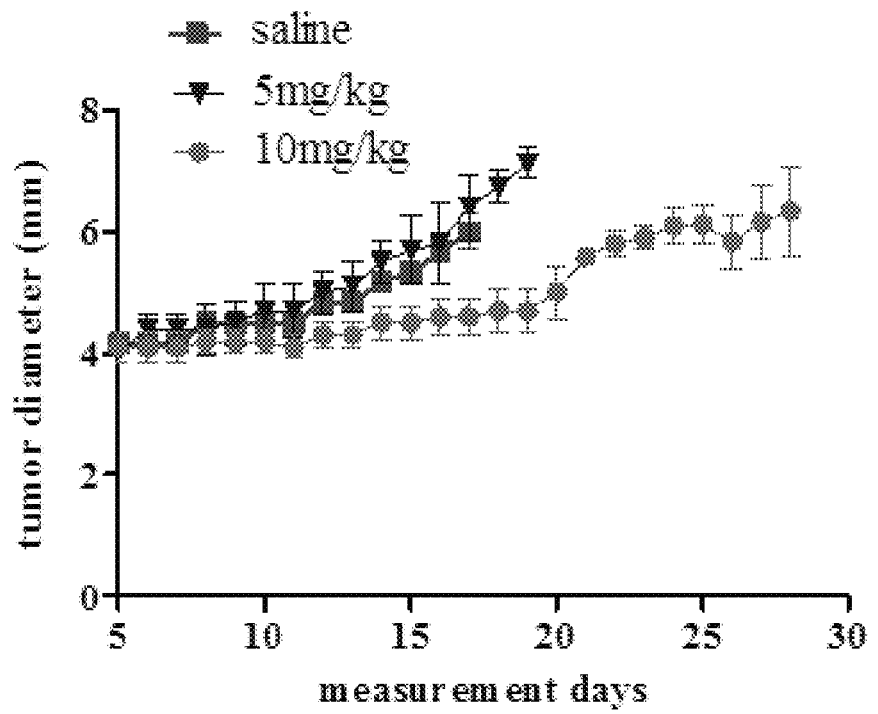
FIG. 9 presents the results of WM-266.4 cell proliferation (tumor size) in vivo after injection to the mice undergone the treatment described in Experiment 2.

FIG. 9 presents the results of WM-266.4 cell proliferation (tumor size) in vivo after injection to the mice undergone the treatment described in Experiment 2.

As can be seen in FIG. 9, the tumors of the control mice that received saline and the group that received 5 mg of the conjugate kept growing until mice expired, while the tumors in the mice receiving 10 mg of the conjugate grew to a much lesser extent.

Example 4

Additional Embodiments

Synthesis of Dimethyl and Monomethyl Triazene Amonafide Conjugates

Triazene-based conjugates are capable of undergoing hydrolysis under physiological conditions to deliver and release cytotoxic monomethyl triazene (further decomposes to methyl diazonium) alkylating agents. When combined with any other conjugated drugs, such as amonafide and campthothecin, the resulting conjugates are effectively triple chimeras, namely three-drug conjugates that upon hydrolysis releases three bioactive molecules.

In one embodiment, referred to herein as Combomera 7, amonafide (Topo II inhibitor), methyl diazonium (DNA methylating) and camptothecin (Topo I inhibitor) are released after exposure to the bio-hydrolytic environment. The synthesis of Combomera 7 is presented in Scheme 12.

Scheme 12
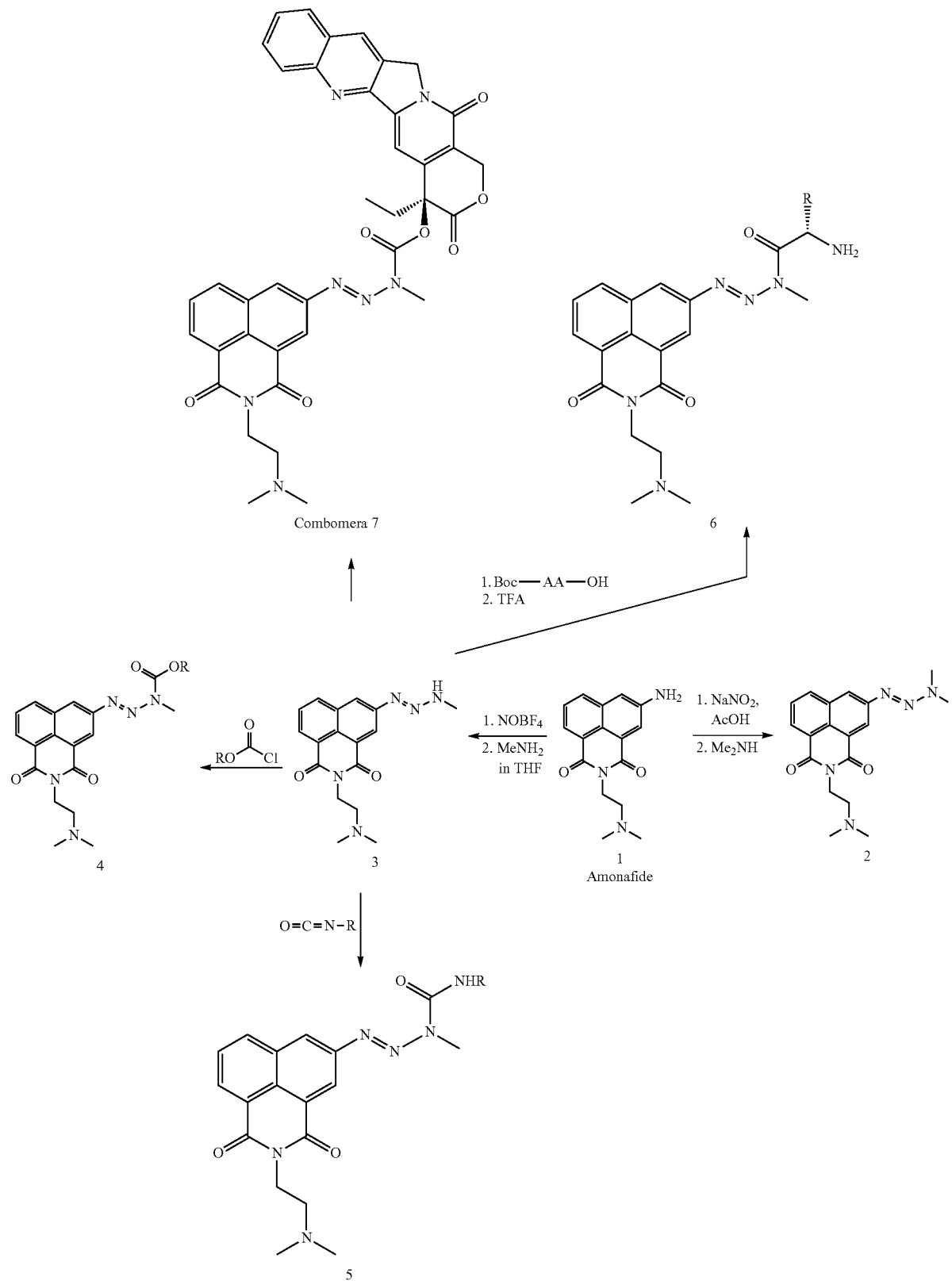
R = Alkyl, Aryl

Exemplary synthesis of 2-(2-(dimethylamino)ethyl)-5-(3,3-dimethyltriaz-1-en-1-yl)-1H-benzo[de]isoquinoline-1,3(2H)-dione (2) [following Diana, P. et al., Chem Med Chem 2011, 6, 1291-1299]:

Amonafide (0.85 g, 3 mmol) was reacting in glacial acetic acid (6 mL) with a solution of sodium nitrite (0.21 g, 3 mmol) in a small amount of water (1 mL). The reaction was carried out at 0° C. under a nitrogen atmosphere. The mixture was neutralized at 0° C. with saturated $Na_2CO_3$. 40% aqueous $Me_2NH$ solution (2 mL) was carefully added and reaction mixture was stirred at room temperature for 2 hours crude product was extracted with ethyl acetate (50 mL×3), organic phases were combined, brined and solvent evaporated to give 0.74 gram of crude 2, which was further chromatographed (ethyl acetate) to yield pure 2 as yellow powder (0.53 gram, 68%). Rf=0.40 (EtAc); MS (ES), M/Z (%): 339.17 (100). $^1$H NMR (400 MHz, $CDCl_3$): 2.37 s (2Me), 2.66 t ($CH_2$, 7=6.4 Hz), 3.29 bs (Me), 3.59 bs (Me), 4.33 t ($CH_2$, 7=6.4 Hz), 7.65 t (1H, 7=7 Hz), 8.07 d (1H, 7=1.5 Hz), 8.12 d (1H, 7=7 Hz), 8.41 d (1H, 7=7 Hz), 8.78 d (1H, J=1.5 Hz), $^{13}$C NMR (100 MHz, $CDCl_3$): 36.1 (q), 38.2 (t), 43.4 (q), 45.8 (q), 57.0 (t), 122.6 (s), 123.2 (s), 124.4 (d), 124.7 (d), 126.4 (d), 127.0 (d), 129.7 (d), 131.3 (d), 132.8 (d). 133.8 (d), 140.0 (s), 147.7 (s), 164.5 (s), 164.6 (s). IR (KBr): λ2905, 1645, 1420, 1350, 1110, 920.

Exemplary Synthesis of 2-(2-(dimethylamino)ethyl)-5-(3-methyltriaz-1-en-1-yl)-1H-benzo[de]isoquinoline-1,3(2H)-dione (3)

Amonafide (810 mg, 2.8 mmol) was stirred in dry acetonitrile (60 mL) under argon. Thereafter, it was cooled to −5° C. and nitrosonium tetrafluoroborate (670 mg, 5.8 mmol) in acetonitrile was added. The resulting solution was stirred for 1 hour at −5° C. and added dropwise to a mixture of cold ether (100 mL), water (20 mL), trimethylamine (5 mL), and methylamine (2.0 M solution in THF, 11 mL, 2.4 mmol). The mixture was kept at 0° C. for additional 2 hours and further was extracted with ethyl acetate. The organic layer was dried over anhydrous sodium sulfate and evaporated to give 3 as a reddish residue, which was purified by flash chromatography (1:4 hexane-EtAc, 790 mg, 82%). Rf=0.35 (EtAc); MS (ES), M/Z (%): 325.36 (100). $^1$H NMR (400 MHz, $CDCl_3$): 2.33 s (2Me), 2.62 t ($CH_2$, 7=6.5 Hz), 3.19 bs (Me), 4.36 t ($CH_2$, 7=6.5 Hz), 7.57 t (1H, 7=7 Hz), 8.03 d (1H, 7=1.5 Hz), 8.18 d (1H, J=7 Hz), 8.52 d (1H, 7=7 Hz), 8.64 d (1H, 7=1.5 Hz), $^{13}$C NMR (100 MHz, $CDCl_3$): 35.4 (q), 37.6 (t), 44.7 (q), 56.1 (t), 123.4 (s), 124.5 (s), 126.0 (d), 126.6 (d), 126.9 (d), 127.7 (d), 129.3 (d), 131.5 (d), 133.6 (d). 133.9 (d), 141.8 (s), 148.1 (s), 164.2 (s), 165.1 (s). IR (KBr): λ2870, 1650, 1430, 1290, 1215, 1110.

Exemplary Synthesis of Combomera (7)

Dichloro-methane solution (5 mL) of premade 4-nitrophenyl carbonate derivative of camptothecin (CPT, 316 mg, 0.6 mmol), was added slowly to a cold solution of the 3 (270 mg, 0.8 mmol), either in pyridine (5 mL) or in dichloromethane (5 mL) containing triethylamine (1.6 mmol). For the reactions in pyridine, the solution was stirred at room temperature, then poured onto ice and the resulting precipitate was dried. For the reactions in dichloromethane, the solution was evaporated under reduced pressure. The resulting solid from either method was purified by chromatography (chloroform) yielding pure yellowish product (278 mg, 65%). Rf=0.6 (chloroform); MS (ES), M/Z (%): 700.7 (60). $^1$H NMR (400 MHz, CDCl3): 0.92 t (3H, 7=6.6 Hz), 1.98 q (2H, J=6.6 Hz), 2.32 s (2Me), 2.64 t ($CH_2$, J=6.5 Hz), 3.37 s (Me), 4.25 s (2H), 4.41 t ($CH_2$, J=6.5 Hz), 4.80 bs (2H), 6.63 s (1H), 7.60-7.72 m (3H), 7.88 s (1H), 8.02-8.05 m (3H), 8.21 d (1H, J=7 Hz), 8.49 d (1H, J=7 Hz), 8.63 d (1H, J=1.5 Hz), IR (KBr): λ2885, 1655, 1415, 1270, 1245, 1040.

Synthesis of Protected Dimethyl and Monomethyl Triazene Phenylalanine Building Units Triazene N-protected Phe building blocks for solid phase synthesis are presented in Scheme 13.

Scheme 13

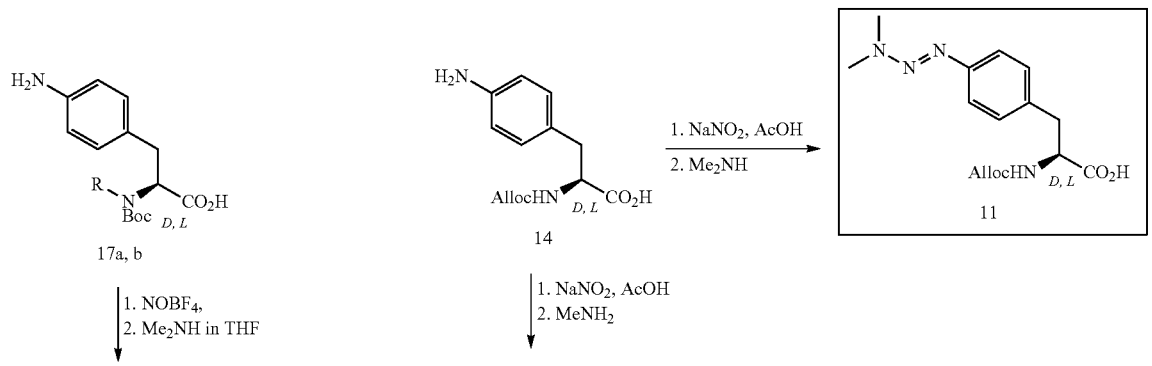

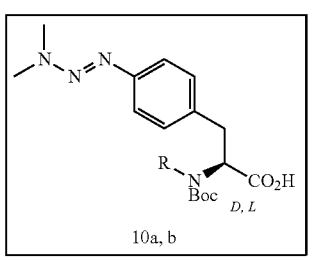
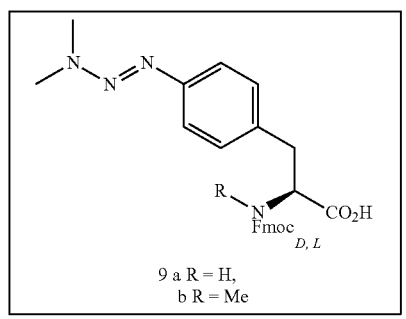
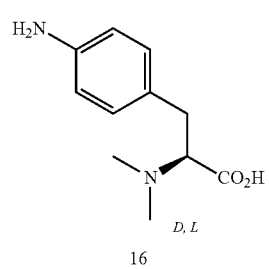
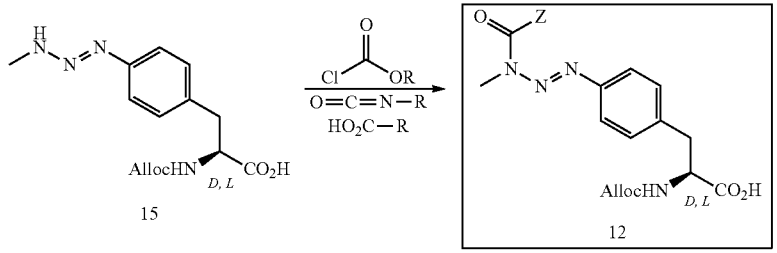
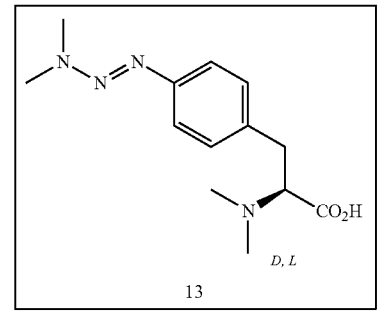

Exemplary Synthesis of 9b Starting from 17b

L-3-(4-aminophenyl)-2-(methyl-Boc-amino) propanoic acid 17b (294 mg, 1.0 mmol) was stirred in dry acetonitrile (40 mL) under argon. Thereafter, it was cooled to −5° C. and nitrosonium tetrafluoroborate (335 mg, 2.9 mmol) in acetonitrile was added. The resulting solution was stirred for 1 h at −5° C. and added dropwise to a mixture of cold ether (100 mL), water (20 mL), trimethylamine (5 mL), and dimethylamine (2.0 M solution in THF, 6 mL, 1.2 mmol). The mixture was kept at 0° C. for 2 h more and further was extracted with ethyl acetate. The organic layer was dried over anhydrous sodium sulfate and evaporated to give 9b as a yellowish residue, which was purified by flash chromatography (1:3 hexane-EtAc, 231 mg, 68%). Rf=0.60 (EtAc); MS (ES), M/Z (%): 351.4 (70). $^1$H NMR (400 MHz, CDCl$_3$): 1.39 s (9H), 3.27 bs (Me), 3.41 s (Me), 3.47 m (1H), 3.52 m (1H), 3.56 bs (Me), 4.76 m (1H), 7.25 d (2H, J=8 Hz), 8.82 d (1H, J=8 Hz), $^{13}$C NMR (100 MHz, CDCl$_3$): 27.8 (q), 34.3 (q), 35.0 (t), 36.7 (q), 44.3 (q), 66.4 (d), 74.4 (s), 126.5 (d), 129.6 (d), 132.2 (s), 145.8 (s), 156.9 (s), 172.3 (s). IR (KBr): λ2820, 1690, 1520, 1100, 1085, 950.

Solid Phase Peptide Synthesis of Dimethyl Triazene Phenylalanine Peptides

Other hydrophobic amino acids can be useful for synthesis of hydrophobic oligotriazene peptides.

Building unit 9b was incorporated into solid phase peptide synthesis using Fmoc protocol for preparation of hydrophobic DNA hyper-methylating tetrapeptide 18, as presented in Scheme 14.

Scheme 14

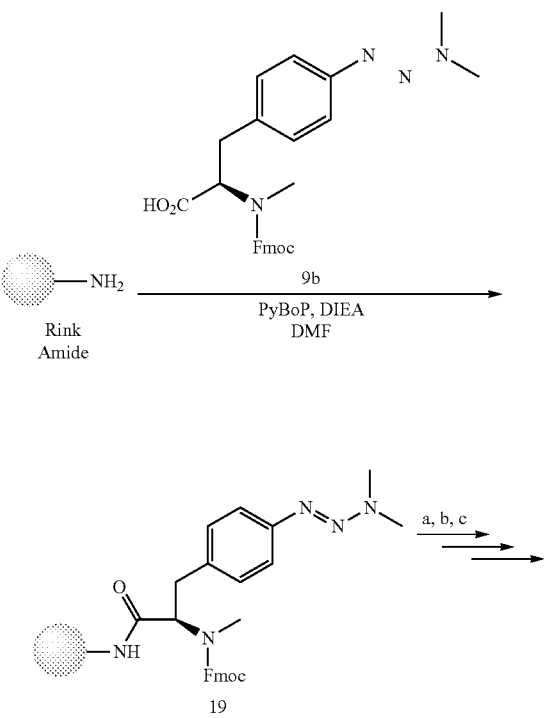

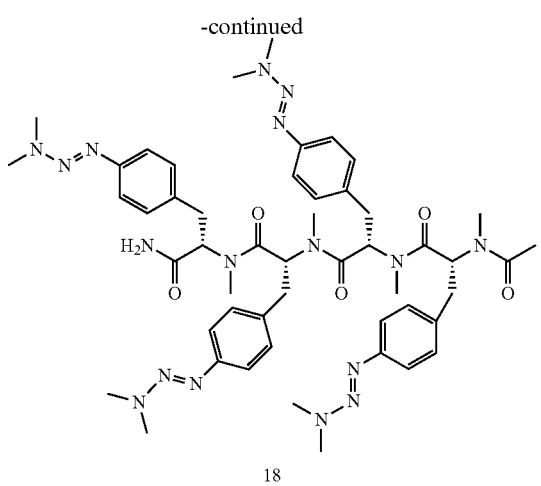

18 a. (i) PyBoP, DIEA, DMF, (ii) piperidine in DMF (several cycles);
b. Ac₂O, DIEA, DMF/DCM; c. TFA/H₂O Exemplary Synthesis of 18

In a reaction vessel equipped with a sintered glass bottom, rink amide MBHA resin (substitution level, 0.56 mmol/g, 1 g) was swelled in DMF by agitation overnight. The Fmoc group was removed from the resin by treatment with 20% of piperidine in DMF (10 mL) for 15 min. This step was repeated twice. After washing, the resin with DMF (7×10 mL, 2 min each), building unit 9b (3 eq., 1.68 mmol, 0.59 g), pre-activated with PyBroP (3 eq., 1.68 mmol, 0.7 g), and DIEA (6 eq., 21 mmol, 0.52 mL) for 4 min at room temperature in DMF (7 mL) was added and was allowed to react for 1 h at room temperature. After coupling, the peptidyl resin was washed with DMF (5×7 mL, 2 min each). The completion of the reaction was monitored by ninhydrin test (Kaiser test, yellow). Linear peptide was synthesized under standard Fmoc protocol, with three equivalents of 9b acid and three equivalents of PyBrop as coupling reagent. The deblock mixture was a mixture of 80:20 N,N-dimethylformamide (DMF)/piperidine (v/v). This cycle was repeated 4 times. After last Fmoc deprotection, Ac2O (10 eq), DIEA (15 eq) in 10 mL DMF/DCM (1:1) was added and the resin was shacked at rt for 2 h. After washings (DMF 7×10 mL, DCM 3×10 mL, 2 min each), resin was dried under vacuum for 2 h. The peptide cleaved from the resin using a cold solution of 98:2 TFA/H₂O (7 mL) for 15 min at 0° C. under argon and then 45 min at room temperature under argon. The resin was filtered and washed with the cold TFA (3 mL). The filtrate solution was evaporated to give an oily residue, which solidified upon the addition of cold Et₂O/hexane (1:1). Centrifugation and decantation of the organic layer afforded the crude product. It was further subjected to purification by preparative HPLC on RP-18 (AcCN/H₂O) to yield pure 18 (98.2% purity, 286 mg, 63% yield). HPLC purification was done on ECOM semi-preparative system withdual UV detection at 254 and 214 nm. Phenomenex GeminiVR 10 mm C18 110 A°, LC 250×21.2 mm prep column was utilized. The column was kept at room temperature. The eluent solvents were 0.1% trifluoroacetic acid (TFA) in H₂O (A) and 0.1% TFA in acetonitrile (ACN) (B). A typical elution was a gradient of 100% A to 50% B over 45 min at a flow rate of 25 mL/min. Analytical RP-HPLC was performed on an UltiMate 3000 system (Dionex) using a Vydac C18 column (250 3 4.6 mm) with 5 mm silica (pore size, 300 A°). Linear gradient elution (0 min 0% B; 5 min 0% B; 50 min 90% B) with eluent A (0.1% TFA in water) and eluent B (0.1% TFA in acetonitrile: H₂O [80:20, v/v]) was used at a flow rate of 1 mL/min.uct. LC-MS: room temperature 11.47 min; M/Z (%): 989.2 (MH⁺, 75%).

Additional Conjugate Embodiments

Additional embodiments of the present invention, amonafide based triazene combomeras starting compound 9 [Peduto, A. et al., Bioorg. Med. Chem., 19 (2011) 6419-6429], are presented in Scheme 15.

Scheme 15

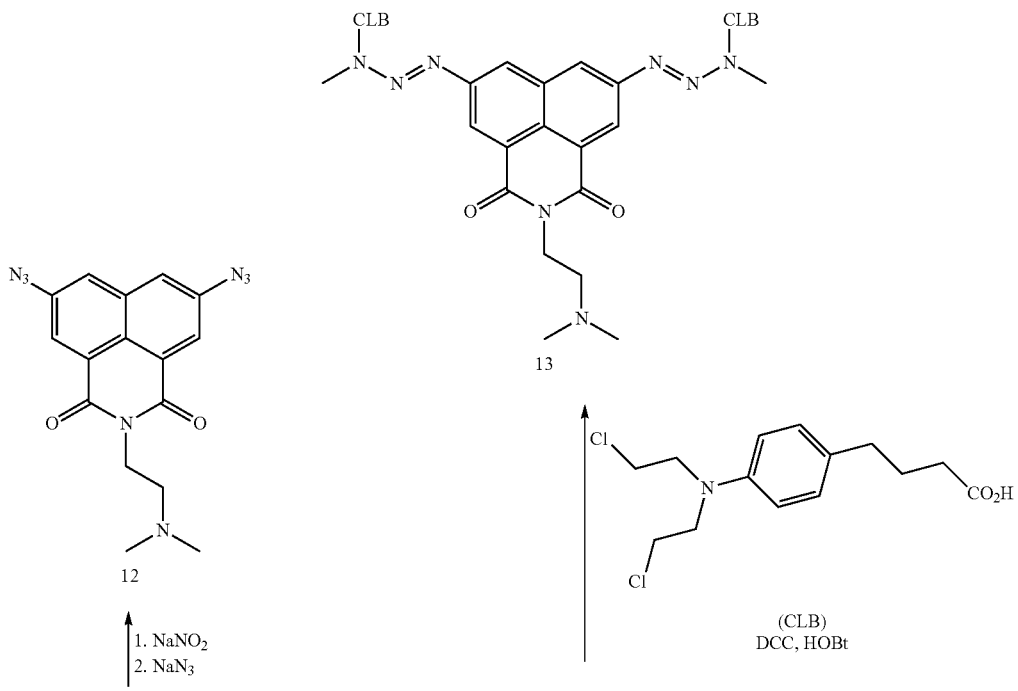

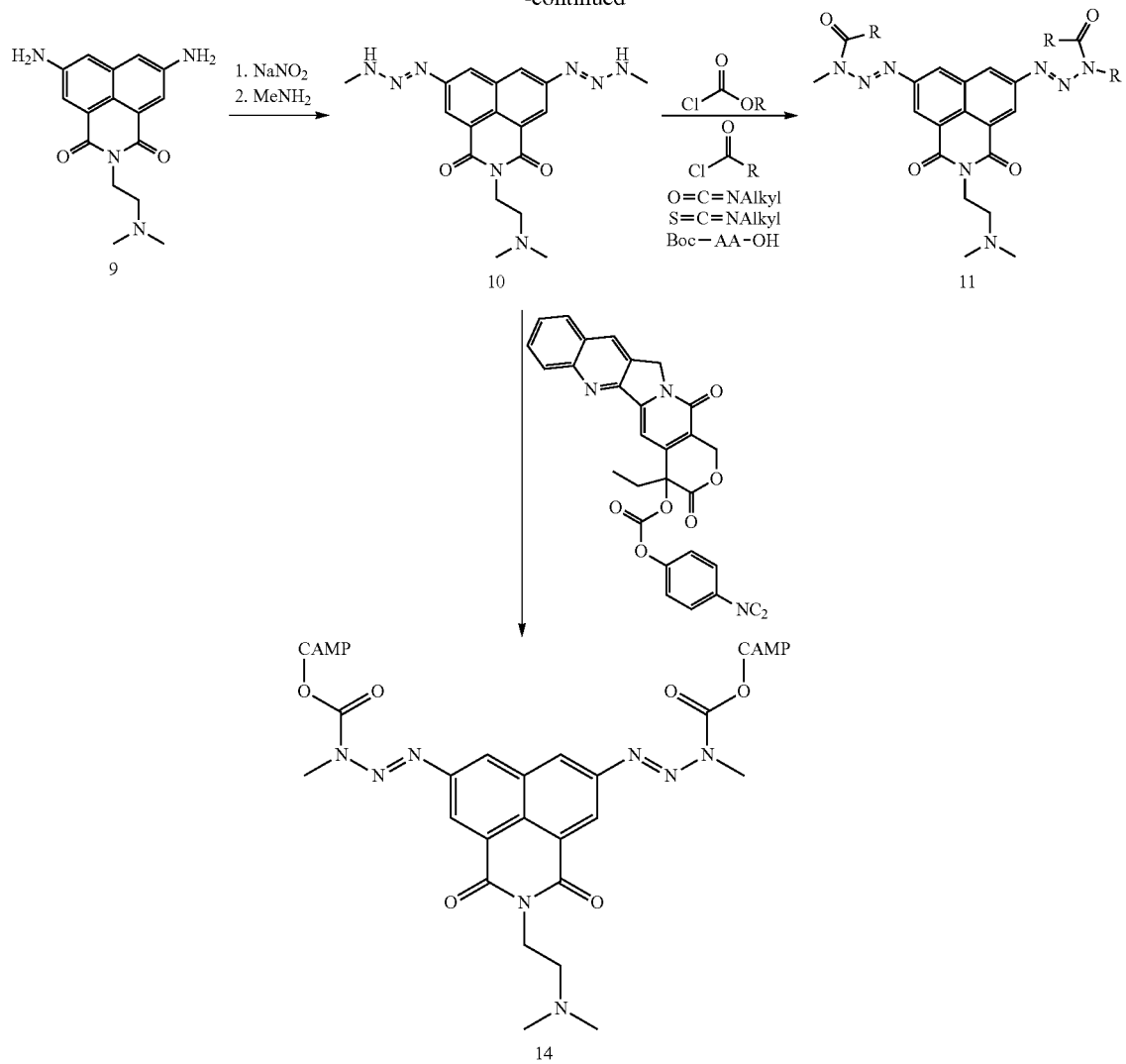
Yet additional embodiments of conjugates with triazene moiety are presented in Scheme 16.
Scheme 16
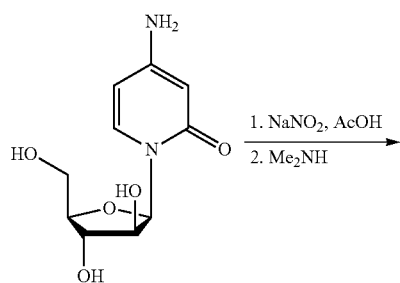
Cytarabine-antimetabolite

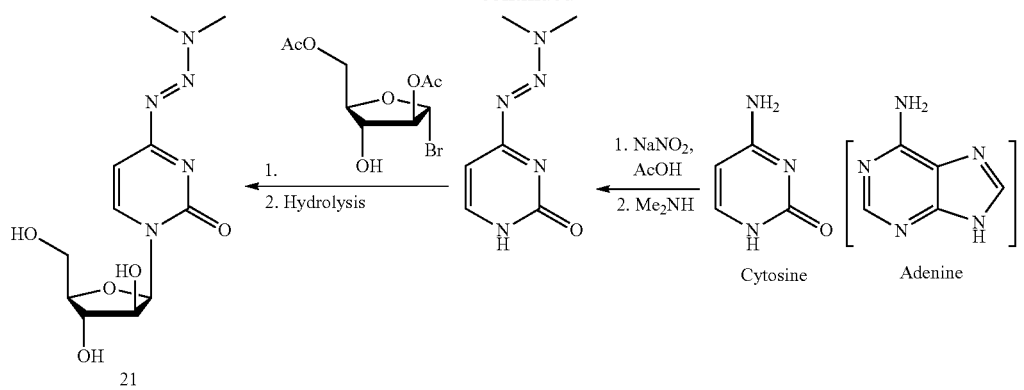
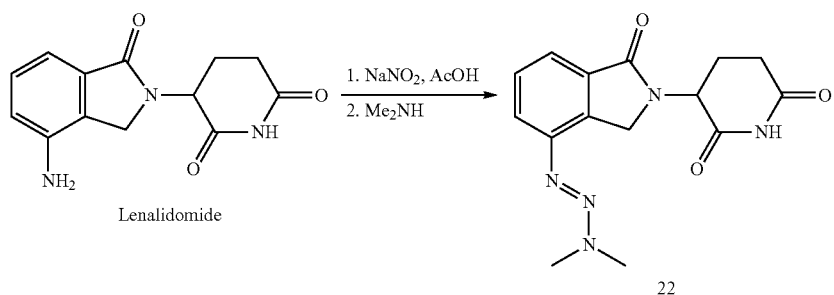
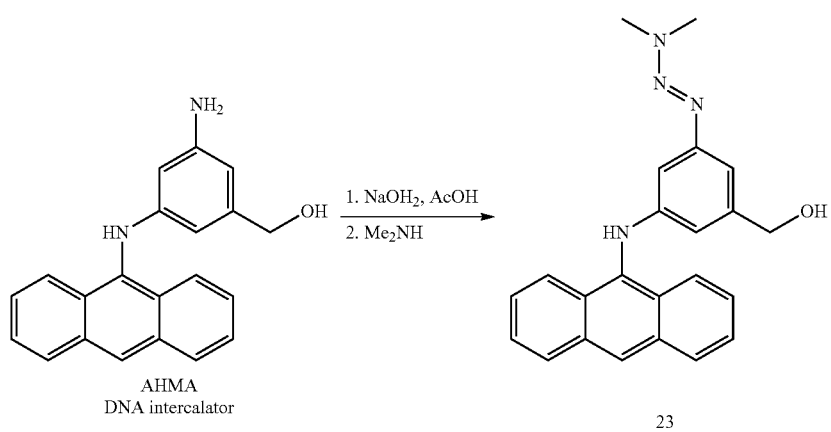
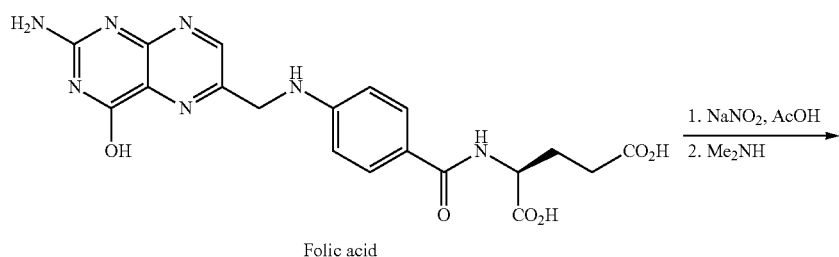

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A conjugate comprising:
   (a) a residue of a first anticancer bioactive agent, said first anticancer bioactive agent having a first chemical structure;
   (b) a residue of a second anticancer bioactive agent, said second anticancer bioactive agent having a second chemical structure; and
   (c) a monomethyl triazene linking moiety covalently bonding said first residue and said second residue to form the conjugate, wherein:
   said first bioactive agent is different than said second bioactive agent;
   said first bioactive agent and said second bioactive agent have a first functional group and a second functional group, respectively;
   each of said first anticancer bioactive agent and said second bioactive agent is selected from the group consisting of amonafide, camptothecin, chlorambucil, colchicine, cytarabine and doxorubicin;
   said monomethyl triazene linking moiety is a biocleavable moiety being formed by coupling said first functional group and said second functional group, such that biocleaving said monomethyl triazene linking moiety releases both said first anticancer bioactive agent characterized by said first chemical structure and said second anticancer bioactive agent characterized by said second chemical structure, and further releases a cytotoxic monomethyl triazene.

2. The conjugate of claim 1, wherein each of said first functional group and said second functional group is selected from the group consisting of amine, hydroxyl, carboxyl and ester.

3. The conjugate of claim 1, wherein each of said first bioactive agent and said second bioactive agent is independently characterized by a first therapeutic activity and a second therapeutic activity, respectively, and at least one of said first therapeutic activity and said second therapeutic activity is a low or moderate therapeutic activity.

4. The conjugate of claim 1, wherein each of said first therapeutic activity and said second therapeutic activity is a low or moderate therapeutic activity.

5. The conjugate of claim 3, wherein the conjugate is characterized by exerting a therapeutic activity greater than each of said first therapeutic activity and said second therapeutic activity alone or in combination.

6. The conjugate of claim 1, wherein said first bioactive agent is camptothecin, and said second bioactive agent is chlorambucil.

7. The conjugate of claim 1, wherein said first bioactive agent is camptothecin, and said second bioactive agent is colchicine.

8. The conjugate of claim 1, wherein said first bioactive agent is amonafide, and said second bioactive agent is chlorambucil.

9. The conjugate of claim 1, wherein said first bioactive agent is amonafide, and said second bioactive agent is camptothecin.

10. The conjugate of claim 1, wherein said first bioactive agent is cytarabine, and said second bioactive agent is chlorambucil.

11. The conjugate of claim 1, wherein said first bioactive agent is doxorubicin, and said second bioactive agent is chlorambucil.

12. The conjugate of claim 1, wherein said first bioactive agent is doxorubicin, and said second bioactive agent is camptothecin.

13. The conjugate of claim 1, wherein said first bioactive agent is cytarabine, and said second bioactive agent is camptothecin.

14. A conjugate selected from the group consisting of:

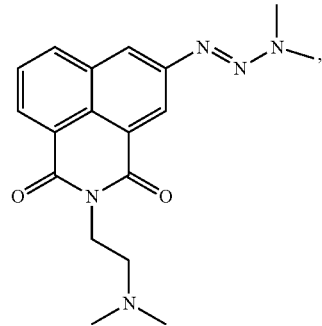

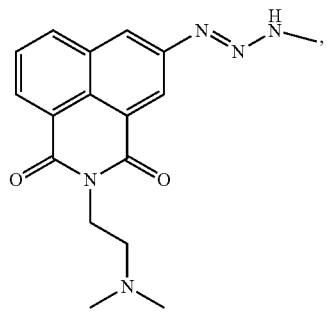

73
-continued
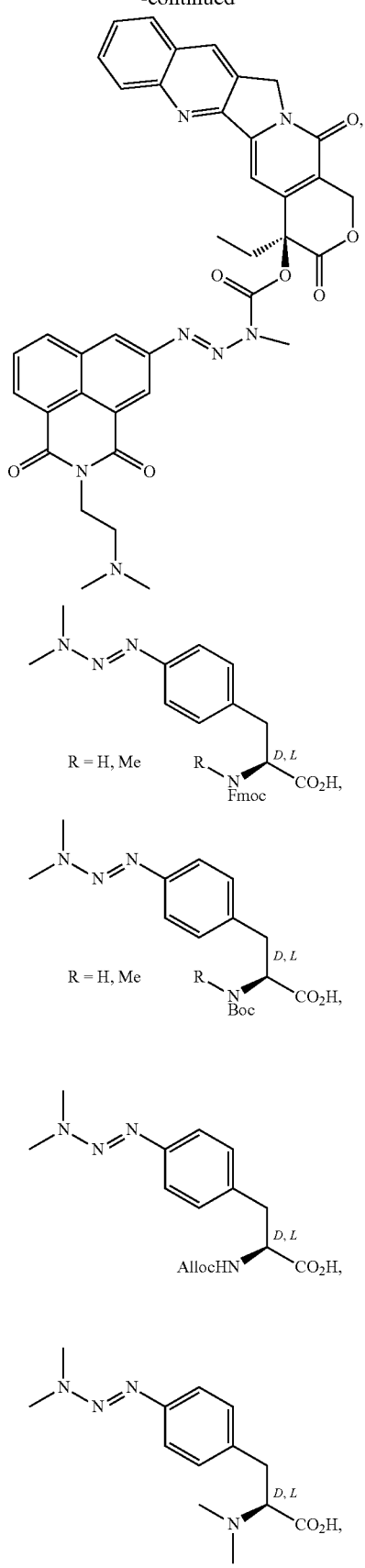
74
-continued
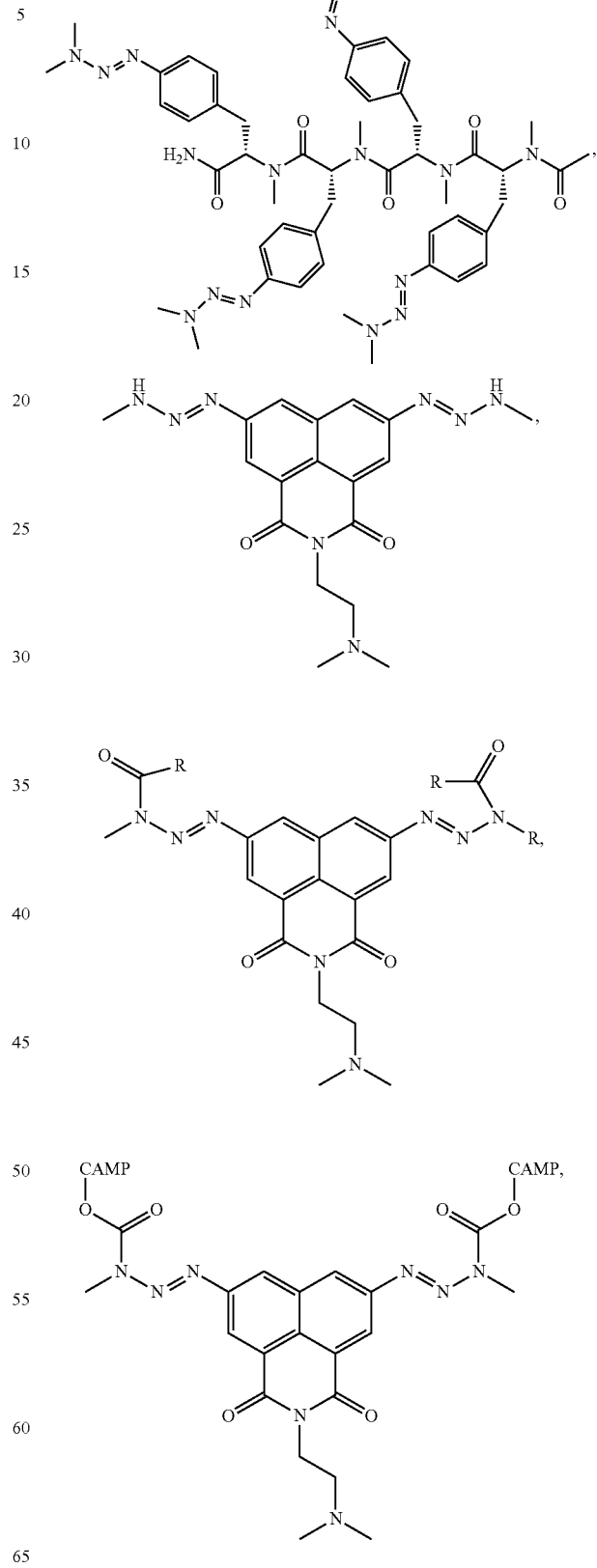

-continued

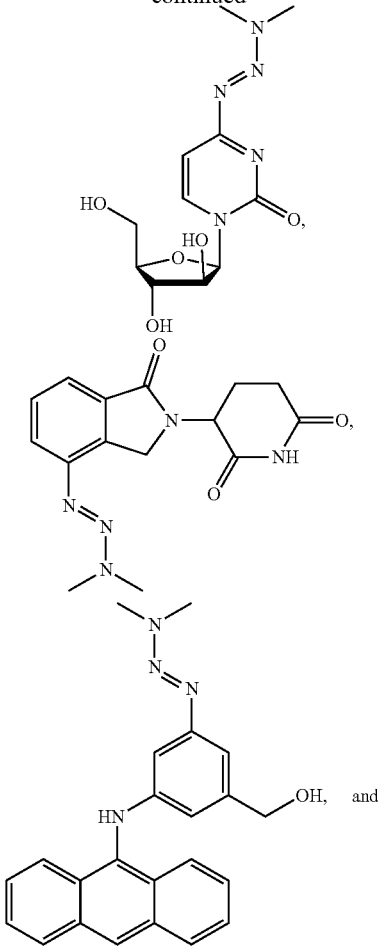

-continued

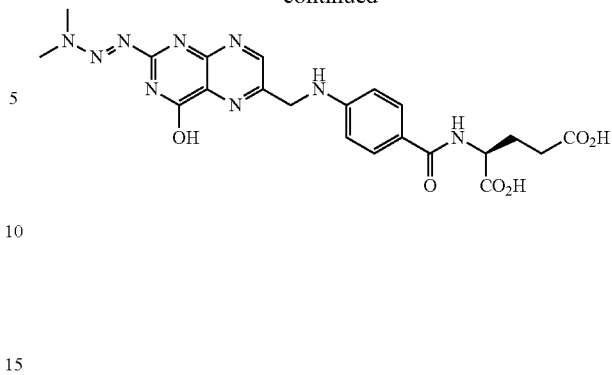

15. A pharmaceutical composition comprising, the conjugate of claim 1 as an active ingredient, and a pharmaceutically acceptable carrier.

16. The pharmaceutical composition of claim 15, being packaged in a packaging material and identified in print, in or on said packaging material, for use in the treatment of cancer.

17. A method of treating cancer in a subject, the method comprising, administering to said subject a therapeutically effective amount of the conjugate of claim 1.

18. A process of preparing the conjugate of claim 1, the process comprising coupling said first bioactive agent to said second bioactive agent via said first functional group and said second functional group, to thereby form said linking moiety.

19. The process of claim 18, further comprising, prior to said coupling, modifying at least one of said first bioactive agent or said second bioactive agent so as to exhibit said first functional group or said second functional group, respectively.

* * * * *